US012575896B2

(12) United States Patent　　　　(10) Patent No.:　US 12,575,896 B2

Moisa　　　　　　　　　　　　　　　(45) Date of Patent:　　Mar. 17, 2026

(54) CATHETER NAVIGATION SYSTEMS AND METHODS

(71) Applicant: KARDIUM INC., Burnaby (CA)

(72) Inventor: Saar Moisa, Vancouver (CA)

(73) Assignee: KARDIUM INC., Burnaby (CA)

( * ) Notice: Subject to any disclaimer, the term of this patent is extended or adjusted under 35 U.S.C. 154(b) by 300 days.

(21) Appl. No.: 18/536,602

(22) Filed: Dec. 12, 2023

(65) Prior Publication Data

US 2024/0099788 A1　　　Mar. 28, 2024

Related U.S. Application Data

(63) Continuation of application No. 17/389,972, filed on Jul. 30, 2021, now Pat. No. 11,918,303, which is a (Continued)

(51) Int. Cl.
*A61B 34/20*　　　　(2016.01)
*A61B 90/00*　　　　(2016.01)

(52) U.S. Cl.
CPC ............... *A61B 34/20* (2016.02); *A61B 90/36* (2016.02); *A61B 2034/2046* (2016.02)

(58) Field of Classification Search
CPC .. A61B 34/20; A61B 90/36; A61B 2034/2046
See application file for complete search history.

(56) References Cited

U.S. PATENT DOCUMENTS 5,697,377 A　　12/1997　Wittkampf
6,546,270 B1　　4/2003　Goldin et al.

(Continued)

FOREIGN PATENT DOCUMENTS

EP　　3372186 A1　　9/2018
EP　　3422297 A1　　1/2019

(Continued)

OTHER PUBLICATIONS

Notice of Allowance issued in U.S. Appl. No. 18/536,492 mailed Oct. 18, 2024.

(Continued)

*Primary Examiner* — Rochelle D Turchen

(74) *Attorney, Agent, or Firm* — ROSSI, KIMMS & McDOWELL LLP

(57)　　　　　　　ABSTRACT

A catheter navigation system may be configured to produce a plurality of location signal sets indicating a three-dimensional location of a portion of a catheter in a bodily cavity and a plurality of contact signal sets indicating degrees of detected-transducer-to-tissue contact within the bodily cavity. The catheter navigation system may be configured to, based on the location signal sets and the contact signal sets progressively visually represent in a progressively enlarging manner at least a portion of an envelope representing an interior volume of the bodily cavity, concurrently with a visual representation of transducer graphical elements representing transducers that produce the location signal sets, the contact signal sets, or both, of the portion of the catheter. The visual representation of the at least the portion of the envelope, the transducer graphical elements, or both, may respectively visually represent historical and/or presently detected degrees of transducer-to-tissue contact.

23 Claims, 16 Drawing Sheets

*1400*

Related U.S. Application Data continuation of application No. PCT/CA2020/050061, filed on Jan. 21, 2020.

(60) Provisional application No. 62/865,460, filed on Jun. 24, 2019, provisional application No. 62/805,338, filed on Feb. 14, 2019.

(56) References Cited

U.S. PATENT DOCUMENTS

| | | | |
|---|---|---|---|
| 7,720,520 B2 | 5/2010 | Willis |
| 8,123,721 B2 | 2/2012 | Tegg |
| 8,825,144 B2 | 9/2014 | Starks |
| 8,906,011 B2 | 12/2014 | Gelbart |
| 8,920,411 B2 | 12/2014 | Gelbart et al. |
| 9,198,592 B2 | 12/2015 | Reinders |
| 9,452,016 B2 | 9/2016 | Moisa |
| 9,492,227 B2 | 11/2016 | Lopes |
| 9,980,653 B2 | 5/2018 | Lichtenstein et al. |
| 10,368,936 B2 | 8/2019 | Brewster et al. |
| 10,814,099 B2 | 10/2020 | Funk |
| 2007/0265526 A1 | 11/2007 | Govari |
| 2008/0085042 A1 | 4/2008 | Trofimov et al. |
| 2013/0035576 A1 | 2/2013 | O'Grady et al. |
| 2016/0000357 A1 | 1/2016 | Harlev et al. |
| 2017/0143201 A1 | 5/2017 | Claude |
| 2017/0202469 A1 | 7/2017 | Scharf |
| 2017/0330487 A1 | 11/2017 | Harlev |
| 2019/0269367 A1 | 9/2019 | Reinders et al. |
| 2020/0085329 A1 | 3/2020 | Markovitz |

FOREIGN PATENT DOCUMENTS

| | | |
|---|---|---|
| EP | 4046574 A1 | 8/2022 |
| WO | 2012100184 A2 | 7/2012 |
| WO | 2012100185 A2 | 7/2012 |
| WO | 2017100902 A1 | 6/2017 |

OTHER PUBLICATIONS

Office Action issued in U.S. Appl. No. 18/536,641 mailed Oct. 28, 2024.

Notice of Allowance issued in U.S. Appl. No. 17/389,972 mailed Dec. 27, 2023.

Non-Final Office Action issued in copending U.S. Appl. No. 18/536,641 mailed Jul. 24, 2024.

Non-Final Office Action issued in copending U.S. Appl. No. 18/536,492 mailed Jul. 26, 2024.

Amendment filed in copending U.S. Appl. No. 18/536,492 on Aug. 30, 2024.

Preliminary Amendment filed in copending U.S. Appl. No. 18/536,569 on Aug. 30, 2024.

Office Action issued in copending U.S. Appl. No. 18/536,569 mailed Sep. 6, 2024.

Amendment filed in copending U.S. Appl. No. 18/536,641 on Sep. 6, 2024.

Bhakta. "Principles of Electroanatomic Mapping." Indian Pacing and Electrophysiology Journal. 2008: 32-50. Vol. 8, No. 1.

International Search Report issued in Intl. Appln. No. PCT/CA2020/050061 mailed Apr. 23, 2020.

Written Opinion issued in Intl. Appln. No. PCT/CA2020/050061 mailed Apr. 23, 2020.

Kottkamp et al. "Global multielectrode contact mapping plus ablation with a single catheter: Preclinical and preliminary experience in humans with atrial fibrillation." Journal of Cardiovascular Electrophysiology. 2017:1-10.

Mounsey. "A novel multielectrode combined mapping and ablation basket catheter: A future player in the atrial fibrillation ablation space?" Journal of Cardiovascular Electrophysiology. 2017:1-2.

Extended European Search Report issued in European Appln. No. 20756459.2 mailed Oct. 13, 2022.

Ideker et al. "A Computerized Method for the Rapid Display of Ventricular Activation During the Intraoperative Study of Arrhythmias" Journal Circulation, Mar. 1979. pp. 449-458, vol. 59, No. 3.

Non-Final Office Action issued in U.S. Appl. No. 17/389,972 mailed May 9, 2023.

Response filed in copending U.S. Appl. No. 17/389,972 on Jul. 26, 2023.

Final Office Action issued in U.S. Appl. No. 17/389,972 mailed Sep. 6, 2023.

Amendment After Final Action filed in copending U.S. Appl. No. 17/389,972 on Nov. 6, 2023.

Moisa. Copending U.S. Appl. No. 18/536,492, filed Dec. 12, 2023 (a copy is not included because the cited application is not yet available to the public and the Examiner has ready access to the cited application).

Moisa. Copending U.S. Appl. No. 18/536,569, filed Dec. 12, 2023 (a copy is not included because the cited application is not yet available to the public and the Examiner has ready access to the cited application).

Moisa. Copending U.S. Appl. No. 18/536,641, filed Dec. 12, 2023 (a copy is not included because the cited application is not yet available to the public and the Examiner has ready access to the cited application).

Avall et al. Copending U.S. Appl. No. 18/542,972, filed Dec. 18, 2023 (a copy is not included because the cited application is not yet available to the public and the Examiner has ready access to the cited application).

Avall et al. Copending U.S. Appl. No. 18/543,301, filed Dec. 18, 2023 (a copy is not included because the cited application is not yet available to the public and the Examiner has ready access to the cited application).

Amendment filed in U.S. Appl. No. 18/536,569 on Dec. 4, 2024.

Response After Final Action filed in U.S. Appl. No. 18/536,641 on Dec. 23, 2024.

Communication Under Rule 71(3) EPC issued in European Appln. No. 20756459.2 mailed Jan. 10, 2025.

Second Response After Final Action filed in U.S. Appl. No. 18/536,641 on Jan. 28, 2025.

Notice of Allowance issued in U.S. Appln. No. 18/536, 569 mailed Jan. 15, 2025.

Notice of Allowance issued in U.S. Appl. No. 18/536,641 mailed Feb. 19, 2025.

Office Action issued in U.S. Appl. No. 18/542,972 mailed Sep. 24, 2025.

Extended European Search Report issued in European Application No. 25182875.2 mailed Sep. 12, 2025.

100

130 — MEMORY DEVICE SYSTEM

110 — DATA PROCESSING DEVICE SYSTEM

120 — INPUT-OUTPUT DEVICE SYSTEM

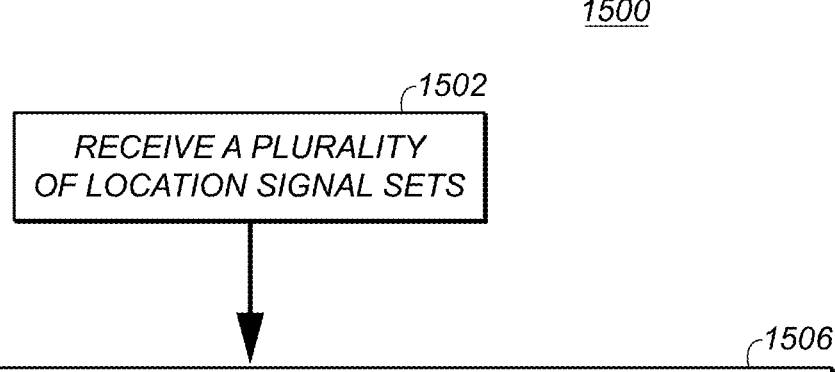

*1500*

*1502*

RECEIVE A PLURALITY
OF LOCATION SIGNAL SETS

*1506*

GENERATE AND CAUSE DISPLAY DEVICE SYSTEM TO
DISPLAY A GRAPHICAL REPRESENTATION INCLUDING A
VISUAL REPRESENTATION, IN A CONCURRENT OR
GRAPHICALLY-OVERLAPPING MANNER, OF AT LEAST
(a) AT LEAST A PORTION OF AN ENVELOPE REPRESENTING
AN INTERIOR VOLUME OF THE BODILY CAVITY, AND
(b) A PLURALITY OF GRAPHICAL ELEMENTS, EACH
GRAPHICAL ELEMENT CORRESPONDING TO A
RESPECTIVE TRANSDUCER

FIG. 15

CATHETER NAVIGATION SYSTEMS AND METHODS

CROSS-REFERENCE TO RELATED APPLICATIONS

This application is a continuation application of U.S. application Ser. No. 17/389,972, filed Jul. 30, 2021, now U.S. Pat. No. 11,918,303, issued Mar. 5, 2024, which is a Bypass Continuation Application of International Application No. PCT/CA2020/050061, filed on Jan. 21, 2020, which claims the benefit of each of U.S. Provisional Application No. 62/805,338, filed Feb. 14, 2019, and U.S. Provisional Application No. 62/865,460, filed Jun. 24, 2019, the entire disclosure of each of these applications is hereby incorporated herein by reference.

TECHNICAL FIELD

Aspects of this disclosure generally are related to systems and methods for improving navigation of a medical device or probe, such systems and methods applicable to, among other things, navigation of a medical device or probe at least percutaneously or intravascularly.

BACKGROUND

Cardiac surgery was initially undertaken using highly invasive open procedures. A sternotomy, which is a type of incision in the center of the chest that separates the sternum, was typically employed to allow access to the heart. In the past several decades, more and more cardiac operations have been performed using intravascular or percutaneous techniques, where access to inner organs or other tissue is gained via a medical device or probe known as a catheter.

Intravascular or percutaneous surgeries benefit patients by reducing surgery risk, complications, and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy and cryogenic techniques. The procedure is performed with a high success rate despite the lack of direct vision that is provided in open procedures, but is relatively complex to perform intravascularly or percutaneously because of the difficulty in correctly positioning various catheter devices to create the lesions in the correct locations. Various problems, potentially leading to severe adverse results, may occur if the lesions are placed incorrectly. For example, if tissue ablation is attempted by a transducer in a state in which the transducer is not in sufficient contact with tissue, the ablation procedure may generate thermal coagulum (i.e., a clot) in blood, which may lead to stroke or other harm to the patient. It also is particularly important to know the position of the various transducers which will be creating the lesions relative to cardiac features such as the pulmonary veins and mitral valve of a cardiac chamber. The continuity, transmurality, and placement of the lesion patterns that are formed can impact the ability to block paths taken within the heart by spurious electrical signals. The ability to achieve desired lesions is often dependent on correctly manipulating a catheter device to provide sufficient contact between various ones of the transducers and the tissues and knowing the location of the transducers relative to various anatomical features of the bodily cavity in which the transducers are manipulated. Variability associated with various anatomical structures often creates situations in which various transducers are not in sufficient contact with tissue to perform the required lesion sets, and require additional physical manipulation of a catheter device to improve the contact or positioning of the catheter device with respect to anatomical features.

Some conventional systems have attempted to address the problem of lack of visibility of an internal medical device associated with percutaneous or intravascular procedures. Some conventional systems rely on fluoroscopic imaging to view the location of an internal medical device, but the present inventor recognized that such fluoroscopic imaging does not readily produce images of tissue within the bodily cavity in sufficient detail to assess the location or particular degree of tissue contact associated with a particular transducer or to identify particular anatomical landmarks within the bodily cavity. Some conventional systems generate a graphical model of a tissue surface defining a bodily cavity into which a medical device or probe is deployed based on data acquired from electric potential-based navigation systems, electromagnetic-based navigation systems, or ultrasound-based navigation systems. Some of these conventional navigation systems rely on a three-dimensional (3D) location of the medical device or probe located in the particular bodily cavity that is to be modeled. Some of these conventional navigation systems may incorporate a user interface employed to show a 3D graphical model of the bodily cavity, which, in some of these conventional systems, is generated via a medical practitioner moving the tip of the medical device or probe (which moves a corresponding transducer) from point to point along the tissue wall. Some of these conventional systems may compile this sequence of points and, from such points, build the 3D graphical model. Such 3D graphical models typically are coarse in nature and may not provide detailed information regarding the positioning of various anatomical features (e.g., ports associated with the pulmonary veins of a cardiac chamber). In some conventional systems, the medical practitioner may manually select a region of the 3D graphical model as an anatomical port (e.g., a pulmonary vein port) and indicate that a port be added or subtracted from the interpolated 3D graphical model. For example, the medical practitioner may advance the medical device or probe up a pulmonary vein and instruct that a depiction be added to the 3D graphical model in order to depict the pulmonary vein. For example, the medical practitioner may select a region of the graphical 3D model to be removed to depict a port of the pulmonary vein. Knowing where the ports are in the bodily cavity and the correlated 3D graphical model may improve the ability of the medical practitioner to navigate the medical device or probe relative to various anatomical features associated with the ports. Unfortunately, the conventional techniques to identify the ports in the 3D graphical model are cumbersome, subject to manual error, and time consuming to implement. The present inventor recognized that these conventional systems for generating the 3D model require substantial preliminary work that burdens procedure cost, complexity, and overall duration, and that the generated model does not, among other things, allow the user to efficiently or effectively assess the quality of the image or model or a particular degree of tissue contact associated with a particular transducer.

For at least these and other reasons, the present inventor recognized that a need in the art exists for improved catheter navigation systems and methods associated with percutaneous or intravascular procedures.

SUMMARY

At least the above-discussed need is addressed and technical solutions are achieved by various embodiments of the present invention. According to some embodiments, a catheter navigation system may be summarized as including an input-output device system communicatively connected to a display device system, a memory device system storing a program, and a data processing device system communicatively connected to the input-output device system and the memory device system. According to some embodiments the data processing device system may be configured at least by the program at least to receive a plurality of location signal sets, each location signal set of the plurality of location signal sets indicative of a respective location in a sequence of locations at which at least a portion of a catheter has been sequentially located in a bodily cavity, the catheter comprising a plurality of transducers. The data processing device system may be further configured at least by the program at least to receive a plurality of contact signal sets from a first set of transducers of the plurality of transducers, each transducer of at least the first set of transducers configured to detect transducer-to-tissue contact, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity. The data processing device system may be further configured at least by the program at least to cause the display device system to progressively visually represent, in a progressively enlarging manner and based on and throughout reception of at least the plurality of location signal sets, at least a portion of an envelope, the envelope representing an interior volume of the bodily cavity. According to some embodiments, the data processing device system may be configured at least by the program at least to cause the display device system to cause the visually represented at least the portion of the envelope to visually indicate, based on at least the plurality of contact signal sets, greater-contact regions of the at least the portion of the envelope associated with relatively greater transducer-to-tissue contact in accordance with a first visual characteristic set and to visually indicate lesser-contact regions of the at least of the portion of the envelope associated with relatively lesser transducer-to-tissue contact in accordance with a second visual characteristic set, the second visual characteristic set different than the first visual characteristic set.

In some embodiments, the data processing device system may be configured at least by the program at least to cause the display device system to visually represent, in the displayed the at least the portion of the envelope, all regions of the greater-contact regions, which are associated with a same degree of transducer-to-tissue contact based on at least some of the plurality of contact signal sets, with a same visual characteristic of the first visual characteristic set. In some embodiments, the data processing device system may be configured at least by the program at least to cause the display device system to visually represent, in the displayed the at least the portion of the envelope, all regions of the lesser-contact regions, which are associated with a same degree of transducer-to-tissue contact based on at least some of the plurality of contact signal sets, with a same visual characteristic of the second visual characteristic set.

In some embodiments, the first visual characteristic set may be configured to visually indicate the greater-contact regions of the at least the portion of the envelope at least in part according to a first color set, and the second visual characteristic set may be configured to visually indicate the lesser-contact regions of the at least the portion of the envelope at least in part according to a second color set, the first color set mutually exclusive with the second color set. In some embodiments, each color in the first color set may have a different hue than each color in the second color set. In some embodiments, each color in the first color set may have a different lightness than each color in the second color set. In some embodiments, each color in the first color set may have a different saturation. In some embodiments, each color in the first color set may have a different lightness.

In some embodiments, the first visual characteristic set and the second visual characteristic set may be configured to cause the greater-contact regions of the at least the portion of the envelope to visually appear less transparent than at least one particular lesser-contact region of the lesser-contact regions of the at least the portion of the envelope. In some embodiments, the at least one particular lesser-contact region of the lesser-contact regions of the at least the portion of the envelope may be associated with no transducer-to-tissue contact. In some embodiments, the second visual characteristic set may be configured to cause the at least one particular lesser-contact region of the at least the portion of the envelope to visually appear as fully transparent. In some embodiments, the at least one particular lesser-contact region of the lesser-contact regions of the at least the portion of the envelope may correspond to at least part of a port interrupting the tissue surface within the bodily cavity.

In some embodiments, the first visual characteristic set may be configured to visually distinguish at least two regions of the greater-contact regions of the at least the portion of the envelope, the at least two regions of the greater-contact regions of the at least the portion of the envelope indicating different degrees of transducer-to-tissue contact. In some embodiments, the second visual characteristic set may be configured to visually distinguish at least two regions of the lesser-contact regions of the at least the portion of the envelope, the at least two regions of the lesser-contact regions of the at least the portion of the envelope indicating different degrees of transducer-to-tissue contact.

In some embodiments, the data processing device system may be configured at least by the program at least to cause the display device system to visually locate a particular greater-contact region of the greater-contact regions in a first region of the at least the portion of the envelope, the first region of the at least the portion of the envelope corresponding to a first particular location in the sequence of locations in the bodily cavity The data processing device system may be configured at least by the program at least to cause the display device system to visually indicate the particular greater-contact region according to the first visual characteristic set in the first region of the at least the portion of the envelope in a state representative of the at least the portion of the catheter being located at a second particular location in the sequence of locations in the bodily cavity, the second particular location subsequent to the first particular location in the sequence of locations. In some embodiments, the data processing device system may be configured at least by the program at least to cause, during the progressively visually representing in the progressively enlarging manner, the display device system to visually indicate an envelope enlargement, leading at least toward the visually represented at least the portion of the envelope, as visually adding a new tissue-contact region.

In some embodiments, at least a particular lesser-contact region of the lesser-contact regions is associated with no transducer-to-tissue contact, and the data processing device system may be configured at least by the program at least to receive a plurality of tissue-electrical-information signal sets from a second set of transducers of the plurality of transducers, the plurality of tissue-electrical-information signal sets indicating an electrical property set associated at least in part with a body including the bodily cavity and detected by the second set of transducers, and cause the display device system, based on at least some tissue-electrical-information signals of the plurality of tissue-electrical-information signal sets, to visually represent the at least the portion of the envelope in a manner that visually indicates at least a portion of the electrical property set in at least some of the greater-contact regions, but with no visual indication of the electrical property set in at least the particular lesser-contact region of the lesser-contact regions associated with no transducer-to-tissue contact. In some embodiments, the second set of transducers may be the first set of transducers. In some embodiments, the particular lesser-contact region of the lesser-contact regions may correspond to at least part of a port that interrupts the tissue surface within the bodily cavity. In some embodiments, the particular lesser-contact region of the lesser-contact regions may be surrounded by at least some of the greater-contact regions. In some embodiments, the data processing device system may be configured at least by the program at least to receive the plurality of tissue-electrical-information signal sets in a state representative of the second set of transducers of the plurality of transducers being located in the bodily cavity. In some embodiments, he data processing device system may be configured at least by the program at least to receive the plurality of tissue-electrical-information signal sets from the second set of transducers of the plurality of transducers throughout movement of at least the portion of the catheter among the sequence of locations of the at least the portion of the catheter in the bodily cavity.

In some embodiments, the input-output device system includes a catheter-device-location tracking system, and the data processing device system may be configured at least by the program at least to receive the plurality of location signal sets from the catheter-device-location tracking system. In some embodiments, the catheter-device-location tracking system may be configured to generate the plurality of location signal sets at least in response to one or more electric fields producible by one or more devices of the catheter-device-location tracking system. In some embodiments, the one or more devices of the catheter-device-location tracking system may be configured to operate outside a body comprising the bodily cavity. In some embodiments, the catheter-device-location tracking system may be configured to generate the plurality of location signal sets at least in response to one or more magnetic fields producible by one or more devices of the catheter-device-location tracking system. In some embodiments, the one or more devices of the catheter-device-location tracking system nay be configured to operate outside a body comprising the bodily cavity.

In some embodiments, the data processing device system may be configured at least by the program at least to cause the display device system to progressively visually represent, in the progressively enlarging manner and based on and throughout reception of at least the plurality of location signal sets and the plurality of contact signal sets, the at least the portion of the envelope. In some embodiments, the data processing device system may be configured at least by the program at least to generate an interpolated portion of the at least the portion of the envelope at least by determining interpolating tissue contact values based at least on an analysis of tissue contact values indicated by (i) a first contact signal set of the plurality of contact signal sets associated with a first portion of the at least the portion of the envelope, and (ii) a second contact signal set of the plurality of contact signal sets associated with a second portion of the at least the portion of the envelope. In some embodiments, the causing the display device system to visually represent, in the progressively enlarging manner, may include a display of the interpolated portion of the at least the portion of the envelope between the first portion of the at least the portion of the envelope and the second portion of the at least the portion of the envelope.

According to some embodiments, a method executed by a programmed data processing device system of a catheter navigation system may be summarized as including receiving a plurality of location signal sets, each location signal set of the plurality of location signal sets indicative of a respective location in a sequence of locations at which at least a portion of a catheter has been sequentially located in a bodily cavity, the catheter comprising a plurality of transducers. The method may include receiving a plurality of contact signal sets from a first set of transducers of the plurality of transducers, each transducer of at least the first set of transducers configured to detect transducer-to-tissue contact, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity. The method may include progressively visually representing in a progressively enlarging manner via a display device system communicatively connected to the programmed data processing device system, and based on and throughout reception of at least the plurality of location signal sets, at least a portion of an envelope, the envelope representing an interior volume of the bodily cavity. In some embodiments, the at least the portion of the envelope visually represented via the display device system may visually indicate, based on at least the plurality of contact signal sets, greater-contact regions of the at least the portion of the envelope associated with relatively greater transducer-to-tissue contact in accordance with a first visual characteristic set, and may visually indicate lesser-contact regions of the at least the portion of the envelope associated with relatively lesser transducer-to-tissue contact in accordance with a second visual characteristic set, the second visual characteristic set different than the first visual characteristic set.

According to some embodiments, one or more non-transitory computer-readable storage mediums storing a computer-executable program are provided. The program may include location signal set receiving instructions configured to cause reception of a plurality of location signal sets, each location signal set of the plurality of location signal sets indicative of a respective location in a sequence of locations at which at least a portion of a catheter has been sequentially located in a bodily cavity, the catheter comprising a plurality of transducers. The program may include contact signal set receiving instructions configured to cause reception of a plurality of contact signal sets from a first set of transducers of the plurality of transducers, each transducer of at least the first set of transducers configured to detect transducer-to-tissue contact, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity. The program may include visual representation instructions configured to cause a display device system to progressively visually represent, in a progressively enlarging manner and based on and throughout reception of at least the plurality of location signal sets, at least a portion of an envelope, the envelope representing an interior volume of the bodily cavity In some embodiments, the visual representation instructions may be configured to cause the display device system to cause the visually represented at least the portion of the envelope to visually indicate, based on at least the plurality of contact signal sets, greater-contact regions of the at least the portion of the envelope associated with relatively greater transducer-to-tissue contact in accordance with a first visual characteristic set and to visually indicate lesser-contact regions of the at least of the portion of the envelope associated with relatively lesser transducer-to-tissue contact in accordance with a second visual characteristic set, the second visual characteristic set different than the first visual characteristic set.

According to some embodiments, a catheter navigation system may be summarized as including an input-output device system communicatively connected to a display device system, a memory device system storing a program, and a data processing device system communicatively connected to the input-output device system and the memory device system. In some embodiments, the data processing device system may be configured at least by the program at least to receive a plurality of location signal sets, each location signal set of the plurality of location signal sets indicative of a respective location in a sequence of locations at which at least a portion of a catheter has been sequentially located in a bodily cavity, the catheter comprising a plurality of transducers. In some embodiments, the data processing device system may be configured at least by the program at least to receive a plurality of contact signal sets from a first set of transducers of the plurality of transducers, each transducer of at least the first set of transducers configured to detect transducer-to-tissue contact, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity. In some embodiments, the data processing device system may be configured at least by the program at least to cause the display device system to progressively visually represent, in a progressively enlarging manner and based on and throughout reception of at least the plurality of location signal sets, at least a portion of an envelope, the envelope representing an interior volume of the bodily cavity. In some embodiments, the data processing device system may be configured at least by the program at least to cause, during the progressively visually representing in the progressively enlarging manner, the display device system to visually indicate each envelope enlargement, leading to the visually represented at least the portion of the envelope, as visually including (a) at least one tissue-contact region, or (b) at least one no-tissue-contact region, or both (a) and (b), such that the visually represented at least the portion of the envelope visually distinguishes one or more tissue-contact regions from one or more no-tissue-contact regions, each tissue-contact region of the one or more tissue-contact regions associated with transducer-to-tissue contact according to at least a particular contact signal set of the plurality of contact signal sets, and each no-tissue-contact region of the one or more no-tissue-contact regions associated with no transducer-to-tissue contact according to at least a particular contact signal set of the plurality of contact signal sets.

In some embodiments, the data processing device system may be configured at least by the program at least to cause the display device system to visually represent in the at least the portion of the envelope a particular no-tissue-contact region of the one or more no-tissue-contact regions surrounded by at least one of the one or more tissue-contact regions. In some embodiments, the data processing device system may be configured at least by the program at least to cause the display device system to visually represent in the at least the portion of the envelope a particular no-tissue-contact region of the one or more no-tissue-contact regions as enclosed by at least one of the one or more tissue-contact regions. In some embodiments, the particular no-tissue-contact region of the one or more no-tissue-contact regions may correspond to at least part of a port that interrupts the tissue surface within the bodily cavity.

In some embodiments, the data processing device system may be configured at least by the program at least to cause, during the progressively visually representing in the progressively enlarging manner, a particular envelope enlargement to visually represent, via the display device system, one or more particular no-tissue-contact regions surrounded by one or more particular tissue-contact regions. In some embodiments, the one or more particular no-tissue-contact regions may correspond to at least part of one or more ports that interrupt the tissue surface within the bodily cavity.

In some embodiments, the data processing device system may be configured at least by the program at least to cause, during the progressively visually representing in the progressively enlarging manner, the display device system to display a first particular envelope enlargement accompanied by a display of a plurality of graphical elements, each graphical element of the plurality of graphical elements corresponding to a respective transducer of the at least the first set of transducers of the plurality of transducers, each graphical element of the plurality of graphical elements displayed in accordance with a visual characteristic set indicating the degree of transducer-to-tissue contact detected by the respective transducer of the at least the first set of transducers of the plurality of transducers, as indicated by one or more contact signals in one or more contact signal sets from the plurality of contact signal sets, and each graphical element of the plurality of graphical elements displayed in accordance with the visual characteristic set at least in a state representative of the at least the portion of the catheter being in a particular location in the sequence of locations associated with the first particular envelope enlargement. In some embodiments, the data processing device system may be configured at least by the program at least to cause the display device system to display (i) the plurality of graphical elements as superimposed with (ii) the first particular envelope enlargement. In some embodiments, at least the first set of transducers of the plurality of transducers is arrangeable in a first spatial distribution, and the data processing device system may be configured at least by the program at least to cause the displayed graphical elements of the plurality of graphical elements to be visually arranged by the display device system in a second distribution that is consistent with the first spatial distribution. In some embodiments, the data processing device system may be configured at least by the program at least to cause the display of each graphical element of the plurality of graphical elements displayed in accordance with the visual characteristic set at least in the state representative of the at least the portion of the catheter being in the particular location in the sequence of locations associated with the first particular envelope enlargement to visually represent, via the display device system, current degrees of transducer-to-tissue contact detected by the respective transducers of the at least the first set of transducers of the plurality of transducers according to a corresponding most recent contact signal set of the plurality of contact signal sets. In some embodiments, the data processing device system may be configured at least by the program at least to cause the display device system to display at least one region of the one or more tissue-contact regions of the at least the portion of the envelope to visually represent, via the display device system, previous degrees of transducer-to-tissue contact detected by at least some transducers of the first set of transducers of the plurality of transducers according to one or more corresponding not-most-recent contact signal sets of the plurality of contact signal sets.

In some embodiments, the displayed one or more tissue-contact regions may include a plurality of displayed tissue-contact regions. In some embodiments, the data processing device system may be configured at least by the program at least to cause the display device system to visually represent each displayed tissue-contact region of the plurality of displayed tissue-contact regions in accordance with a first visual characteristic set indicating a degree of transducer-to-tissue contact. In some embodiments, the processing device system may be configured at least by the program at least to cause the display device system to visually represent all regions of the plurality of displayed tissue-contact regions that are associated with a same degree of transducer-to-tissue contact with a same visual characteristic of the first visual characteristic set. In some embodiments, the one or more no-tissue-contact regions may include a plurality of no-tissue-contact regions. In some embodiments, the data processing device system may be configured at least by the program at least to cause the display device system to visually represent all regions of the plurality of no-tissue-contact regions with a same visual characteristic.

In some embodiments, the data processing device system may be configured at least by the program at least to cause the visually represented at least the portion of the envelope to visually indicate, via the display device system, the one or more tissue-contact regions according to a first color set. In some embodiments, the data processing device system may be configured at least by the program at least to cause the visually represented at least the portion of the envelope to visually indicate, via the display device system, the one or more no-tissue-contact regions according to a second color set mutually exclusive with the first color set. In some embodiments, each color in the first color set may have a different hue than each color in the second color set. In some embodiments, each color in the first color set may have a different lightness than each color in the second color set. In some embodiments, each color in the first color set may have a different saturation. In some embodiments, each color in the first color set may have a different lightness.

In some embodiments, the data processing device system may be configured at least by the program at least to cause, during the progressively visually representing in the progressively enlarging manner, a first particular envelope enlargement to visually represent, via the display device system, a particular tissue-contact region of the one or more tissue-contact regions according to a first color set. In some embodiments, the data processing device system may be configured at least by the program at least to cause, during the progressively visually representing in the progressively enlarging manner, a second particular envelope enlargement to visually represent, via the display device system, a particular no-tissue-contact region of the one or more no-tissue-contact regions according to a second color set mutually exclusive with the first color set. In some embodiments, the second particular envelope enlargement may be the first particular envelope enlargement.

In some embodiments, the data processing device system may be configured at least by the program at least to cause the visually represented at least the portion of the envelope to visually represent, via the display device system, each of the one or more tissue-contact regions as less transparent than each of the one or more no-tissue-contact regions.

In some embodiments, the data processing device system may be configured at least by the program at least to receive a plurality of tissue-electrical-information signal sets from a second set of transducers of the plurality of transducers, the plurality of tissue-electrical-information signal sets indicating an electrical property set associated at least in part with a body including the bodily cavity and detected by the second set of transducers, each tissue-electrical-information signal set of the plurality of tissue-electrical-information signal sets corresponding to a respective location in the sequence of locations of the at least the portion of the catheter in the bodily cavity. In some embodiments, the data processing device system may be configured at least by the program at least to cause, each envelope enlargement leading to the visually represented at least the portion of the envelope to visually indicate, via the display device system, at least a portion of the electrical property set in at least one tissue-contact region of the one or more tissue-contact regions, but with no visual indication of the electrical property set in any of the one or more no-tissue-contact regions. In some embodiments, at least one region of the one or more no-tissue-contact regions may correspond to at least part of a port that interrupts the tissue surface within the bodily cavity. In some embodiments, a particular no-tissue-contact region of the one or more no-tissue-contact regions may be surrounded by at least some of the one or more tissue-contact regions. In some embodiments, the data processing device system may be configured at least by the program at least to receive the plurality of tissue-electrical-information signal sets in a state representative of the second set of transducers of the plurality of transducers being located in the bodily cavity. In some embodiments, the data processing device system may be configured at least by the program at least to receive the plurality of tissue-electricalinformation signal sets from the second set of transducers of the plurality of transducers throughout movement of at least the portion of the catheter among the sequence of locations of the at least the portion of the catheter in the bodily cavity.

In some embodiments, the data processing device system may be configured at least by the program at least to cause the display device system to progressively visually represent, in the progressively enlarging manner and based on and throughout reception of at least the plurality of location signal sets and the plurality of contact signal sets, the at least the portion of the envelope.

In some embodiments, the input-output device system may include a catheter-device-location tracking system, and the data processing device system may be configured at least by the program at least to receive the plurality of location signal sets from the catheter-device-location tracking system. In some embodiments, the catheter-device-location tracking system may be configured to generate the plurality of location signal sets at least in response to one or more electric fields producible by one or more devices of the catheter-device-location tracking system. In some embodiments, the one or more devices of the catheter-device-location tracking system may be configured to operate outside a body comprising the bodily cavity. In some embodiments, the catheter-device-location tracking system may be configured to generate the plurality of location signal sets at least in response to one or more magnetic fields producible by one or more devices of the catheter-device-location tracking system. In some embodiments, the one or more devices of the catheter-device-location tracking system may be configured to operate outside a body comprising the bodily cavity.

According to some embodiments, a method executed by a programmed data processing device system of a catheter navigation system may include receiving a plurality of location signal sets, each location signal set of the plurality of location signal sets indicative of a respective location in a sequence of locations at which at least a portion of a catheter has been sequentially located in a bodily cavity, the catheter comprising a plurality of transducers. In some embodiments, the method may include receiving a plurality of contact signal sets from a first set of transducers of the plurality of transducers, each transducer of at least the first set of transducers configured to detect transducer-to-tissue contact, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity. In some embodiments, the method may include progressively visually representing in a progressively enlarging manner via a display device system communicatively connected to the programmed data processing device system, and based on and throughout reception of at least the plurality of location signal sets, at least a portion of an envelope, the envelope representing an interior volume of the bodily cavity. In some embodiments, during the progressively visually representing in the progressively enlarging manner, each envelope enlargement leading to the visually represented at least the portion of the envelope indicates, (a) at least one tissue-contact region, or (b) at least one no-tissue-contact region, or both (a) and (b), such that the visually represented at least the portion of the envelope visually distinguishes one or more tissue-contact regions from one or more no-tissue-contact regions, each tissue-contact region of the one or more tissue-contact regions associated with transducer-to-tissue contact according to at least a particular contact signal set of the plurality of contact signal sets, and each no-tissue-contact region of the one or more no-tissue-contact regions associated with no transducer-to-tissue contact according to at least a particular contact signal set of the plurality of contact signal sets.

According to some embodiments, one or more non-transitory computer-readable storage mediums storing a computer-executable program is provided. In some embodiments, the program may include location signal set receiving instructions configured to cause reception of a plurality of location signal sets, each location signal set of the plurality of location signal sets indicative of a respective location in a sequence of locations at which at least a portion of a catheter has been sequentially located in a bodily cavity, the catheter comprising a plurality of transducers. in some embodiments, the program may include contact signal set receiving instructions configured to cause reception of a plurality of contact signal sets from a first set of transducers of the plurality of transducers, each transducer of at least the first set of transducers configured to detect transducer-to-tissue contact, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity. In some embodiments, the program may include visual representation instructions configured to cause a display device system to progressively visually represent, in a progressively enlarging manner and based on and throughout reception of at least the plurality of location signal sets, at least a portion of an envelope, the envelope representing an interior volume of the bodily cavity. In some embodiments, the visual representation instructions may be configured to cause, during the progressively visually representing in the progressively enlarging manner, the display device system to visually indicate each envelope enlargement, leading to the visually represented at least the portion of the envelope, as visually including (a) at least one tissue-contact region, or (b) at least one no-tissue-contact region, or both (a) and (b), such that the visually represented at least the portion of the envelope visually distinguishes one or more tissue-contact regions from one or more no-tissue-contact regions, each tissue-contact region of the one or more tissue-contact regions associated with transducer-to-tissue contact according to at least a particular contact signal set of the plurality of contact signal sets, and each no-tissue-contact region of the one or more no-tissue-contact regions associated with no transducer-to-tissue contact according to at least a particular contact signal set of the plurality of contact signal sets.

According to some embodiments, a catheter navigation system may be summarized as including an input-output device system communicatively connected to a display device system, a memory device system storing a program, and a data processing device system communicatively connected to the input-output device system and the memory device system. In some embodiments, the data processing device system may be configured at least by the program at least to receive a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution, each transducer of the plurality of transducers configured to detect a degree of transducer-to-tissue contact. In some embodiments, the data processing device system may be configured at least by the program at least to generate and cause, at least in a state representative of the at least the portion of the catheter being in a particular location in the sequence of locations, the display device system to display a graphical representation, the graphical representation including a visual representation, in a graphically-overlapping manner, of at least (a) at least a portion of an envelope representing an interior volume of the bodily cavity, and (b) a plurality of graphical elements, the at least the portion of the envelope visually represented based at least on some location signals of the received plurality of location signal sets, the at least some location signals representing at least two locations in the sequence of locations of the at least the portion of the catheter in the bodily cavity, each graphical element of the plurality of graphical elements corresponding to a respective transducer of the plurality of transducers, and the graphical elements of the plurality of graphical elements arranged in a second distribution that is consistent with the first spatial distribution. In some embodiments, the graphical representation may include a display of at least a first graphical element in accordance with a first visual characteristic set indicating a first degree of transducer-to-tissue contact, the first graphical element from the plurality of graphical elements and located in a first region of the at least the portion of the envelope, and the first graphical element corresponding to a first transducer of the plurality of transducers detecting the first degree of transducer-to-tissue contact at least in the state representative of the at least the portion of the catheter being in the particular location in the sequence of locations. In some embodiments, the graphical representation may include a display of at least a second graphical element in accordance with a second visual characteristic set indicating a second degree of transducer-to-tissue contact, the second graphical element from the plurality of graphical elements and located in a second region of the at least the portion of the envelope, and the second graphical element corresponding to a second transducer of the plurality of transducers detecting the second degree of transducer-to-tissue contact at least in the state representative of the at least the portion of the catheter being in the particular location in the sequence of locations. In some embodiments, at least one difference between the first visual characteristic set and the second visual characteristic set indicates at least one difference between the first degree of transducer-to-tissue contact and the second degree of transducer-to-tissue contact.

In some embodiments, the data processing device system may be configured at least by the program at least to generate and cause the display device system to progressively visually represent in a progressively enlarging manner, and based on and throughout reception of at least the plurality of location signal sets, the at least the portion of the envelope.

In some embodiments, the first visual characteristic set may be configured to visually indicate relatively greater degree of transducer-to-tissue contact and the second visual characteristic set is configured to visually indicate a relatively lower degree of transducer-to-tissue contact. In some embodiments, the data processing device system may be configured at least by the program at least to cause all graphical elements of the plurality of graphical elements corresponding to respective ones of the plurality of transducers associated with a same degree of detected transducer-to-tissue contact to exhibit a same visual characteristic of a particular visual characteristic set. In some embodiments, the data processing device system may be configured at least by the program at least to cause, in the displayed graphical representation, all graphical elements of the plurality of graphical elements corresponding to respective ones of the plurality of transducers that are associated with the first degree of detected transducer-to-tissue contact to be displayed in accordance with the first visual characteristic set, and all graphical elements of the plurality of graphical elements corresponding to respective ones of the plurality of transducers that are associated with the second degree of detected transducer-to-tissue contact to be displayed in accordance with the second visual characteristic set.

In some embodiments, the first visual characteristic set may be configured to visually indicate relatively greater degree of transducer-to-tissue contact and the second visual characteristic set is configured to visually indicate a relatively lower degree of transducer-to-tissue contact. In some embodiments, the first visual characteristic set may be configured to visually indicate the relatively greater degree of transducer-to-tissue contact at least in part according to a first color set, and the second visual characteristic set may be configured to visually indicate the relatively lesser degree of transducer-to-tissue contact at least in part according to a second color set mutually exclusive with the first color set. In some embodiments, each color in the first color set may have a different hue than each color in the second color set. In some embodiments, each color in the first color set may have a different lightness than each color in the second color set. In some embodiments, each color in the first color set may have a different saturation. In some embodiments, each color in the first color set may have a different lightness. In some embodiments, the visual representation in the graphically-overlapping manner of at least (a) and (b) may include a blending of (i) a first color of at least a part of the first graphical element in the first color set with (ii) a second color of an overlapping region in the at least the portion of the envelope that overlaps the at least the part of the first graphical element. In some embodiments, the second color may indicate, on the overlapping region in the at least the portion of the envelope, a different degree of transducer-to-tissue contact than the first degree of transducer-to-tissue contact. In some embodiments, the second degree of transducer-to-tissue contact may be associated with no transducer-to-tissue contact.

In some embodiments, the data processing device system may be configured at least by the program at least to cause at least (a) and (b) to be displayed in a graphically-overlapping semi-transparent manner in the graphical representation. In some embodiments, the data processing device system may be configured at least by the program at least to receive, via the input-output device system, a plurality of tissue-electrical-information signal sets indicating an electrical property set associated at least in part with a body including the bodily cavity and detected by at least a set of transducers of the plurality of transducers. In some embodiments, the data processing device system may be configured at least by the program at least to cause the graphical representation to include a visual representation, on at least a part of the envelope, of at least a portion of the electrical property set while the graphical representation includes the visual representation, in the graphically-overlapping manner, of at least (a) at least the portion of the envelope and (b) the plurality of graphical elements, with the graphical representation including the display of the at least the first graphical element in accordance with the first visual characteristic set indicating the first degree of transducer-to-tissue contact, and with the graphical representation including the display of the at least the second graphical element in accordance with the second visual characteristic set indicating the second degree of transducer-to-tissue contact. In some embodiments, the at least the portion of the electrical property set is an electrical potential of a tissue surface of the bodily cavity.

In some embodiments, the input-output device system may include a catheter-device-location tracking system, and the data processing device system may be configured at least by the program at least to receive the plurality of location signal sets from the catheter-device-location tracking system. In some embodiments, the catheter-device-location tracking system may be configured to generate the plurality of location signal sets at least in response to one or more electric fields producible by one or more devices of the catheter-device-location tracking system. In some embodiments, the one or more devices of the catheter-device-location tracking system may be configured to operate outside a body comprising the bodily cavity. In some embodiments, the catheter-device-location tracking system may be configured to generate the plurality of location signal sets at least in response to one or more magnetic fields producible by one or more devices of the catheter-device-location tracking system. In some embodiments, the one or more devices of the catheter-device-location tracking system may be configured to operate outside a body comprising the bodily cavity.

According to some embodiments, a method executed by a programmed data processing device system of a catheter navigation system may include receiving a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution, each transducer of the plurality of transducers configured to detect a degree of transducer-to-tissue contact. In some embodiments, the method may include generating and causing, at least in a state representative of the at least the portion of the catheter being in a particular location in the sequence of locations, a display device system communicatively connected to the programmed data processing device system to display a graphical representation, the graphical representation including a visual representation, in a graphically-overlapping manner, of at least (a) at least a portion of an envelope representing an interior volume of the bodily cavity, and (b) a plurality of graphical elements, the at least the portion of the envelope visually represented based at least on some location signals of the received plurality of location signal sets, the at least some location signals representing at least two locations in the sequence of locations of the at least the portion of the catheter in the bodily cavity, each graphical element of the plurality of graphical elements corresponding to a respective transducer of the plurality of transducers, and the graphical elements of the plurality of graphical elements arranged in a second distribution that is consistent with the first spatial distribution. In some embodiments, the graphical representation may include a display of at least a first graphical element in accordance with a first visual characteristic set indicating a first degree of transducer-to-tissue contact, the first graphical element from the plurality of graphical elements and located in a first region of the at least the portion of the envelope, and the first graphical element corresponding to a first transducer of the plurality of transducers detecting the first degree of transducer-to-tissue contact at least in the state representative of the at least the portion of the catheter being in the particular location in the sequence of locations. In some embodiments, the graphical representation may include a display of at least a second graphical element in accordance with a second visual characteristic set indicating a second degree of transducer-to-tissue contact, the second graphical element from the plurality of graphical elements and located in a second region of the at least the portion of the envelope, and the second graphical element corresponding to a second transducer of the plurality of transducers detecting the second degree of transducer-to-tissue contact at least in the state representative of the at least the portion of the catheter being in the particular location in the sequence of locations. In some embodiments, at least one difference between the first visual characteristic set and the second visual characteristic set may indicate at least one difference between the first degree of transducer-to-tissue contact and the second degree of transducer-to-tissue contact.

According to some embodiments, one or more non-transitory computer-readable storage mediums storing a computer-executable program. In some embodiments, the program may include location-signal-set-receiving instructions configured to cause reception of a plurality of location signal sets, each location signal set of the plurality of location signal sets indicative of a respective location in a sequence of locations at which at least a portion of a catheter has been sequentially located in a bodily cavity, the catheter comprising a plurality of transducers arrangeable in a first spatial distribution, each transducer of the plurality of transducers configured to detect a degree of transducer-to-tissue contact. In some embodiments, the program may include graphical representation instructions configured to cause generation and display, via a display device system and at least in a state representative of the at least the portion of the catheter being in a particular location in the sequence of locations, of a graphical representation, the graphical representation including a visual representation, in a graphically-overlapping manner, of at least (a) at least a portion of an envelope representing an interior volume of the bodily cavity, and (b) a plurality of graphical elements, the at least the portion of the envelope visually represented based at least on some location signals of the received plurality of location signal sets, the at least some location signals representing at least two locations in the sequence of locations of the at least the portion of the catheter in the bodily cavity, each graphical element of the plurality of graphical elements corresponding to a respective transducer of the plurality of transducers, and the graphical elements of the plurality of graphical elements arranged in a second distribution that is consistent with the first spatial distribution. In some embodiments, the graphical representation may include a display of at least a first graphical element in accordance with a first visual characteristic set indicating a first degree of transducer-to-tissue contact, the first graphical element from the plurality of graphical elements and located in a first region of the at least the portion of the envelope, and the first graphical element corresponding to a first transducer of the plurality of transducers detecting the first degree of transducer-to-tissue contact at least in the state representative of the at least the portion of the catheter being in the particular location in the sequence of locations. In some embodiments, the graphical representation may include a display of at least a second graphical element in accordance with a second visual characteristic set indicating a second degree of transducer-to-tissue contact, the second graphical element from the plurality of graphical elements and located in a second region of the at least the portion of the envelope, and the second graphical element corresponding to a second transducer of the plurality of transducers detecting the second degree of transducer-to-tissue contact at least in the state representative of the at least the portion of the catheter being in the particular location in the sequence of locations. In some embodiments, at least one difference between the first visual characteristic set and the second visual characteristic set may indicate at least one difference between the first degree of transducer-to-tissue contact and the second degree of transducer-to-tissue contact.

According to some embodiments, a catheter navigation system may be summarized as including an input-output device system communicatively connected to a display device system, a memory device system storing a program, and a data processing device system communicatively connected to the input-output device system and the memory device system. In some embodiments, the data processing device system may be configured at least by the program at least to receive a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution, each transducer of the plurality of transducers configured to detect a degree of transducer-to-tissue contact. In some embodiments, the data processing device system may be configured at least by the program at least to generate and cause, at least in a state representative of the at least the portion of the catheter being in a particular location in the sequence of locations, the display device system to display a graphical representation, the graphical representation including a visual representation, in a graphically-overlapping manner, of at least (a) at least a portion of an envelope representing an interior volume of the bodily cavity, and (b) a plurality of graphical elements, the at least the portion of the envelope visually represented based at least on some location signals of the received plurality of location signal sets representing the sequence of locations of the at least the portion of the catheter in the bodily cavity, each graphical element of the plurality of graphical elements corresponding to a respective transducer of the plurality of transducers, and the graphical elements of the plurality of graphical elements arranged in a second distribution that is consistent with the first spatial distribution. In some embodiments, the graphical representation may include a display of at least a first graphical element in accordance with a first visual characteristic set indicating a first degree of an electrical property, the first graphical element from the plurality of graphical elements and located in a first region of the at least the portion of the envelope, and the first graphical element corresponding to a first transducer of the plurality of transducers detecting the first degree of the electrical property at least in the state representative of the at least the portion of the catheter being in the particular location in the sequence of locations. In some embodiments, the graphical representation may include a display of a second region of the at least the portion of the envelope in accordance with a second visual characteristic set indicating a second degree of the electrical property detected by one or more transducers of the plurality of transducers.

According to some embodiments, a catheter navigation system may be summarized as including an input-output device system communicatively connected to a display device system, a memory device system storing a program, and a data processing device system communicatively connected to the input-output device system and the memory device system. In some embodiments, the data processing device system may be configured at least by the program at least to receive a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution, each transducer of the plurality of transducers configured to detect a degree of transducer-to-tissue contact. In some embodiments, the data processing device system may be configured at least by the program at least to generate and cause, at least in a state representative of the at least the portion of the catheter being in a particular location in the sequence of locations, the display device system to display a graphical representation, the graphical representation including a visual representation, in a graphically-overlapping manner, of at least (a) at least a portion of an envelope representing an interior volume of the bodily cavity, and (b) a plurality of graphical elements, the at least the portion of the envelope visually represented based at least on some location signals of the received plurality of location signal sets representing the sequence of locations of the at least the portion of the catheter in the bodily cavity, each graphical element of the plurality of graphical elements corresponding to a respective transducer of the plurality of transducers, and the graphical elements of the plurality of graphical elements arranged in a second distribution that is consistent with the first spatial distribution. In some embodiments, the graphical representation may include a display of at least a first graphical element in accordance with a first visual characteristic set indicating a first property associated with tissue of the bodily cavity, the first graphical element from the plurality of graphical elements and located in a first region of the at least the portion of the envelope, and the first graphical element corresponding to a first transducer of the plurality of transducers detecting the first property associated with tissue of the bodily cavity at least in the state representative of the at least the portion of the catheter being in the particular location in the sequence of locations. In some embodiments, the graphical representation may include a display of a second region of the at least the portion of the envelope in accordance with a second visual characteristic set indicating a second property associated with tissue of the bodily cavity detected by one or more transducers of the plurality of transducers, the second property different in type than the first property.

According to some embodiments, a catheter navigation system may be summarized as including an input-output device system communicatively connected to a display device system, a memory device system storing a program, and a data processing device system communicatively connected to the input-output device system and the memory device system. In some embodiments, the data processing device system may be configured at least by the program at least to receive a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution. In some embodiments, the data processing device system may be configured at least by the program at least to receive a plurality of contact signal sets from a first set of transducers of the plurality of transducers, each transducer of at least the first set of transducers configured to detect transducer-to-tissue contact, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity. In some embodiments, the data processing device system may be configured at least by the program at least to generate and cause, at least in a state representative of the at least the portion of the catheter being in a particular location in the sequence of locations, the display device system to display a graphical representation, the graphical representation including a visual representation, in a graphically-overlapping manner, of at least (a) at least a portion of an envelope representing an interior volume of the bodily cavity, and (b) a plurality of graphical elements, the at least the portion of the envelope visually represented based at least on some location signals of the received plurality of location signal sets, the at least some location signals representing at least two locations in the sequence of locations of the at least the portion of the catheter in the bodily cavity, each graphical element of the plurality of graphical elements corresponding to a respective transducer of the plurality of transducers, and the graphical elements of the plurality of graphical elements arranged in a second distribution that is consistent with the first spatial distribution. In some embodiments, the graphical representation may include a display of at least a first graphical element in accordance with a first visual characteristic set indicating a first degree of transducer-to-tissue contact, the first graphical element from the plurality of graphical elements and corresponding to a first transducer of the plurality of transducers detecting the first degree of transducer-to-tissue contact at least in the state representative of the at least the portion of the catheter being in the particular location in the sequence of locations. In some embodiments, the graphical representation may include a display of a region of the at least the portion of the envelope in accordance with a second visual characteristic set indicating the first degree of transducer-to-tissue contact detected by one or more transducers of the plurality of transducers, the second visual characteristic set different than the first visual characteristic set.

In some embodiments, the first degree of transducer-to-tissue contact may be no-detected tissue contact. In some embodiments, the first visual characteristic set may be configured to visually indicate the no-detected tissue contact according to a first color set, and the second visual characteristic set may be configured to visually indicate the no-detected tissue contact according to a second color set, the first color set mutually exclusive with the second color set. In some embodiments, the first color set may be a first color, and the second color set may be a second color different than the first color.

According to some embodiments, a catheter navigation system may be summarized as including an input-output device system communicatively connected to a display device system, a memory device system storing a program, and a data processing device system communicatively connected to the input-output device system and the memory device system. In some embodiments, the data processing device system configured at least by the program at least to receive a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution. In some embodiments, the data processing device system configured at least by the program at least to generate and cause the display device system to progressively visually represent in a progressively enlarging manner, and based on and throughout reception of at least the received plurality of location signal sets, at least a portion of an envelope representing an interior volume of the bodily cavity. In some embodiments, the data processing device system configured at least by the program at least to cause the display device system to concurrently display at least (a) the at least the portion of the envelope, and (b) a plurality of graphical elements, each graphical element corresponding to a transducer of the plurality of transducers. In some embodiments, the causing the display device system to concurrently display at least (a) and (b) may include a display of a first set of graphical elements of the plurality of graphical elements and a region of the at least the portion of the envelope in a first graphically-overlapping manner, and with a second set of graphical elements of the plurality of graphical elements displayed in a second graphical manner indicating a view of the second set of graphical elements through a port-region in the at least the portion of the envelope corresponding to a port into the bodily cavity, the plurality of graphical elements graphically displayed in a second distribution corresponding to the first spatial distribution.

In some embodiments, the first graphically-overlapping manner may include a blending of (i) a first color of at least a part of a first graphical element of the first set of graphical elements with (ii) a second color of an overlapping region in the region of the at least the portion of the envelope that overlaps the at least the part of the first graphical element. In some embodiments, the second graphical manner may include a transparent graphical representation of the port-region in the at least the portion of the envelope, which allows the second set of graphical elements to be viewable in a graphically unobstructed manner. In some embodiments, the second graphical manner may include a semi-transparent graphical representation of the port-region in the at least the portion of the envelope, causing one or more colors of the second set of graphical elements to be blended with one or more colors of the port-region in the at least the portion of the envelope.

In some embodiments, the first graphically-overlapping manner may include a graphical representation of the region of the at least the portion of the envelope in a first semi-transparent manner, causing one or more colors of the first set of graphical elements to be blended with one or more colors of the region in the at least the portion of the envelope. In some embodiments, the second graphical manner may include a graphical representation of the port-region in the at least the portion of the envelope in a second semi-transparent manner, causing one or more colors of the second set of graphical elements to be blended with one or more colors of the port-region in the at least the portion of the envelope. In some embodiments, the first semi-transparent manner may represent the region of the at least the portion of the envelope as less transparent than the second semi-transparent manner representing the port-region in the at least the portion of the envelope.

In some embodiments, the second graphical manner may include a graphical representation of the second set of graphical elements through the port-region in the at least the portion of the envelope without a blending of any colors associated with the port-region in the at least the portion of the envelope. In some embodiments, the second graphical manner may include a graphical representation of the port-region in the at least the portion of the envelope as an opening in the at least the portion of the envelope. In some embodiments, the data processing device system may be configured at least by the program at least to cause the display device system to concurrently display at least (a) the at least the portion of the envelope, (b) the plurality of graphical elements, and (c) a pre-existing image of the bodily cavity.

In some embodiments, the data processing device system may be configured at least by the program at least to cause the display device system to concurrently display at least (a) the at least the portion of the envelope, (b) the plurality of graphical elements, and (c) a pre-existing image of the bodily cavity. In some embodiments, the data processing device system may be configured at least by the program at least to cause the display device system to concurrently display at least (a) the at least the portion of the envelope, (b) the plurality of graphical elements, or both (a) and (b) in a graphically overlapping manner with at least a portion of (c) the pre-existing image of the bodily cavity. In some embodiments, the data processing device system may be configured at least by the program at least to cause the display device system to concurrently display at least a first part of the at least the portion of the envelope in a graphically-overlapping manner with a first portion of the pre-existing image of the bodily cavity, while concurrently displaying a second portion of the pre-existing image of the bodily cavity in a graphically-overlapping manner with at least a second part of the at least the portion of the envelope.

In some embodiments, the input-output device system may include a catheter-device-location tracking system, and the data processing device system may be configured at least by the program at least to receive the plurality of location signal sets from the catheter-device-location tracking system. In some embodiments, the catheter-device-location tracking system may be configured to generate the plurality of location signal sets at least in response to one or more electric fields producible by one or more devices of the catheter-device-location tracking system. In some embodiments, the one or more devices of the catheter-device-location tracking system may be configured to operate outside a body comprising the bodily cavity. In some embodiments, the catheter-device-location tracking system may be configured to generate the plurality of location signal sets at least in response to one or more magnetic fields producible by one or more devices of the catheter-device-location tracking system. In some embodiments, the one or more devices of the catheter-device-location tracking system may be configured to operate outside a body comprising the bodily cavity.

According to some embodiments, a method executed by a programmed data processing device system of a catheter navigation system may include receiving a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution. In some embodiments, the method may include generating and causing a display device system communicatively connected to the programmed data processing device system to progressively visually represent in a progressively enlarging manner, and based on and throughout reception of at least the received plurality of location signal sets, at least a portion of an envelope representing an interior volume of the bodily cavity. In some embodiments, the method may include causing the display device system to concurrently display at least (a) the at least the portion of the envelope, and (b) a plurality of graphical elements, each graphical element corresponding to a transducer of the plurality of transducers. In some embodiments, the causing the display device system to concurrently display at least (a) and (b) may include a display of a first set of graphical elements of the plurality of graphical elements and a region of the at least the portion of the envelope in a first graphically-overlapping manner, and with a second set of graphical elements of the plurality of graphical elements displayed in a second graphical manner indicating a view of the second set of graphical elements through a port-region in the at least the portion of the envelope corresponding to a port into the bodily cavity, the plurality of graphical elements graphically displayed in a second distribution consistent with the first spatial distribution.

According to some embodiments, one or more non-transitory computer-readable storage mediums storing a computer-executable program may be provided, the program including location signal set receiving instructions configured to cause reception of a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution. In some embodiments, the program may include graphical representation instructions configured to cause generation and progressive visual representation, in a progressively enlarging manner and based on and throughout reception of at least the received plurality of location signal sets, of at least a portion of an envelope representing an interior volume of the bodily cavity. In some embodiments, the program may include concurrent display instructions configured to cause the display device system to concurrently display at least (a) the at least the portion of the envelope, and (b) a plurality of graphical elements, each graphical element corresponding to a transducer of the plurality of transducers. In some embodiments the concurrent display instructions may be configured to cause the display device system to concurrently display at least (a) and (b) as including a display of a first set of graphical elements of the plurality of graphical elements and a region of the at least the portion of the envelope in a first graphically-overlapping manner, and with a second set of graphical elements of the plurality of graphical elements displayed in a second graphical manner indicating a view of the second set of graphical elements through a port-region in the at least the portion of the envelope corresponding to a port into the bodily cavity, the plurality of graphical elements graphically displayed in a second distribution consistent with the first spatial distribution.

According to some embodiments, a catheter navigation system may be summarized as including an input-output device system communicatively connected to a display device system, a memory device system storing a program, and a data processing device system communicatively connected to the input-output device system and the memory device system. In some embodiments, the data processing device system may be configured at least by the program at least to receive a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution, each transducer of the plurality of transducers configured to detect a degree of transducer-to-tissue contact. In some embodiments, the data processing device system may be configured at least by the program at least to generate and cause the display device system to concurrently display, in a state representative of the at least the portion of the catheter being in a particular location in the sequence of locations, at least (a) at least a portion of an envelope representing an interior volume of the bodily cavity based at least on the received plurality of location signal sets, and (b) a plurality of graphical elements, each graphical element corresponding to a transducer of the plurality of transducers. In some embodiments, the generating and causing the display device system to concurrently display at least (a) and (b) may include, in the state representative of the at least the portion of the catheter being in the particular location in the sequence of locations, a display of a first set of graphical elements of the plurality of graphical elements and a first portion of the at least the portion of the envelope in a graphically-overlapping manner, concurrently with a second portion of the at least the portion of the envelope displayed without overlapping or being overlapped by any of the graphical elements and in accordance with a particular visual characteristic set indicative of a degree-of-tissue-contact detected, in a prior state representative of the at least the portion of the catheter being in an earlier location in the sequence of locations, by a particular set of transducers of the plurality of transducers, the earlier location being earlier in the sequence of locations than the particular location in the sequence of locations. In some embodiments, the data processing device system may be configured at least by the program at least to cause the plurality of graphical elements to be graphically displayed, in the state representative of the at least the portion of the catheter being in the particular location in the sequence of locations, in a second distribution consistent with the first spatial distribution. In some embodiments, the first portion of the at least the portion of the envelope may be mutually exclusive with the second portion of the at least the portion of the envelope.

In some embodiments, the data processing device system may be configured at least by the program at least to receive a plurality of contact signal sets from a first set of transducers of the plurality of transducers, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity. In some embodiments, the data processing device system may be configured at least by the program at least to generate an interpolated portion of the at least the portion of the envelope at least by determining interpolating tissue contact values based at least on an analysis of tissue contact values indicated by (i) a first contact signal set of the plurality of contact signal sets associated with the first portion of the at least the portion of the envelope, and (ii) a second contact signal set of the plurality of contact signal sets associated with the second portion of the at least the portion of the envelope. In some embodiments, the generating and causing the display device system to concurrently display at least (a) and (b) may include, in the state representative of the at least the portion of the catheter being in the particular location in the sequence of locations, a display of the interpolated portion of the at least the portion of the envelope between the first portion of the at least the portion of the envelope and the second portion of the at least the portion of the envelope.

In some embodiments, the data processing device system may be configured at least by the program at least to cause all graphical elements of the first set of graphical elements corresponding to respective ones of the plurality of transducers associated with a same degree of detected transducer-to-tissue contact to exhibit a same visual characteristic indicating the same degree of transducer-to-tissue contact. In some embodiments, the data processing device system may be configured at least by the program at least to cause graphical elements of the first set of graphical elements corresponding to respective ones of the plurality of transducers associated with different degrees of detected transducer-to-tissue contact to exhibit different visual characteristics indicating the different degrees of detected transducer-to-tissue contact. In some embodiments, the particular visual characteristic set, which is associated with visually representing transducer-to-tissue contact via the second portion of the at least the portion of the envelope, may be a first particular visual characteristic set, and the different visual characteristics, which indicate the different degrees of detected transducer-to-tissue contact via the graphical elements of the first set of graphical elements corresponding to the respective ones of the plurality of transducers associated with the different degrees of detected transducer-to-tissue contact, may belong to a second particular visual characteristic set, and the first particular visual characteristic set and the second particular visual characteristic set may represent a same degree of transducer-to-tissue contact with a same color. In some embodiments, the particular visual characteristic set, which is associated with visually representing transducer-to-tissue contact via the second portion of the at least the portion of the envelope, may be a first particular visual characteristic set, and the different visual characteristics, which indicate the different degrees of detected transducer-to-tissue contact via the graphical elements of the first set of graphical elements corresponding to the respective ones of the plurality of transducers associated with the different degrees of detected transducer-to-tissue contact, may belong to a second particular visual characteristic set, and the first particular visual characteristic set and the second particular visual characteristic set may represent a same degree of transducer-to-tissue contact with different colors.

In some embodiments, the first set of graphical elements may include a first graphical element, and the display of the first set of graphical elements of the plurality of graphical elements and the first portion of the at least the portion of the envelope in the graphically-overlapping manner may include a blending of (i) a first color of at least a part of the first graphical element with (ii) a second color of an overlapping region in the at least the first portion of the at least the portion of the envelope that overlaps the at least the part of the first graphical element.

In some embodiments, the data processing device system may be configured at least by the program at least to receive a plurality of contact signal sets from a first set of transducers of the plurality of transducers, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity. In some embodiments, the data processing device system may be configured at least by the program at least to receive a plurality of tissue-electrical-information signal sets from a second set of transducers of the plurality of transducers, the plurality of tissue-electrical-information signal sets indicating an electrical property set associated at least in part with a body including the bodily cavity and detected by the second set of transducers. In some embodiments, the data processing device system may be configured at least by the program at least to cause the display device system, based at least on some tissue-electrical-information signals of the plurality of tissue-electrical-information signal sets, to visually represent the at least the portion of the envelope in a manner that visually indicates at least a portion of the electrical property set in at least some greater-contact regions of the at least the portion of the envelope, but with no visual indication of the electrical property set in at least a no-tissue-contact region of the at least the portion of the envelope, the greater-contact regions associated with transducer-to-tissue contact and the no-tissue-contact region associated with no transducer-to-tissue contact via the at least some contact signals of the plurality of contact signal sets. In some embodiments, the at least some greater-contact regions and the no-tissue-contact region may be in the first portion of the at least the portion of the envelope. In some embodiments, the at least some greater-contact regions and the no-tissue-contact region may be in the second portion of the at least the portion of the envelope. In some embodiments, at least one greater-contact region of the at least some greater-contact regions may be in the first portion of the at least the portion of the envelope, and a no-tissue-contact region may be in the second portion of the at least the portion of the envelope. In some embodiments, the second set of transducers may be the first set of transducers. In some embodiments, the no-tissue-contact region may correspond to at least part of a port that interrupts the tissue surface within the bodily cavity. In some embodiments, the no-tissue-contact region may be surrounded by at least some of the greater-contact regions.

In some embodiments, the data processing device system may be configured at least by the program at least to receive a first contact signal set from a first set of transducers of the plurality of transducers, the first set of transducers respectively corresponding to the first set of graphical elements, the first contact signal set indicating a degree of transducer-to-tissue contact between each transducer of the first set of transducers and a tissue surface within the bodily cavity, and the first contact signal set corresponding to the particular location in the sequence of locations of the at least the portion of the catheter in the bodily cavity. In some embodiments, the data processing device system may be configured at least by the program at least to cause the display device system to display, in the state representative of the at least the portion of the catheter being in the particular location in the sequence of locations and based at least on the received first contact signal set, each graphical element in the first set of graphical elements in accordance with a first visual characteristic set indicating a degree of transducer-to-tissue contact detected by the respective transducer of the at least the first set of transducers of the plurality of transducers. In some embodiments, the data processing device system may be configured at least by the program at least to receive a second contact signal set from a second set of transducers of the plurality of transducers, the second contact signal set indicating a degree of transducer-to-tissue contact between each transducer of the second set of transducers and the tissue surface within the bodily cavity in the prior state representative of the at least the portion of the catheter being in the earlier location in the sequence of locations. In some embodiments, the data processing device system may be configured at least by the program at least to cause the display device system to display, in the state representative of the at least the portion of the catheter being in the particular location in the sequence of locations and based at least on the received second contact signal set, the second portion of the at least the portion of the envelope displayed without overlapping or being overlapped by any of the graphical elements and with the particular visual characteristic set indicative of the degree-of-tissue-contact detected, in the prior state representative of the at least the portion of the catheter being in the earlier location in the sequence of locations, by the particular set of transducers of the plurality of transducers.

In some embodiments, the input-output device system may include a catheter-device-location tracking system, and the data processing device system may be configured at least by the program at least to receive the plurality of location signal sets from the catheter-device-location tracking system. In some embodiments, the catheter-device-location tracking system may be configured to generate the plurality of location signal sets at least in response to one or more electric fields producible by one or more devices of the catheter-device-location tracking system. In some embodiments, the one or more devices of the catheter-device-location tracking system may be configured to operate outside a body comprising the bodily cavity. In some embodiments, the catheter-device-location tracking system may be configured to generate the plurality of location signal sets at least in response to one or more magnetic fields producible by one or more devices of the catheter-device-location tracking system. In some embodiments, the one or more devices of the catheter-device-location tracking system may be configured to operate outside a body comprising the bodily cavity.

According to some embodiments, a method executed by a programmed data processing device system of a catheter navigation system may include receiving a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution, each transducer of the plurality of transducers configured to detect a degree of transducer-to-tissue contact. In some embodiments, the method may include generating and causing a display device system communicatively connected to the programmed data processing device system to concurrently display, in a state representative of the at least the portion of the catheter being in a particular location in the sequence of locations, at least (a) at least a portion of an envelope representing an interior volume of the bodily cavity based at least on the received plurality of location signal sets, and (b) a plurality of graphical elements, each graphical element corresponding to a transducer of the plurality of transducers. In some embodiments, the generating and causing the display device system to concurrently display at least (a) and (b) may include, in the state representative of the at least the portion of the catheter being in the particular location in the sequence of locations, a display of a first set of graphical elements of the plurality of graphical elements and a first portion of the at least the portion of the envelope in a graphically-overlapping manner, concurrently with a second portion of the at least the portion of the envelope displayed without overlapping or being overlapped by any of the graphical elements and in accordance with a particular visual characteristic set indicative of a degree-of-tissue-contact detected, in a prior state representative of the at least the portion of the catheter being in an earlier location in the sequence of locations, by a particular set of transducers of the plurality of transducers, the earlier location being earlier in the sequence of locations than the particular location in the sequence of locations. In some embodiments, the plurality of graphical elements may be graphically displayed, in the state representative of the at least the portion of the catheter being in the particular location in the sequence of locations, in a second distribution corresponding to the first spatial distribution. In some embodiments, the first portion of the at least the portion of the envelope may be mutually exclusive with the second portion of the at least the portion of the envelope.

According to some embodiments, one or more non-transitory computer-readable storage mediums storing a computer-executable program are provided. In some embodiments, the program may include location signal set receiving instructions configured to cause reception of a plurality of location signal sets, each location signal set of the plurality of location signal sets indicative of a respective location in a sequence of locations at which at least a portion of a catheter has been sequentially located in a bodily cavity, the catheter including a plurality of transducers arrangeable in a first spatial distribution, each transducer of the plurality of transducers configured to detect a degree of transducer-to-tissue contact. In some embodiments, the program may include concurrent display instructions configured to generate and cause the display device system to concurrently display, in a state representative of the at least the portion of the catheter being in a particular location in the sequence of locations, at least (a) at least a portion of an envelope representing an interior volume of the bodily cavity based at least on the received plurality of location signal sets, and (b) a plurality of graphical elements, each graphical element corresponding to a transducer of the plurality of transducers. In some embodiments, the concurrent display instructions may be configured to cause the display device system to concurrently display at least (a) and (b) as including, in the state representative of the at least the portion of the catheter being in the particular location in the sequence of locations, a display of a first set of graphical elements of the plurality of graphical elements and a first portion of the at least the portion of the envelope in a graphically-overlapping manner, concurrently with a second portion of the at least the portion of the envelope displayed without overlapping or being overlapped by any of the graphical elements and in accordance with a particular visual characteristic set indicative of a degree-of-tissue-contact detected, in a prior state representative of the at least the portion of the catheter being in an earlier location in the sequence of locations, by a particular set of transducers of the plurality of transducers, the earlier location being earlier in the sequence of locations than the particular location in the sequence of locations. In some embodiments, the program may include graphical element display instructions configured to cause the display device system to graphically display the plurality of graphical elements, in the state representative of the at least the portion of the catheter being in the particular location in the sequence of locations, in a second distribution consistent with the first spatial distribution. In some embodiments, the first portion of the at least the portion of the envelope may be mutually exclusive with the second portion of the at least the portion of the envelope.

According to some embodiments, a catheter navigation system may be summarized as including an input-output device system communicatively connected to a display device system, a memory device system storing a program, and a data processing device system communicatively connected to the input-output device system and the memory device system. According to some embodiments, the data processing device system may be configured at least by the program at least to receive a plurality of location signal sets, each location signal set of the plurality of location signal sets indicative of a respective location in a sequence of locations at which at least a portion of a catheter has been sequentially located in a bodily cavity, the catheter comprising a first transducer set and a second transducer set, each transducer in the first transducer set configured to detect a first property at least in a state in which the at least the portion of the catheter is located within the bodily cavity, and each transducer in the second transducer set configured to detect a second property at least in the state in which the at least the portion of the catheter is located within the bodily cavity, the first property different in type than the second property. According to some embodiments, the data processing device system may be configured at least by the program to cause, at least in a state representative of the at least the portion of the catheter being in a particular location in the sequence of locations, the display device system to display a graphical representation, the graphical representation including a visual representation, in a graphically-overlapping manner, of at least (a) at least a portion of an envelope representing an interior volume of the bodily cavity, and (b) the at least the portion of the catheter. According to some embodiments, the at least the portion of the catheter may be visually represented (i) in accordance with a first property visual characteristic set indicating the first property detected by at least one transducer of the first transducer set, and (ii) based at least on some location signals of a particular location signal set of the plurality of location signal sets representing the particular location in the sequence of locations of the at least the portion of the catheter in the bodily cavity. According to some embodiments, a region of the at least the portion of the envelope may be visually represented (iii) in accordance with a second property visual characteristic set indicating the second property detected by at least one transducer of the second transducer set, and (iv) based at least on some location signals of the plurality of location signal sets representing the sequence of locations of the at least the portion of the catheter in the bodily cavity, the second property visual characteristic set different than the first property visual characteristic set.

In some embodiments, the second transducer set is the first transducer set. In some embodiments, the first visual characteristic set is the same as the first property visual characteristic set.

In some embodiments, the catheter may include a plurality of transducers including the first transducer set and the second transducer set, the plurality of transducers arrangeable in a first spatial distribution. In some embodiments, the visual representation, in the graphically-overlapping manner, may be of at least (a) the at least the portion of the envelope representing the interior volume of the bodily cavity, and (c) a plurality of graphical elements displayed within the visually represented the at least the portion of the catheter, each graphical element of the plurality of graphical elements corresponding to a respective transducer of the plurality of transducers, and the graphical elements of the plurality of graphical elements arranged in a second distribution that is consistent with the first spatial distribution. In some embodiments, the graphical representation may include a display of at least a first graphical element in accordance with a first visual characteristic set indicating the first property, the first graphical element from the plurality of graphical elements and located in a first region of the visually represented the at least the portion of the envelope, and the first graphical element corresponding to a first transducer detecting the first property at least in the state representative of the at least the portion of the catheter being in the particular location in the sequence of locations, the first transducer in the first transducer set.

In some embodiments, the data processing device system may be configured at least by the program at least to receive user input via the input-output device system, and cause the display device system to update the graphical representation, at least in response to the user input, to change the display of at least the first graphical element in accordance with the first visual characteristic set indicating the first property to a display of at least the first graphical element in accordance with a second visual characteristic set indicating a particular property detected by the first transducer at least in the state in which the at least the portion of the catheter is located within the bodily cavity, the second visual characteristic set different than the first visual characteristic set, and the particular property different in type than the first property. In some embodiments, the particular property is the second property. In some embodiments, the particular property is different in type than the second property.

In some embodiments, the first property or the second property is a property responsive to transducer-to-tissue contact. In some embodiments, the first property or the second property is a property responsive to fluid flow in the bodily cavity. In some embodiments, the first property or the second property is responsive to temperature. In some embodiments, the first property or the second property is an electrical property. In some embodiments, the first property or the second property is an electrical property generated at least in part by a body including the bodily cavity.

In some embodiments, the first property is an electrical property generated at least in part by a body including the bodily cavity, and the data processing device system may be configured at least by the program at least to cause the display device system to visually represent a propagation of the electrical property across a visually-represented surface of the at least the portion of the catheter in accordance with the first property visual characteristic set indicating the first property detected by the first transducer set.

In some embodiments, the input-output device system may include a catheter-device-location tracking system, and the data processing device system may be configured at least by the program at least to receive the plurality of location signal sets from the catheter-device-location tracking system. In some embodiments, the catheter-device-location tracking system may be configured to generate the plurality of location signal sets at least in response to one or more electric fields producible by one or more devices of the catheter-device-location tracking system. In some embodiments, the one or more devices of the catheter-device-location tracking system may be configured to operate outside a body comprising the bodily cavity. In some embodiments, the catheter-device-location tracking system may be configured to generate the plurality of location signal sets at least in response to one or more magnetic fields producible by one or more devices of the catheter-device-location tracking system. In some embodiments, the one or more devices of the catheter-device-location tracking system may be configured to operate outside a body comprising the bodily cavity.

In some embodiments, a method executed by a programmed data processing device system of a catheter navigation system may include receiving a plurality of location signal sets, each location signal set of the plurality of location signal sets indicative of a respective location in a sequence of locations at which at least a portion of a catheter has been sequentially located in a bodily cavity. The catheter may include a first transducer set and a second transducer set. Each transducer in the first transducer set may be configured to detect a first property at least in a state in which the at least the portion of the catheter is located within the bodily cavity, and each transducer in the second transducer set may be configured to detect a second property at least in the state in which the at least the portion of the catheter is located within the bodily cavity. The first property may be different in type than the second property. The method may include causing, at least in a state representative of the at least the portion of the catheter being in a particular location in the sequence of locations, a display device system communicatively connected to the programmed data processing device system to display a graphical representation, the graphical representation including a visual representation, in a graphically-overlapping manner, of at least (a) at least a portion of an envelope representing an interior volume of the bodily cavity, and (b) the at least the portion of the catheter. The at least the portion of the catheter may be visually represented (i) in accordance with a first property visual characteristic set indicating the first property detected by at least one transducer of the first transducer set, and (ii) based at least on some location signals of a particular location signal set of the plurality of location signal sets representing the particular location in the sequence of locations of the at least the portion of the catheter in the bodily cavity. A region of the at least the portion of the envelope may be visually represented (iii) in accordance with a second property visual characteristic set indicating the second property detected by at least one transducer of the second transducer set, and (iv) based at least on some location signals of the plurality of location signal sets representing the sequence of locations of the at least the portion of the catheter in the bodily cavity. The second property visual characteristic set may be different than the first property visual characteristic set.

In some embodiments, one or more non-transitory computer-readable storage mediums storing a computer-executable program are provided. The program may include location-signal-set-receiving instructions configured to cause reception of a plurality of location signal sets. Each location signal set of the plurality of location signal sets may be indicative of a respective location in a sequence of locations at which at least a portion of a catheter has been sequentially located in a bodily cavity, the catheter comprising a first transducer set and a second transducer set. Each transducer in the first transducer set may be configured to detect a first property at least in a state in which the at least the portion of the catheter is located within the bodily cavity, and each transducer in the second transducer set may be configured to detect a second property at least in the state in which the at least the portion of the catheter is located within the bodily cavity. The first property may be different in type than the second property. The program may included graphical representation instructions configured to cause generation and display, via a display device system and at least in a state representative of the at least the portion of the catheter being in a particular location in the sequence of locations, of a graphical representation. The graphical representation may include a visual representation, in a graphically-overlapping manner, of at least (a) at least a portion of an envelope representing an interior volume of the bodily cavity, and (b) the at least the portion of the catheter. The at least the portion of the catheter may be visually represented (i) in accordance with a first property visual characteristic set indicating the first property detected by at least one transducer of the first transducer set, and (ii) based at least on some location signals of a particular location signal set of the plurality of location signal sets representing the particular location in the sequence of locations of the at least the portion of the catheter in the bodily cavity. A region of the at least the portion of the envelope may be visually represented (iii) in accordance with a second property visual characteristic set indicating the second property detected by at least one transducer of the second transducer set, and (iv) based at least on some location signals of the plurality of location signal sets representing the sequence of locations of the at least the portion of the catheter in the bodily cavity. The second property visual characteristic set may be different than the first property visual characteristic set.

According to some embodiments, a catheter navigation system may be summarized as including an input-output device system communicatively connected to a display device system, a memory device system storing a program, and a data processing device system communicatively connected to the input-output device system and the memory device system. In some embodiments, the data processing device system may be configured at least by the program at least to receive a plurality of location signal sets, each location signal set of the plurality of location signal sets indicative of a respective location in a sequence of locations at which at least a portion of a catheter has been sequentially located in a bodily cavity, the catheter including a plurality of transducers. In some embodiments, the data processing device system may be configured at least by the program to cause the display device system to progressively visually represent, in a progressively enlarging manner and based on and throughout reception of at least the plurality of location signal sets, at least a portion of an envelope, the envelope representing an interior volume of the bodily cavity. In some embodiments, the data processing device system may be configured at least by the program to cause, during the progressively visually representing in the progressively enlarging manner and based at least on some location signals of a first particular location signal set of the plurality of location signal sets representing a first particular location in the sequence of locations of the at least the portion of the catheter in the bodily cavity, the display device system to display, in a graphically-overlapping manner, at least (a) a visual representation of a first particular envelope enlargement leading to the at least the portion of the envelope, and (b) a first visual representation of the at least the portion of the catheter, the first visual representation of the at least the portion of the catheter displayed in accordance with a first property visual characteristic set indicating a first property detected by one or more transducers of the plurality of transducers at least in a first state representative of the at least the portion of the catheter being in the first particular location in the sequence of locations. In some embodiments, the data processing device system may be configured at least by the program to cause, during the progressively visually representing in the progressively enlarging manner and based at least on some location signals of a second particular location signal set of the plurality of location signal sets representing a second particular location in the sequence of locations of the at least the portion of the catheter in the bodily cavity, the display device system to display, in a graphically-overlapping manner, at least (c) a visual representation of a second particular envelope enlargement leading to the at least the portion of the envelope, and (d) at least a second visual representation of the at least the portion of the catheter, the second visual representation of the at least the portion of the catheter displayed in accordance with a second property visual characteristic set indicating a second property detected by one or more transducers of the plurality of transducers at least in a second state representative of the at least the portion of the catheter being in the second particular location in the sequence of locations, the second property visual characteristic set different than the first property visual characteristic set, and the second property different in type than the first property.

In some embodiments, the first visual representation of the at least the portion of the catheter may include a plurality of graphical elements, the plurality of graphical elements including at least a first graphical element displayed in accordance with a first visual characteristic set indicating the first property detected by a first transducer of the plurality of transducers at least in the first state representative of the at least the portion of the catheter being in the first particular location in the sequence of locations, each graphical element of the plurality of graphical elements corresponding to a respective transducer of the plurality of transducers, the plurality of transducers arrangeable in a first spatial distribution, the graphical elements of the plurality of graphical elements arranged in a second distribution that is consistent with the first spatial distribution, and the first graphical element corresponding to the first transducer. In some embodiments the second visual representation of the at least the portion of the catheter may include at least the first graphical element of the plurality of graphical elements displayed in accordance with a second visual characteristic set indicating the second property detected by the first transducer of the plurality of transducers at least in the second state representative of the at least the portion of the catheter being in the second particular location in the sequence of locations, the second visual characteristic set different than the first visual characteristic set. In some embodiments, the first visual characteristic set is the same as the first property visual characteristic set. In some embodiments, the second visual characteristic set is the same as the second property visual characteristic set.

In some embodiments, at least in the first state representative of the at least the portion of the catheter being in the first particular location in the sequence of locations, the visual representation of the first particular envelope enlargement leading to the at least the portion of the envelope may be displayed in accordance with a third property visual characteristic set indicating a particular property detected by a first transducer set of the plurality of transducers at least in the first state representative of the at least the portion of the catheter being in the first particular location in the sequence of locations, the particular property being the same as the first property.

In some embodiments, at least in the first state representative of the at least the portion of the catheter being in the first particular location in the sequence of locations, the visual representation of the first particular envelope enlargement leading to the at least the portion of the envelope may be displayed in accordance with a third property visual characteristic set indicating a particular property detected by a first transducer set of the plurality of transducers at least in the first state representative of the at least the portion of the catheter being in the first particular location in the sequence of locations, the particular property being different in type than the first property.

In some embodiments, at least in the second state representative of the at least the portion of the catheter being in the second particular location in the sequence of locations, the visual representation of the second particular envelope enlargement leading to the at least the portion of the envelope may be displayed in accordance with a third property visual characteristic set indicating a particular property detected by a first transducer set of the plurality of transducers at least in the second state representative of the at least the portion of the catheter being in the second particular location in the sequence of locations, the particular property being the same as the first property or the second property.

In some embodiments, at least in the second state representative of the at least the portion of the catheter being in the second particular location in the sequence of locations, the visual representation of the second particular envelope enlargement leading to the at least the portion of the envelope may be displayed in accordance with a third property visual characteristic set indicating a particular property detected by a first transducer set of the plurality of transducers at least in the second state representative of the at least the portion of the catheter being in the second particular location in the sequence of locations, the particular property being different in type than (i) the first property, or (ii) the second property, or each of (i) and (ii).

In some embodiments, at least in the first state representative of the at least the portion of the catheter being in the first particular location in the sequence of locations, the visual representation of the first particular envelope enlargement leading to the at least the portion of the envelope may be displayed in accordance with a first particular visual characteristic set, and wherein at least in the second state representative of the at least the portion of the catheter being in the second particular location in the sequence of locations, the visual representation of the first particular envelope enlargement leading to the at least the portion of the envelope is displayed in accordance with a second particular visual characteristic set, the second particular visual characteristic set being the same as the first particular visual characteristic set. In some embodiments, at least in the second state representative of the at least the portion of the catheter being in the second particular location in the sequence of locations, the visual representation of the second particular envelope enlargement leading to the at least the portion of the envelope may be displayed in accordance with a third particular visual characteristic set, the third particular visual characteristic set being the same as the first particular visual characteristic set and the second particular visual characteristic set.

In some embodiments, a method executed by a programmed data processing device system of a catheter navigation system may include receiving a plurality of location signal sets, each location signal set of the plurality of location signal sets indicative of a respective location in a sequence of locations at which at least a portion of a catheter has been sequentially located in a bodily cavity, the catheter comprising a plurality of transducers. The method may include causing a display device system communicatively connected to the programmed data processing device system to progressively visually represent, in a progressively enlarging manner and based on and throughout reception of at least the plurality of location signal sets, at least a portion of an envelope, the envelope representing an interior volume of the bodily cavity. The method may include causing, during the progressively visually representing in the progressively enlarging manner and based at least on some location signals of a first particular location signal set of the plurality of location signal sets representing a first particular location in the sequence of locations of the at least the portion of the catheter in the bodily cavity, the display device system to display, in a graphically-overlapping manner, at least (a) a visual representation of a first particular envelope enlargement leading to the at least the portion of the envelope, and (b) a first visual representation of the at least the portion of the catheter. The first visual representation of the at least the portion of the catheter may be displayed in accordance with a first property visual characteristic set indicating a first property detected by one or more transducers of the plurality of transducers at least in a first state representative of the at least the portion of the catheter being in the first particular location in the sequence of locations. The method may include causing, during the progressively visually representing in the progressively enlarging manner and based at least on some location signals of a second particular location signal set of the plurality of location signal sets representing a second particular location in the sequence of locations of the at least the portion of the catheter in the bodily cavity, the display device system to display, in a graphically-overlapping manner, at least (c) a visual representation of a second particular envelope enlargement leading to the at least the portion of the envelope, and (d) at least a second visual representation of the at least the portion of the catheter. The second visual representation of the at least the portion of the catheter may be displayed in accordance with a second property visual characteristic set indicating a second property detected by one or more transducers of the plurality of transducers at least in a second state representative of the at least the portion of the catheter being in the second particular location in the sequence of locations. The second property visual characteristic set may be different than the first property visual characteristic set, and the second property may be different in type than the first property.

In some embodiments, one or more non-transitory computer-readable storage mediums storing a computer-executable program are provided. The program may include location-signal-set-receiving instructions configured to cause reception of a plurality of location signal sets. Each location signal set of the plurality of location signal sets may be indicative of a respective location in a sequence of locations at which at least a portion of a catheter has been sequentially located in a bodily cavity. The catheter may include a plurality of transducers. The program may include visual representation instructions configured to cause a display device system to progressively visually represent, in a progressively enlarging manner and based on and throughout reception of at least the plurality of location signal sets, at least a portion of an envelope, the envelope representing an interior volume of the bodily cavity. The visual representation instructions may be configured to cause, during the progressively visually representing in the progressively enlarging manner and based at least on some location signals of a first particular location signal set of the plurality of location signal sets representing a first particular location in the sequence of locations of the at least the portion of the catheter in the bodily cavity, the display device system to display, in a graphically-overlapping manner, at least (a) a visual representation of a first particular envelope enlargement leading to the at least the portion of the envelope, and (b) a first visual representation of the at least the portion of the catheter. The first visual representation of the at least the portion of the catheter may be displayed in accordance with a first property visual characteristic set indicating a first property detected by one or more transducers of the plurality of transducers at least in a first state representative of the at least the portion of the catheter being in the first particular location in the sequence of locations. The visual representation instructions may be configured to cause, during the progressively visually representing in the progressively enlarging manner and based at least on some location signals of a second particular location signal set of the plurality of location signal sets representing a second particular location in the sequence of locations of the at least the portion of the catheter in the bodily cavity, the display device system to display, in a graphically-overlapping manner, at least (c) a visual representation of a second particular envelope enlargement leading to the at least the portion of the envelope, and (d) at least a second visual representation of the at least the portion of the catheter. The second visual representation of the at least the portion of the catheter may be displayed in accordance with a second property visual characteristic set indicating a second property detected by one or more transducers of the plurality of transducers at least in a second state representative of the at least the portion of the catheter being in the second particular location in the sequence of locations. The second property visual characteristic set may be different than the first property visual characteristic set, and the second property may be different in type than the first property.

Various embodiments of the present invention may include systems, devices, or machines that are or include combinations or subsets of any one or more of the systems, devices, or machines and associated features thereof summarized above or otherwise described herein.

Further, all or part of any one or more of the systems, devices, or machines summarized above or otherwise described herein or combinations or sub-combinations thereof may implement or execute all or part of any one or more of the processes or methods described herein or combinations or sub-combinations thereof.

It should be noted that various embodiments of the present invention include variations of the methods or processes summarized above or otherwise described herein (including the figures) and, accordingly, are not limited to the actions described or shown in the figures or their ordering, and not all actions shown or described are required, according to various embodiments. According to various embodiments, such methods may include more or fewer actions and different orderings of actions. Any of the features of all or part of any one or more of the methods or processes summarized above or otherwise described herein (including the figures) may be combined with any of the other features of all or part of any one or more of the methods or processes summarized above or otherwise described herein or shown in the figures.

In addition, a computer program product may be provided that comprises program code portions for performing some or all of any one or more of the methods or processes and associated features thereof described herein, when the computer program product is executed by a computer or other computing device or device system. Such a computer program product may be stored on one or more computer-readable storage mediums or medium systems, also referred to as one or more computer-readable data storage mediums or medium systems.

In some embodiments, each of any of one or more of the computer-readable data storage medium systems (also referred to as processor-accessible memory device systems) described herein is a non-transitory computer-readable (or processor-accessible) data storage medium system (or memory device system) including or consisting of one or more non-transitory computer-readable (or processor-accessible) storage mediums (or memory devices) storing the respective program(s) which may configure a data processing device system to execute some or all of any of one or more of the methods or processes described herein.

Further, any of all or part of one or more of the methods or processes and associated features thereof discussed herein may be implemented or executed by all or part of a device system, apparatus, or machine, such as all or a part of any of one or more of the systems, apparatuses, or machines described herein or a combination or sub-combination thereof.

BRIEF DESCRIPTION OF THE DRAWINGS

It is to be understood that the attached drawings are for purposes of illustrating aspects of various embodiments and may include elements that are not to scale.

FIGS. 14 and 15 illustrate various catheter navigation methods executable by at least part of the systems described herein, according to various embodiments of the present invention.

DETAILED DESCRIPTION

Figure 1:
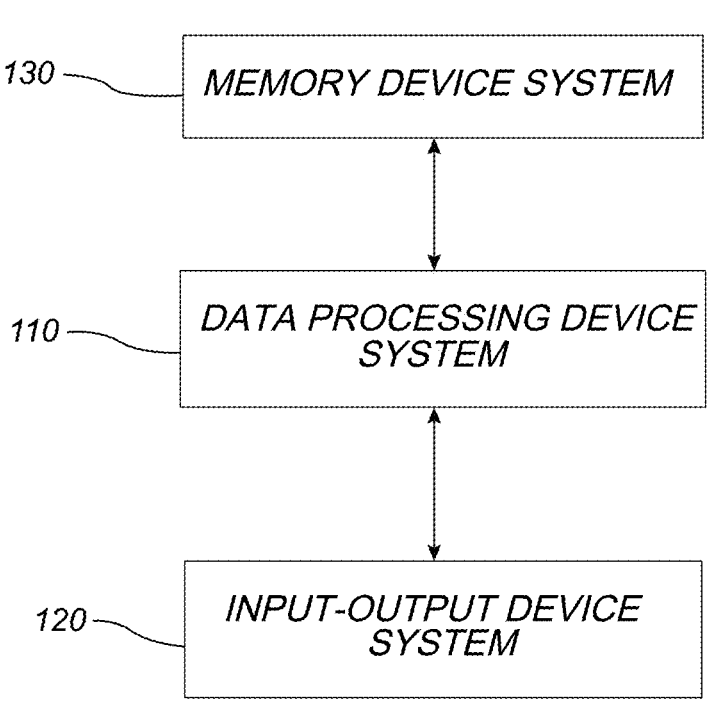
FIG. 1 includes a schematic representation of a catheter navigation system according to various example embodiments, the catheter navigation system including a data processing device system, an input-output device system, and a memory device system.

At least some embodiments of the present invention improve upon percutaneous or intravascular medical procedures by providing improved catheter navigation systems and methods. According to some embodiments of the present invention, a catheter-device-location tracking system provides a plurality of location signal sets to a data processing device system, and a plurality of transducers of a transducer-based device, which may be part of the catheter-device-location tracking system, provide a plurality of contact signal sets to the data processing device system, which also may be part of the catheter-device-location tracking system. The plurality of location signal sets may be generated as a result of an interaction between transducers of the transducer-based device, a reference device, and a generated electric or magnetic field. The plurality of location signal sets may be provided by the catheter-device-location tracking system while the transducer-based device is moving throughout the bodily cavity in real time, informing the data processing device system of a sequence of three-dimensional locations of the transducer-based device and its transducers in real time. The plurality of contact signal sets may be generated based on an interaction of the transducers with a tissue surface of the bodily cavity to detect a degree of contact between each respective transducer and the tissue surface. Such contact signal sets may also be provided to the data processing device system in real time, informing it of respective degrees of tissue contact detected by the respective transducers in real time. With the stream of location signal sets and the contact signal sets, the data processing device system may be configured to generate a graphical representation of a sequence of progressive enlargements of at least a portion of an envelope representing an interior volume of the bodily cavity as the transducer-based device moves throughout the bodily cavity. In this regard, the envelope may be a three-dimensional representation of an interior surface region of the bodily cavity, as well as one or more regions where one or more ports lead into or out of the bodily cavity. As the transducer-based device continues to explore new locations in the bodily cavity, the envelope is enlarged (e.g., added to) or refined in the graphical representation to represent new or revised surface regions of the bodily cavity revealed by the location signal sets and the contact signal sets from the transducer-based device's progression into the new locations, according to some embodiments. In this regard, an interior volume of the bodily cavity can be displayed to an operator in real time as it is being mapped, thereby allowing treatment to occur during the mapping process without having to wait until the entire bodily cavity is mapped prior to performing treatment, according to some embodiments. In some embodiments, treatment occurs after the mapping process is completed.

In some embodiments, the graphical representation of the envelope representing an interior volume of the bodily cavity may visually represent on its surface regions the various degrees of tissue contact that were detected by the transducers when they contacted the corresponding tissue surfaces of the bodily cavity. Such visual representation of the various degrees of tissue contact may inform the operator of surface regions that may, in the case of a visually represented low degree of tissue contact, need to be revisited by the transducer-based device with greater tissue contact to improve the mapped location of such surface regions or need may need further or enhanced treatment procedures. Or, a visual representation of a region of no tissue contact surrounded by a region of sufficient tissue contact may indicate to the operator the location of a port or opening in the bodily cavity. Or, a visual representation of a region of excessive tissue contact may indicate to the operator that the corresponding tissue surface was excessively stretched by the transducer-based device when it was mapped and, therefore, the operator may know to move the transducer-based device less aggressively in that region when treating it, for example, by tissue ablation, which may help reduce the risk of damaging tissue. In this regard, the visual representations according to various embodiments of the present invention facilitate navigation of the transducer-based device in a manner that produces a substantially uniform and moderate degree of tissue contact throughout the mapping process, in order to reflect an accurate representation of the tissue surface. On the other hand, a region of the visual representation of the tissue surface that reveals excessive tissue contact may indicate that such region is distorted or relatively inaccurate with respect to the actual location of the tissue surface.

In some embodiments, the data processing device system, utilizing at least the location signal sets, concurrently displays a graphical representation of the transducer-based device and the envelope representing the interior volume of the bodily cavity and, in some embodiments, the graphical representation of the transducer-based device includes transducer graphical elements representing the transducers of the transducer-based device. In this regard, the operator is able to view the present location of the transducer-based device and, in some embodiments, its transducers, within the interior volume of the bodily cavity, according to some embodiments. In some embodiments, the graphical representation of the transducer-based device is represented as moving and causing the above-discussed progressive enlargements of the envelope as the transducer-based device moves throughout the bodily cavity, thereby providing the operator with an effective understanding of not only the present location of the transducer-based device in the bodily cavity by way of the graphical representation of the transducer-based device, but also the historical locations of the transducer-based device by way of the graphical representation of the at least the portion of the envelope.

In some embodiments, at least some of the progressive enlargements of the graphical representation of the envelope representing an interior volume of the bodily cavity are produced with respect to a graphical representation of a pre-existing image or model, such as a CT scan, of the bodily cavity, further assisting the operator to understand the state of development of the envelope, as well as potential future desired movements of the transducer-based device to more thoroughly and efficiently develop the envelope. In some embodiments, graphical representation of a pre-existing image or model, such as a CT scan, of the bodily cavity and a graphical representation of at least part of the envelope are displayed in an overlapping or superimposed manner.

In some embodiments, the graphical representation of the transducer-based device and, in some embodiments, its transducers, may have visual characteristics that indicate the various degrees of tissue contact detected by the transducers of the transducer-based device. In some embodiments, the visually indicated various degrees of tissue contact represent degrees of tissue contact presently or currently detected by the transducers. Concurrently, in some embodiments, the graphical representation of the at least the portion of the envelope includes visual characteristics that indicate the various degrees of tissue contact that were detected by the respective transducers when they mapped the respective regions of the bodily cavity. Accordingly, in some embodiments, the operator is able to concurrently understand the present tissue-contact state exhibited by the transducers by viewing the graphical representation of the transducer-based device and the historical tissue-contact states exhibited by transducers in the past by viewing the graphical representation of the at least the portion of the envelope.

In some embodiments, where overlapping graphical representations are displayed, such as a combination of the graphical representation of the transducer-based device, the graphical representation of the envelope representing an interior volume of the bodily cavity, or the graphical representation of the pre-existing image or model of the bodily cavity, blending of colors utilized to represent each of the graphical representations is implemented in a translucent or semi-transparent manner to provide the operator with an efficient understanding of the relative positioning and locational depth (e.g., distance from a viewing perspective or location) of the objects represented by the graphical representations. In some embodiments in which a port or opening in the bodily cavity is represented in the envelope as completely transparent (i.e., with no color), and in which at least a portion of the graphical representation of the transducer-based device is viewable through the port or opening, such portion of the graphical representation may be displayed without color blending (i.e., in the true, unmodified colors of the graphical representation of the transducer-based device) so as to provide the operator with a realistic view that appears as if the operator is peering through the port or opening and directly seeing the portion of the transducer-based device.

In some embodiments, the graphical representation of the at least the portion of the envelope, the graphical representation of the transducer-based device, or both, have visual characteristics that indicate an electrical property detected by the transducers. As with the tissue-contact signals, the electrical property indicated via the graphical representation of the transducer-based device may represent presently detected degrees of the electrical property, and the electrical property indicated via the graphical representation of the at least the portion of the envelope may represent historically detected degrees of the electrical property when the transducers were at the respective locations in the bodily cavity. According to various embodiments, the electrical properties are associated with electrical signals generated by the patient or electrical signals generated by a body that includes the bodily cavity.

In light of the above-discussed and other features and advantages of various embodiments of the present invention, improved catheter navigation systems and methods are provided.

In this regard, it should be noted that the invention is not limited to the above-discussed or any other examples provided herein, which are referred to for purposes of illustration only. Further in this regard, in the descriptions herein, certain specific details are set forth in order to provide a thorough understanding of various embodiments of the invention. However, one skilled in the art will understand that the invention may be practiced at a more general level without one or more of these details. In other instances, well known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects. In addition, unless otherwise explicitly noted or required by context, the word "subset" is intended to mean a set having the same or fewer elements of those present in the subset's parent or superset.

In the following description, some embodiments of the present invention are described in terms that may be implemented at least in part as one or more software programs configured to be executed by a data processing device system. Some or all of such software programs may be equivalently constructed in hardware. Software and hardware not specifically shown, suggested, or described herein that is useful for implementation of any of various embodiments of the present invention are conventional and within the ordinary skill of the art.

In the following description, some embodiments of the present invention may be implemented at least in part by a data processing device system configured by a software program. Such a program may equivalently be implemented as multiple programs, and some or all of such software program(s) may be equivalently constructed in hardware.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'based at least on A' includes A as well as the possibility of one or more other additional elements besides A. In the same manner, the phrase, 'based on A' includes A, as well as the possibility of one or more other additional elements besides A. However, the phrase, 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The word "device", the word "machine", the word "system", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified according to various embodiments that a device or machine or device system resides entirely within a same housing to exclude embodiments where the respective device, machine, system, or device system resides across different housings. The word "device" may equivalently be referred to as a "device system" in some embodiments.

Further, the phrase "in response to" may be used in this disclosure. For example, this phrase may be used in the following context, where an event A occurs in response to the occurrence of an event B. In this regard, such phrase includes, for example, that at least the occurrence of the event B causes or triggers the event A.

In some embodiments, the term "adjacent", the term "proximate", and the like refer at least to a sufficient closeness between the objects defined as adjacent, proximate, or the like, to allow the objects to interact in a designated way. For example, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the term "adjacent", the term "proximate", and the like additionally or alternatively refer to objects that do not have another substantially similar object between them. For example, object A and object B could be considered adjacent or proximate if they contact each other (and, thus, it could be considered that no other object is between them), or if they do not contact each other but no other object that is substantially similar to object A, object B, or both objects A and B, depending on the embodiment, is between them. In some embodiments, the term "adjacent", the term "proximate", and the like additionally or alternatively refer to at least a sufficient closeness between the objects defined as adjacent, proximate, and the like, the sufficient closeness being within a range that does not place any one or more of the objects into a different or dissimilar region, or does not change an intended function of any one or more of the objects or of an encompassing object that includes a set of the objects. Different embodiments of the present invention adopt different ones or combinations of the above definitions. Of course, however, the term "adjacent", the term "proximate", and the like are not limited to any of the above example definitions, according to some embodiments. In addition, the term "adjacent" and the term "proximate" do not have the same definition, according to some embodiments.

The phrase "bodily cavity" as used in this disclosure should be understood to mean a cavity in a body. The bodily cavity may be a cavity provided in a bodily organ (e.g., an intracardiac cavity or chamber of a heart). The bodily cavity may be provided by a bodily vessel.

The word "ablation" as used in this disclosure should be understood to include, for example, any disruption to certain properties of tissue. Most commonly, the disruption is to the electrical conductivity and is achieved by thermal-based treatment, which can be generated with resistive or radio-frequency (RF) techniques, or cryo-based techniques, for example. However, any other technique for such disruption may be included when the term "ablation" is used, such as mechanical, chemical, electroporation or optical techniques. Various catheters described in this disclosure may, in some embodiments, be employed to deliver ablative energy.

The term "transducer" as used in this disclosure should be interpreted broadly as any device capable of distinguishing between blood and solid tissue, sensing temperature, creating heat, ablating tissue, sensing, sampling or measuring electrical activity of a tissue surface of a bodily cavity (e.g., sensing, sampling or measuring intracardiac electrograms, or sensing, sampling or measuring intracardiac voltage data), stimulating tissue, or any combination thereof. A transducer can convert input energy of one form into output energy of another form. Without limitation, a transducer can include an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed. In this regard, although transducers, electrodes, or both transducers and electrodes are referenced with respect to various embodiments, it is understood that other transducers or transducer elements may be employed in other embodiments. It is understood that a reference to a particular transducer in various embodiments may also imply a reference to an electrode, as an electrode may be part of the transducer.

The phrase "derivative thereof" and the like is or may be used herein in the context of a derivative of data or information merely to emphasize the possibility that such data or information may be modified or subject to one or more operations. For example, if a device generates first data for display, the process of converting the generated first data into a format capable of being displayed may alter the first data. This altered form of the first data may be considered a derivative of the first data. For instance, the first data may be a one-dimensional array of numbers, but the display of the first data may be a color-coded bar chart representing the numbers in the array. For another example, if the above-mentioned first data is transmitted over a network, the process of converting the first data into a format acceptable for network transmission or understanding by a receiving device may alter the first data. As before, this altered form of the first data may be considered a derivative of the first data. For yet another example, generated first data may undergo a mathematical operation, a scaling, or a combining with other data to generate other data that may be considered derived from the first data. In this regard, it can be seen that data is commonly changing in form or being combined with other data throughout its movement through one or more data processing device systems, and any reference to information, signals, or data herein is intended to include these and like changes, regardless of whether or not the phrase "derivative thereof" or the like is used in reference to the information or data, unless otherwise required by context. As indicated above, usage of the phrase "or a derivative thereof" or the like merely emphasizes the possibility of such changes. Accordingly, the addition of or deletion of the phrase "or a derivative thereof" or the like should have no impact on the interpretation of the respective data or information. For example, the above-discussed color-coded bar chart may be considered a derivative of the respective first data or may be considered the respective first data itself.

The term "program" in this disclosure should be interpreted to include one or more programs including a set of instructions or modules that may be executed by one or more components in a system, such as a controller system or data processing device system, in order to cause the system to perform one or more operations. The set of instructions or modules may be stored by any kind of memory device, such as those described subsequently with respect to at least the memory device system 130 shown in FIG. 1. In addition, this disclosure may describe or similarly describe that the instructions or modules of a program are configured to cause the performance of an action. The phrase "configured to" in this context is intended to include at least (a) instructions or modules that are presently in a form executable by one or more data processing devices to cause performance of the action (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the action (e.g., in the case where the instructions or modules are encrypted in a non-executable manner, but through performance of a decryption process, would be translated into a form ready for execution). Such descriptions should be deemed to be equivalent to describing that the instructions or modules are configured to cause the performance of the action. The word "module" may be defined as a set of instructions. The word "program" and the word "module" may each be interpreted to include multiple sub-programs or multiple sub-modules, respectively. In this regard, reference to a program or a module may be considered to refer to multiple programs or multiple modules.

Further, it is understood that information or data may be operated upon, manipulated, or converted into different forms as it moves through various devices or workflows. In this regard, unless otherwise explicitly noted or required by context, it is intended that any reference herein to information, signals, or data includes modifications to that information or data. For example, "data X" may be encrypted for transmission, and a reference to "data X" is intended to include both its encrypted and unencrypted forms, unless otherwise required or indicated by context. For another example, "image information Y" may undergo a noise filtering process, and a reference to "image information Y" is intended to include both the pre-processed form and the noise-filtered form, unless otherwise required or indicated by context. In other words, both the pre-processed form and the noise-filtered form are considered to be "image information Y", unless otherwise required or indicated by context. In order to stress this point, the phrase "or a derivative thereof" or the like may be, but need not be, used herein. Continuing the preceding example, the phrase "image information Y or a derivative thereof" refers to both the pre-processed form and the noise-filtered form of "image information Y", unless otherwise required or indicated by context, with the noise-filtered form potentially being considered a derivative of "image information Y". However, non-usage of the phrase "or a derivative thereof" or the like nonetheless includes derivatives or modifications of information or data just as usage of such a phrase does, as such a phrase, when used, is merely used for emphasis.

Further, the phrase "graphical representation" used herein is intended to include a visual representation presented via a display device system and may include computer-generated text, graphics, animations, or one or more combinations thereof, which may include one or more visual representations originally generated, at least in part, by an image-capture device, such as CT scan images, MRI images, or images created from a navigation system (e.g., electric potential navigation system or an electromagnetic navigation system).

Figure 14:
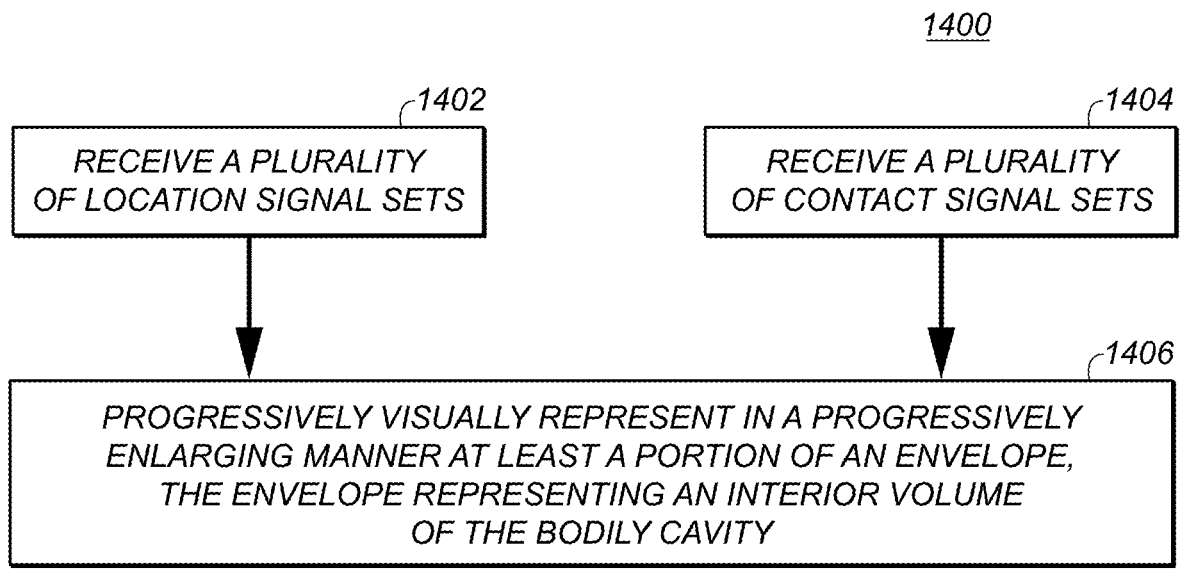

Further still, example methods are described herein at least with respect to FIGS. 14 and 15. Such figures are described to include blocks associated with computer-executable instructions. It should be noted that the respective instructions associated with any such blocks herein need not be separate instructions and may be combined with other instructions to form a combined instruction set. The same set of instructions may be associated with more than one block. In this regard, the block arrangement shown in method FIGS. 14 and 15 herein is not limited to an actual structure of any program or set of instructions or required ordering of method tasks, and such method FIGS. 14 and 15, according to some embodiments, merely illustrate the tasks that instructions are configured to perform, for example upon execution by a data processing device system in conjunction with interactions with one or more other devices or device systems.

FIG. 1 schematically illustrates a special purpose catheter navigation system 100 that may be configured to at least facilitate navigation of at least a portion of a catheter including one or more transducers, according to some embodiments. The system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 may include one or more data processing devices that implement or execute, in conjunction with other devices, such as those in the system 100, methods of various embodiments of the present invention, including the example methods of FIGS. 14 and 15 described herein. Each of the phrases "data processing device", "data processor", "processor", and "computer" and the like is intended to include any data processing device, such as a central processing unit ("CPU"), a desktop computer, a laptop computer, a mainframe computer, a tablet computer such as an iPad (Trademark Apple Inc., Cupertino California), a personal digital assistant, a cellular phone, a smartphone, or any other device for processing data, managing data, or handling data, whether implemented with electrical, magnetic, optical, quantum, biological components, or otherwise.

The memory device system 130 includes one or more processor-accessible memory devices configured to store program instructions and other information, including the information and program instructions needed to execute the methods of various embodiments, including the example methods of FIGS. 14 and 15 described herein. In this regard, each of the blocks illustrated in the example methods of FIGS. 14 and 15 may represent program instructions stored in the memory device system 130 and configured to cause execution of the respective operation. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" and the like is intended to include any processor-accessible data storage device or medium, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include or be a processor-accessible (or computer-readable) data storage medium. In some embodiments, each of the phrases "processor-accessible memory" and "processor-accessible memory device" is intended to include or be a non-transitory processor-accessible (or computer-readable) data storage medium. In some embodiments, the processor-accessible memory device system 130 may be considered to include or be a non-transitory processor-accessible (or computer-readable) data storage medium system. And, in some embodiments, the memory device system 130 may be considered to include or be a non-transitory processor-accessible (or computer-readable) storage medium system or data storage medium system including or consisting of one or more non-transitory processor-accessible (or computer-readable) storage or data storage mediums.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending on the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 may be implemented by a single application-specific integrated circuit (ASIC) or field-programmable gate array (FPGA) in some embodiments.

The input-output device system 120 may include a mouse, a keyboard, a touch screen, another computer, a processor-accessible memory device system, or any device or combination of devices from which a desired selection, desired information, instructions, or any other data is input to the data processing device system 110. The input-output device system 120 may include a user-activatable control system that is responsive to a user action. The user-activatable control system may include at least one user input element, such as, for example, a mouse button, a keyboard key, a touch screen, or any other user input element that may be placed into an activated or deactivated state on the basis of a particular user action, such as, for example, the clicking/releasing of a mouse button, the pressing/releasing of a keyboard key, or the contacting of/separating from a touch screen. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion of a transducer-based device system or catheter-based device. The phrase "transducer-based device system" is intended to include one or more physical systems that include one or more transducers. The phrase "transducer-based device" is intended to include one or more physical devices that include one or more transducers.

The input-output device system 120 also may include an image-generating device system, a display device system, a speaker device system, a computer, a processor-accessible memory device system, a network interface card or network interface circuitry, or any device or combination of devices to which information, instructions, or any other data is output by the data processing device system 110. In this regard, the input-output device system 120 may include various other devices or systems described in various embodiments. The input-output device system 120 may include any suitable interface for outputting information, instructions, or data to other devices and systems described in various ones of the embodiments. If the input-output device system 120 includes a processor-accessible memory device, such memory device may or may not form part or all of the memory device system 130. In some embodiments, the input-output device system 120 may include one or more display devices that display one or more of the graphical user interfaces, which may include the graphical representations of at least FIGS. 8-13 described below.

Various embodiments of catheter device systems including transducer-based devices are described herein. Some of the described devices are medical devices that are percutaneously or intravascularly deployed. Some of the described devices are moveable between a delivery or unexpanded configuration (e.g., FIG. 5 discussed below) in which a portion of the device is sized for passage through a bodily opening leading to a bodily cavity, and an expanded or deployed configuration (e.g., at least FIGS. 4 and 6 discussed below) in which the portion of the device has a size too large for passage through the bodily opening leading to the bodily cavity. An example of an expanded or deployed configuration is when the portion of the transducer-based device is in its intended-deployed-operational state, which may be inside the bodily cavity or in a testing environment outside of a body to facilitate training, device evaluation, or quality control. Another example of the expanded or deployed configuration is when the portion of the trans-ducer-based device is being changed from the delivery configuration to the intended-deployed-operational state to a point where the portion of the device now has a size too large for passage through the bodily opening leading to the bodily cavity. The intended operational state may be a particular state, which the portion of the device is intended to have during the performance of a desired diagnostic or treatment procedure.

In some example embodiments, the device includes trans-ducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical system to determine degrees of tissue contact exhibited by respective transducers and to map the cavity, for example, using positions of openings or ports into and out of the cavity to determine a position or orientation (e.g., pose), or both, of the portion of the device in the bodily cavity. In some example embodiments, the described devices are capable of ablating tissue in a desired pattern within the bodily cavity, for example, by way of one or more transducers of the transducer-based device transmitting tis-sue-ablative energy.

In some example embodiments, the devices are capable of sensing various cardiac functions (e.g., electrophysiological activity including intracardiac voltages). In some example embodiments, the devices are capable of providing stimu-lation (e.g., electrical stimulation) to tissue within the bodily cavity. Electrical stimulation may include pacing.

Figure 2:
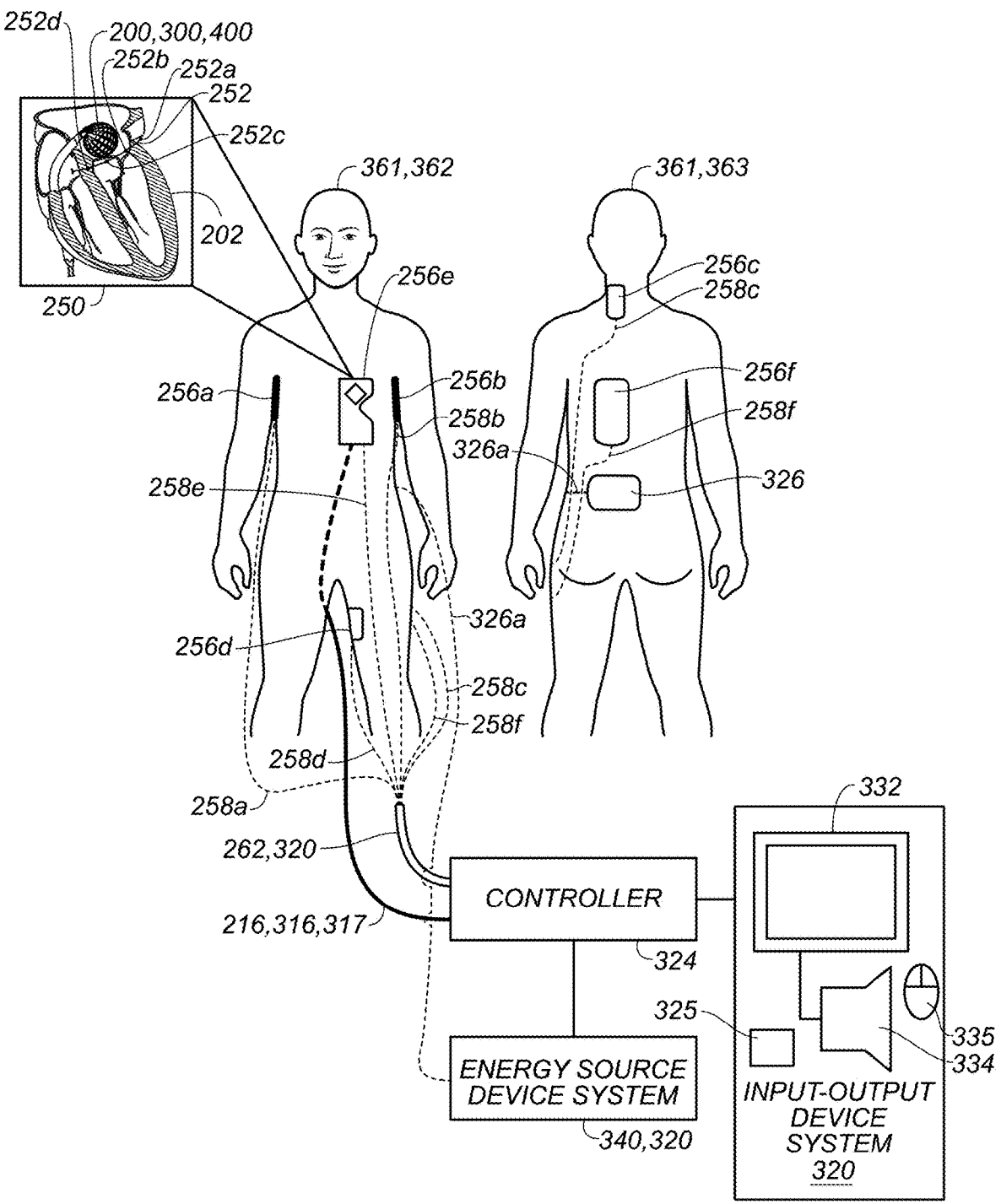
FIG. 2 includes a partially schematic representation of some particular implementations of the catheter navigation system of FIG. 1 implementing an electric-field-based location system, according to various example embodiments.

FIG. 2 includes a partially schematic representation of some particular implementations of the catheter navigation system 100 of FIG. 1 implementing an electric-field-based location system, according to various example embodi-ments. FIG. 2 illustrates a controller 324, which may be a particular implementation of the data processing device system 110 shown in FIG. 1. Illustrated in FIG. 2 is an input-output device system 320 communicatively connected to the controller 324 and may include a display device system 332, a mouse 335 or other pointing device system, a speaker device system 334 or other audio output device system, or a sensing device system 325, according to various embodiments. Possible contents of the input-output device system 320 are discussed in more detail below. The input-output device system 320 may be a particular implementa-tion of the input-output device system 120 shown in FIG. 1. FIG. 2 also illustrates, in cut-out illustration window 250, a catheter or transducer-based device 200, 300, or 400, dis-cussed in more detail below, which may be communicatively connected to the controller 324 via electrical conductors 216, cable 316, electrical leads 317 (discussed in more detail below; see, e.g., at least FIGS. 4-6), or a combination thereof, according to various embodiments. The electrical conductors 216, cable 316, or electrical leads 317 may reside, at least in part, within a catheter shaft 214 or 314 or within a catheter sheath 212 or 312 discussed in more detail below (see, e.g., at least FIGS. 4-6). The catheter or trans-ducer-based device 200, 300, or 400 may include one or more transducers (discussed in more detail below; see, e.g., at least FIGS. 4-7) and may be included in the input-output device system 320, according to some embodiments. In FIG. 2, the catheter or transducer-based device 200, 300, or 400 is illustrated within a heart 202 of a patient 361 via cut-out illustration window 250, although the catheter or transducer-based device 200, 300, or 400 may instead be operated outside of any living being, e.g., in a quality-control, train-ing, or testing environment. The single patient 361 is illus-trated in two parts in FIG. 2 merely to concurrently show the front-side 362 and the back-side 363 of the patient 361, although the various connections to the controller 324 are only fully shown via the illustrated front-side 362 of the patient 361 for purposes of clarity. The portion of the electrical conductors 216, cable 316, or electrical leads 317 that is outside the patient 361 is illustrated in solid line in FIG. 2, and the portion of the electrical conductors 216, cable 316, or electrical leads 317 that is inside the patient 361 is illustrated in broken line in FIG. 2.

Also illustrated in FIG. 2 is an energy source device system 340 communicatively connected to the controller 324. The energy source device system 340 may be part of the input-output device system 320 and may be configured to provide energy to the transducers of the catheter or trans-ducer-based device 200, 300, or 400 for sensing, tissue ablation, or both, according to various embodiments and as discussed in more detail below. Electrode 326 may be communicatively connected to energy source device system 340 via conductor 326a. Electrode 326 may be placed externally on the body of the patient 361, according to some embodiments. Electrode 326 may be an indifferent elec-trode, which may facilitate the performance of impedance sensing or ablation, particularly monopolar or blended monopolar ablation, according to some embodiments. Indif-ferent electrode 326 is discussed in more detail below.

FIG. 2 also illustrates electrodes 256a, 256b, 256c, 256d, 256e, and 256f that are placed externally on the body of the patient 361, according to some embodiments. The electrodes 256a, 256b, 256c, 256d, 256e, and 256f may be included in the input-output device system 320 and may be communi-catively connected to the controller 324 via respective electrical conductors 258a, 258b, 258c, 258d, 258e, and 258fa partially inside cable 262, according to some embodi-ments. Although respective electrical conductors 258a, 258b, 258c, 258d, 258e, and 256f are shown within a same cable 262 for clarity of illustration, one or more of such electrical conductors may be in separate cables. According to some embodiments, electrodes 256a, 256b, 256c, 256d, 256e, and 256f are configured to generate electric fields that enable the controller 324 to determine, in conjunction with corresponding sensing performed by transducers of the catheter or transducer-based device 200, 300, or 400, X, Y, and Z coordinate axis location information of the catheter or transducer-based device 200, 300, or 400 within the heart 202 of the patient 361 or in a quality-control, training, or testing environment. In particular, electrodes 256a and 256b (a first pair of electrodes) may be configured to generate a first electric field at a first frequency or frequency range that the transducers of the catheter or transducer-based device 200, 300, or 400 are configured to sense as, e.g., respective X-axis locations of the respective transducers. Similarly, electrodes 256c and 256d (a second pair of electrodes) may be configured to generate a second electric field at a second frequency or frequency range that the transducers of the catheter or transducer-based device 200, 300, or 400 are configured to sense as, e.g., respective Y-axis locations of the respective transducers. Similarly, electrodes 256e and 256f (a third pair of electrodes) may be configured to generate a third electric field at a third frequency or frequency range that the transducers of the catheter or transducer-based device 200, 300, or 400 are configured to sense as, e.g., respective Z-axis locations of the respective transducers. The first, second, and third frequencies or frequency ranges may be mutually exclusive, according to some embodiments. In some embodiments, the first, second, and third electric fields may have a same frequency or frequency range and be time-multiplexed in coordination with time-multiplexed sensing by the transducers of the catheter or transducer-based device 200, 300, or 400, to facilitate repeated sequential sensing of respective X, Y, and Z-axis locations of the respective transducers. Electric field strength sensed by transducer(s) of the catheter or transducer-based device 200, 300, or 400 may be evaluated by the controller 324 or its data processing device system 310 to determine respective three-dimensional X, Y, and Z-axis locations of the transducers with respect to the first, second, and third electric fields and with respect to reference device 252 (shown as including reference electrodes 252a, 252b, 252c, and 252d, although fewer or more may be provided), according to some embodiments. The reference device 252 may be located within the body of the patient 361, preferably in a location that keeps its positioning relatively stable, such as in the coronary sinus, to factor out transitory movements of the transducer(s) of the transducer-based device 200, 300, or 400 due, e.g., to the beating of the heart. The one or more reference electrodes (e.g., reference electrodes 252a, 252b, 252c, and 252d) of the reference device 252 also sense electric field strength of the first, second, and third electric fields, and the three dimensional location of the transducer-based device 200, 300, or 400 is determined by the controller 324 or its data processing device system 310 with respect to the reference device 252 based on the measurements made by the transducers of the catheter or transducer-based device 200, 300, or 400 and the measurements made by the reference electrodes (e.g., reference electrodes 252a, 252b, 252c, and 252d) of the reference device 252, according to some embodiments. U.S. Pat. No. 5,697,377, issued on Dec. 16, 1997 to Frederik H. M. Wittkampf, which is hereby incorporated herein by reference, provides examples of how to determine a three-dimensional location of a catheter electrode position.

In this regard, FIG. 2 illustrates a catheter navigation system that may include a catheter (e.g., transducer-based device 200, 300, or 400) including a plurality of transducers (discussed in more detail below), a catheter-device-location tracking system, which may include one or more external electrodes (e.g., electrodes 256a, 256b, 256c, 256d, 256e, and 256f), one or more reference electrodes (e.g., reference electrodes 252a, 252b, 252c, 252d of reference device 252), the controller 324 or data processing system 310 or 110, the transducers of the catheter (e.g., transducer-based device 200, 300, or 400), and a display device system (e.g., display device system 332), according to various embodiments. In some embodiments, the display device system, the catheter, the catheter-device-location tracking system, or a combination thereof may be included as part of an input-output device system (e.g., input-output device system 320 or input-output device system 120) of the catheter navigation system.

Figure 3:
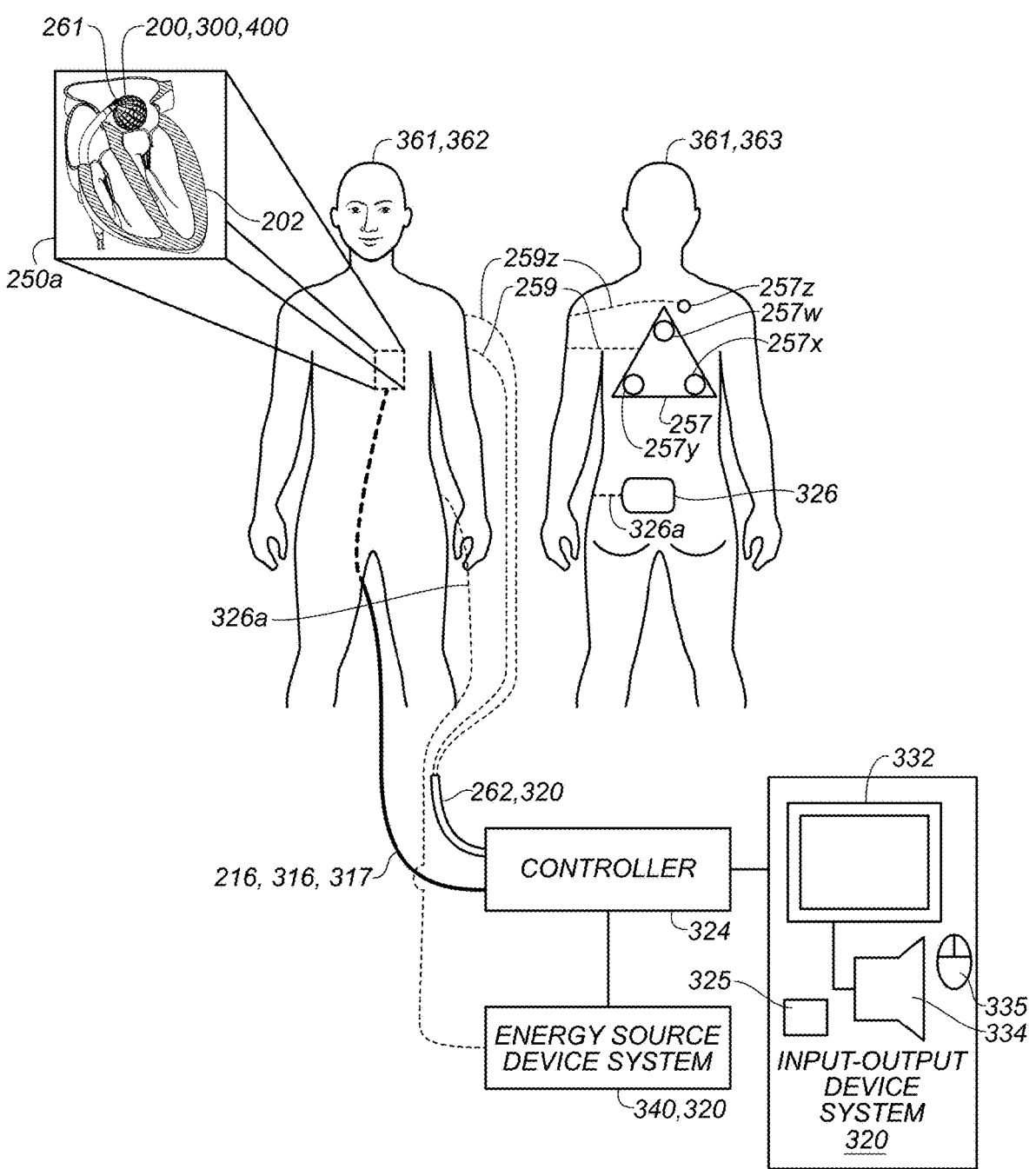
FIG. 3 includes a partially schematic representation of some particular implementations of the catheter navigation system of FIG. 1 implementing a magnetic-field-based location system, according to various example embodiments.

FIG. 3 includes a partially schematic representation of some particular implementations of the catheter navigation system of FIG. 1 implementing a magnetic-field-based location system, according to various example embodiments. In this regard, FIG. 3 corresponds to FIG. 2, except that a magnetic-field-based location system is illustrated instead of an electric-field-based location system. Instead of electrodes 256a, 256b, 256c, 256d, 256e, and 256f, FIG. 3 illustrates three magnetic field generation sources 257w, 257x, 257y, such as coils, each of which respectively generates a magnetic field, according to some embodiments. The magnetic field generation sources 257w, 257x, and 257y may be integrally formed within a package or frame 257 located beneath the patient 361. Magnetic field sources 257w, 257x, 257y may respectively be connected to the controller 324 via a set of one or more conductors 259, which may or may not be located within the same cable 262. The transducer-based device 200, 300, 400 may include one or more magnetic field transducers 261 (shown in the cut-out illustration window 250a in FIG. 3) configured to sense the strengths of the magnetic fields generated by magnetic field sources 257w, 257x, and 257y. As with some embodiments associated with FIG. 2, the magnetic field sources 257w, 257x, and 257y need not generate different magnetic fields, but may instead generate the same magnetic fields in a time-multiplexed manner that are sensed in sequence over time by the one or more magnetic field transducers 261. In some embodiments, the one or more magnetic field transducers 261 may sense the magnetic field strengths with respect to a reference device 257z, which may be akin to the reference device 252 in the electric field context of FIG. 2. With the three magnetic field strengths detected by the one or more magnetic field transducers 261 for a given time or time period, the distance(s) between the one or more transducers 261 and the magnetic field generation sources 257w, 257x, and 257y may be determined, and the three-dimensional location of the one or more transducers 261 may be determined according to triangulation according to some embodiments. With the location of the one or more transducers 261 in three-dimensional space known, and the geometry of the transducer-based device 200, 300, 400 (e.g., including the locations of the transducers on the transducer-based device) relative to transducers 261 also known, the locations of the transducers of the transducer-based device 200, 300, 400 for the given time or time period may be determined, according to some embodiments. U.S. Patent Application Publication No. 2007/0265526 (Govan et al.), published on Nov. 15, 2007, which is hereby incorporated herein by reference, provides examples of how to determine a three-dimensional location of a catheter in a magnetic-field-based system.

Figure 4:
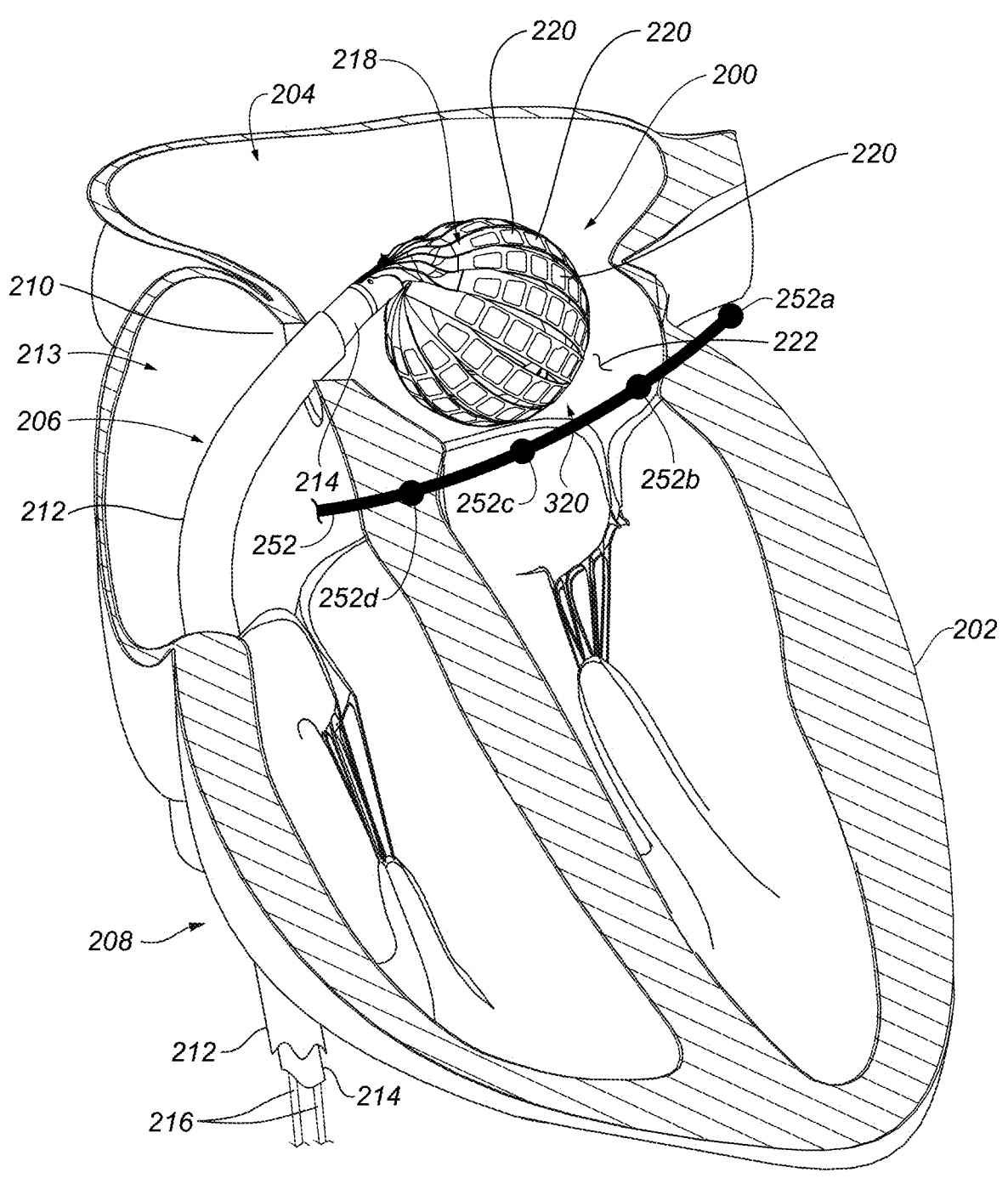
FIG. 4 includes a cutaway diagram of a heart showing a catheter navigation system including a reference device and a transducer-based device, the reference device part of a catheter-device-location tracking system and percutaneously placed at least proximate a heart cavity, and the transducer-based device percutaneously placed in a left atrium of the heart, according to various example embodiments.

FIG. 4 is a representation of a transducer-based device 200 useful in investigating or treating a bodily organ, for example, a heart 202, according to some embodiments.

Transducer-based device 200 can be percutaneously or intravascularly inserted into a portion of the heart 202, such as an intracardiac cavity, like left atrium 204. In this example, the transducer-based device 200 is part of a catheter 206 inserted via the inferior vena cava 208 and penetrating through a bodily opening in transatrial septum 210 from right atrium 213. (In this regard, transducer-based devices or device systems described herein that include a catheter may also be referred to as catheter device systems, catheter devices or device systems, or catheter-based devices or device systems, according to various embodiments.) In other embodiments, other paths may be taken.

Catheter 206 includes an elongated flexible rod or shaft member appropriately sized to be delivered percutaneously or intravascularly. Various portions of catheter 206 may be steerable. For example, a structure 218 supporting transducers 220 may be controlled via various manipulations to advance outwardly, to retract, to rotate clockwise, to rotate counterclockwise, and to have a particular deployment plane orientation (e.g., a plane in which the structure progresses from a delivery configuration (e.g., described below with respect to at least FIG. 5) to or at least toward a deployed configuration (e.g., described below with respect to at least FIG. 6), according to some embodiments. One or more other portions of the transducer-based device 200 may be steerable. For example, a catheter sheath 212, which encompasses or surrounds at least part of an elongate shaft member 214 to which the structure 218 is physically coupled, may be steerable. In some embodiments, the sheath 212 may be controlled via various manipulations to advance outwardly, retract, rotate clockwise, rotate counterclockwise, bend, release a bend, and have a particular bending plane orientation, according to some embodiments.

Catheter 206 may include one or more lumens. The lumen(s) may carry one or more communications or power paths, or both. For example, the lumens(s) may carry one or more electrical conductors 216 (two shown). Electrical conductors 216 provide electrical connections to transducer-based device 200 and transducers 220 thereof that are accessible externally from a patient in which the transducer-based device 200 is inserted.

Transducer-based device 200 may include a frame or structure 218 which assumes an unexpanded configuration for delivery to left atrium 204, according to some embodiments, such frame or structure supporting transducers. Structure 218 is expanded (e.g., shown in a deployed or expanded configuration in FIG. 4) upon delivery to left atrium 204 to position a plurality of transducers 220 (three called out in FIG. 4) proximate the interior surface formed by tissue 222 of left atrium 204. In some embodiments, at least some of the transducers 220 are configured to sense a physical characteristic of a fluid (e.g., blood) or tissue 222, or both, that may be used to determine tissue contact. In some embodiments, at least some of the transducers 220 may be configured to selectively ablate portions of the tissue 222. For example, some of the transducers 220 may be configured to ablate a pattern around the bodily openings, ports, or pulmonary vein ostia, for instance, to reduce or eliminate the occurrence of atrial fibrillation. In some embodiments, at least some of the transducers 220 are configured to ablate cardiac tissue. In some embodiments, at least some of the transducers 220 are configured to sense or sample intracardiac voltage data or sense or sample intracardiac electrogram data. In some embodiments, at least some of the transducers 220 are configured to sense or sample intracardiac voltage data or sense or sample intracardiac electrogram data while at least some of the transducers 220 are concurrently ablating cardiac tissue. In some embodiments, at least one of the sensing or sampling transducers 220 is provided by at least one of the ablating transducers 220. In some embodiments, at least a first one of the transducers 220 senses or samples intracardiac voltage data or intracardiac electrogram data at a location at least proximate to a tissue location ablated by at least a second one of the transducers 220. In some embodiments, the first one of the transducers 220 is other than the second one of the transducers 220.

Figure 5:
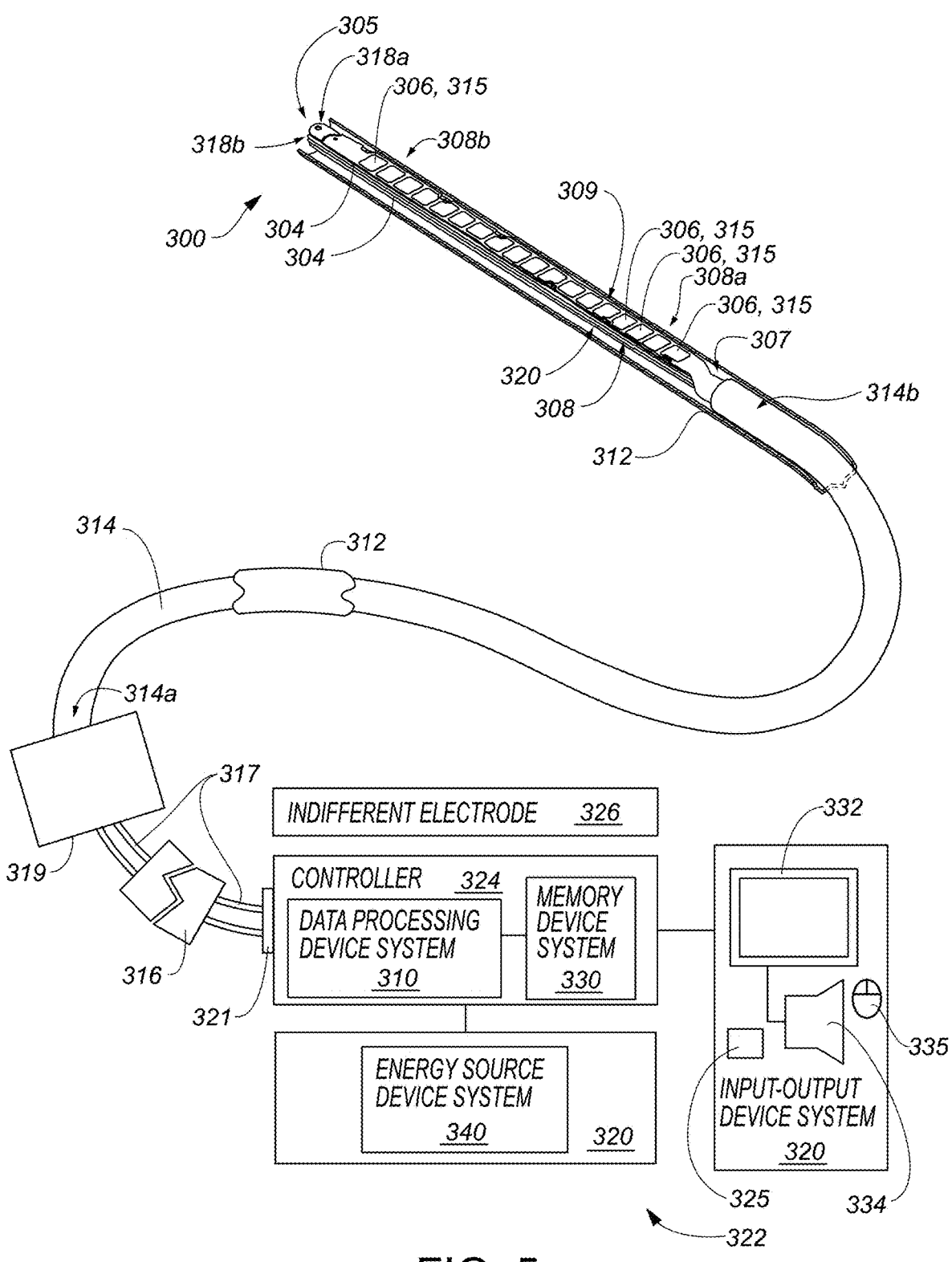
FIG. 5 includes a partially schematic representation of at least a portion of a catheter navigation system according to various example embodiments, the catheter navigation system including a data processing device system, an input-output device system, a memory device system, and a transducer-based device, the transducer-based device including a plurality of transducers and an expandable structure shown in a delivery or unexpanded configuration, according to various example embodiments.
Figure 6:
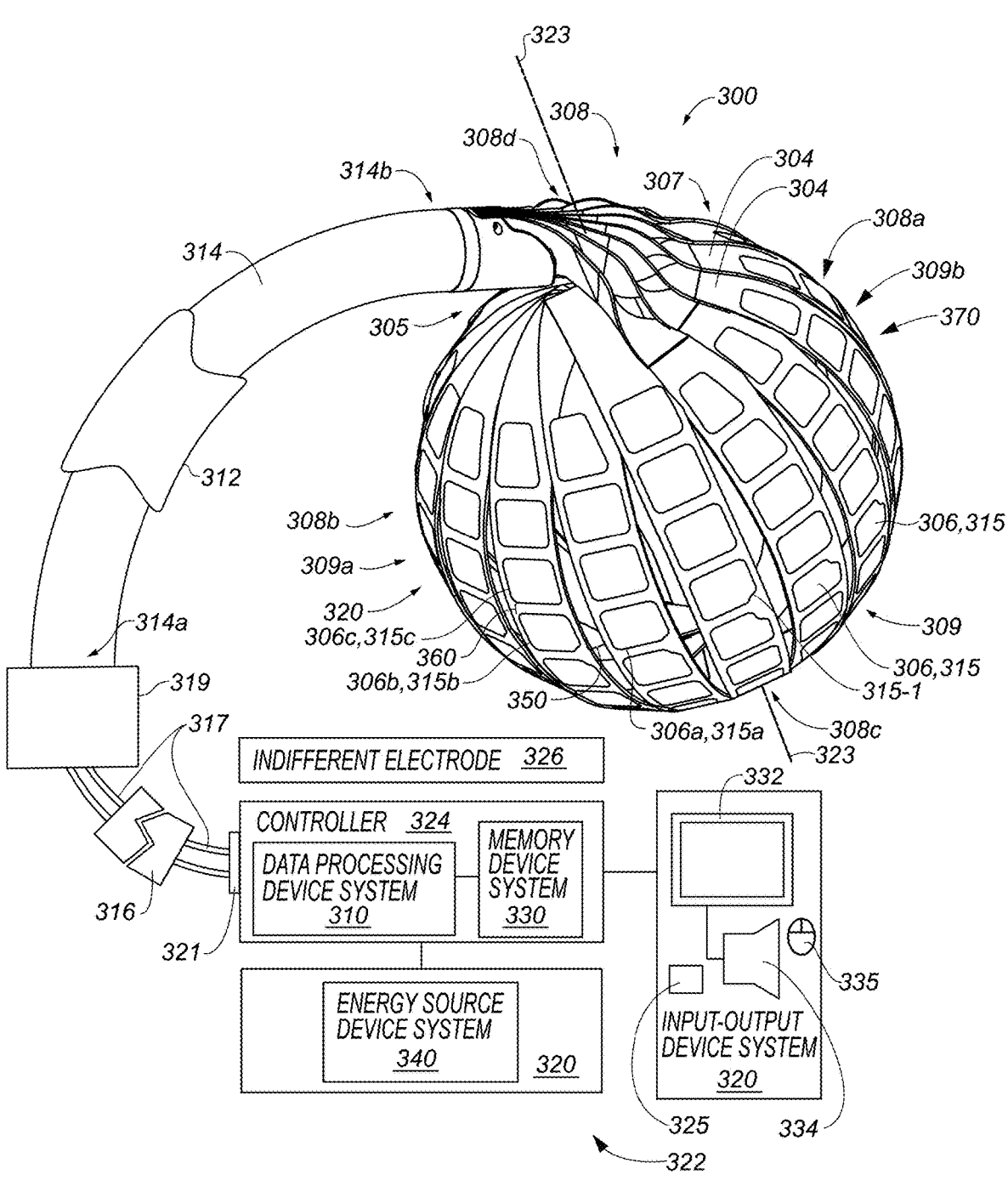
FIG. 6 includes the representation of the portion of the catheter navigation system of FIG. 5 with the expandable structure shown in a deployed or expanded configuration, according to various example embodiments.

FIGS. 5 and 6 include a catheter device system (e.g., a portion thereof shown schematically) that includes a transducer-based device 300, according to some embodiments. The transducer-based device 300 may be the same as the transducer-based device 200, although different sizes, numbers of transducers, or types of transducer-based devices, such as balloon catheters, may be implemented. In this regard, transducer-based device 300 includes a plurality of elongate members 304 (not all of the elongate members are called out in FIGS. 5 and 6) and a plurality of transducers 306 (not all of the transducers called out in FIGS. 5 and 6) (some of the transducers 306 are called out in FIG. 6 as 306a, 306b, and 306c). FIG. 5 includes a representation of a portion of the transducer-based device 300 in a delivery or unexpanded configuration. FIG. 6 includes a representation of a portion of the transducer-based device 300 in an expanded of deployed configuration. It is noted that, for clarity of illustration, all of the elongate members shown in FIG. 6 are not represented in FIG. 5. As will become apparent, the plurality of transducers 306 is positionable within a bodily cavity, such as with the transducer-based device 200. For example, in some embodiments, the transducers 306 are able to be positioned in a bodily cavity by movement into, within, or into and within the bodily cavity, with or without a change in a configuration of the plurality of transducers 306. In some embodiments, the transducers of the plurality of transducers 306 are arranged to form a two- or three-dimensional distribution, grid or array of the transducers capable of mapping, ablating, or stimulating an inside surface of a bodily cavity or lumen without requiring mechanical scanning. As shown, for example, in FIG. 5, the plurality of transducers 306 are arranged in a distribution receivable in a bodily cavity. In FIGS. 5 and 6, each of at least some of transducers 306 includes a respective electrode 315 (not all of the electrodes 315 are called out in FIGS. 5 and 6.

The elongate members 304 are arranged in a frame or structure 308 that is selectively movable between an unexpanded or delivery configuration (e.g., as shown in FIG. 5) and an expanded or deployed configuration (e.g., as shown in at least FIG. 6) that may be configured to position elongate members 304 against a tissue surface within the bodily cavity or position the elongate members 304 in the vicinity of the tissue surface. In some embodiments, structure 308 has a size in the unexpanded or delivery configuration suitable for delivery through a bodily opening (e.g., via catheter sheath 312) to the bodily cavity. In various embodiments, catheter sheath 312 typically includes a length sufficient to allow the catheter sheath to extend between a location at least proximate a bodily cavity into which the structure 308 is to be delivered and a location outside a body comprising the bodily cavity. In some embodiments, structure 308 has a size in the expanded or deployed configuration too large for delivery through a bodily opening (e.g., via catheter sheath 312) to the bodily cavity. The elongate members 304 may form part of a flexible circuit structure (e.g., also known as a flexible printed circuit board (PCB) circuit, examples of which are described with respect to FIG. 7, below). The elongate members 304 may include a plurality of different material layers. Each of the elongate members 304 may include a plurality of different material layers. The structure 308 may include a shape memory material, for instance, Nitinol. The structure 308 may include a metallic material, for instance, stainless steel, or non-metallic material, for instance, polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (e.g., pose), or both of structure 308 in the bodily cavity, the requirements for successful ablation of a desired pattern, or the effect that the material may have on electric or magnetic fields to be sensed by the device (e.g., by one or more transducers 306 or one or more magnetic field transducers 261).

Figure 7:
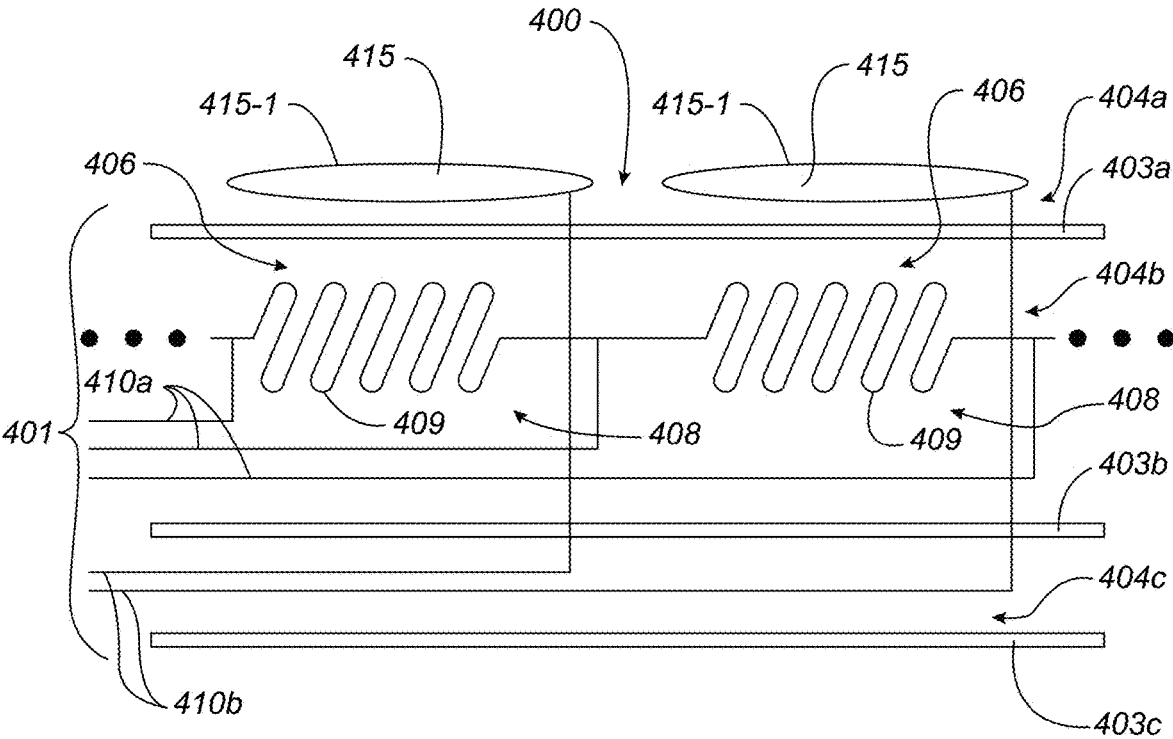
FIG. 7 includes a schematic representation of a transducer-based device of a catheter navigation system that includes a flexible circuit structure, according to various example embodiments.

FIG. 7 is a schematic side elevation view of at least a portion of a transducer-based device 400 that includes a flexible circuit structure 401 that is configured to provide a plurality of transducers 406 (two called out), according to some embodiments. In some embodiments, the flexible circuit structure 401 may form part of a structure (e.g., structure 308) that is selectively movable between a delivery configuration sized for percutaneous delivery and expanded or deployed configurations sized too large for percutaneous delivery. In some embodiments, the flexible circuit structure 401 may be located on, or form at least part of, a structural component (e.g., elongate member 304) of a transducer-based device system.

The flexible circuit structure 401 may be formed by various techniques including flexible printed circuit techniques. In some embodiments, the flexible circuit structure 401 includes various layers including flexible layers 403a, 403b and 403c (e.g., collectively flexible layers 403). In some embodiments, each of flexible layers 403 includes an electrical insulator material (e.g., polyimide). One or more of the flexible layers 403 may include a different material than another of the flexible layers 403. In some embodiments, the flexible circuit structure 401 includes various electrically conductive layers 404a, 404b and 404c (collectively electrically conductive layers 404) that are interleaved with the flexible layers 403. In some embodiments, each of the electrically conductive layers 404 is patterned to form various electrically conductive elements. For example, electrically conductive layer 404a may be patterned to form a respective electrode 415 of each of the transducers 406. Electrodes 415 may have respective electrode edges 415-1 that form a periphery of an electrically conductive surface associated with the respective electrode 415. It is noted that other electrodes employed in other embodiments may have electrode edges arranged to form different electrode shapes (for example, as shown by electrode edge 315-1 in FIG. 6).

Electrically conductive layer 404b is patterned, in some embodiments, to form respective temperature sensors 408 for each of the transducers 406, as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias in flexible layers 403a and 403b to connect with electrodes 415. Although FIG. 7 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and can be part of, e.g., elongate member 304. In some embodiments, the one or more structural layers may include at least one electrically conductive surface (e.g., a metallic surface) exposed to blood flow. In addition, although FIG. 7 shows only three flexible layers 403a-403c and only three electrically conductive layers 404a-404c, it should be noted that other numbers of flexible layers, other numbers of electrically conductive layers, or both, may be included.

In some embodiments, electrodes 415 are configured to selectively deliver RF energy to various tissue structures within a bodily cavity (e.g., an intracardiac cavity or chamber). The energy delivered to the tissue structures may be sufficient for ablating portions of the tissue structures. The energy delivered to the tissue may be delivered to cause monopolar tissue ablation, bipolar tissue ablation, or blended monopolar-bipolar tissue ablation by way of non-limiting example.

Energy that is sufficient for tissue ablation may be dependent upon factors including transducer location, size, shape, relationship with respect to another transducer or a bodily cavity, material or lack thereof between transducers, et cetera. For example, a pair of electrodes that each is approximately 10 mm² in surface area and present along a same structural member (e.g., an elongate member 304 in FIG. 4) may be expected, in some circumstances, to sufficiently ablate intracardiac tissue to a depth of approximately 3.1 mm with 2 W of power and to a depth of approximately 4.4 mm with 4 W of power. For yet another non-limiting example, if each electrode in this pair instead has approximately 20 mm² of surface area, it may be expected that such pair of electrodes will sufficiently ablate intracardiac tissue to a depth of approximately 3.1 mm with 4 W of power and to a depth of approximately 4.4 mm with 8 W of power. In these non-limiting examples, power refers to the average power of each electrode summed together, and the depth and power values may be different depending upon the particular shapes of the respective electrodes, the particular distance between them, a degree of electrode-to-tissue contact, and other factors. The degree of electrode-to-tissue contact has a bearing on the depth of the lesions formed with fuller or more complete contact typically leading to deeper lesions. It is understood, however, that for the same control or target temperature, a larger electrode will achieve a given ablation depth sooner than a smaller electrode. A smaller electrode (e.g., an electrode with a smaller surface area) may need to operate at a higher target temperature to achieve the same ablation depth as compared to a larger (e.g., surface area) electrode (a phenomenon driven by a greater divergence of heat flux of smaller electrodes). Put differently, a maximum ablation depth (e.g., reached when the temperature profile approaches steady state) of a relatively smaller electrode is typically shallower than that of a relatively larger electrode when ablating at the same control or target temperature, and consequently, a given, less than maximum, ablation depth typically is a larger proportion of the final, maximum, ablation depth for a relatively smaller electrode and typically is reached later in the ablation as compared to a relatively larger electrode. This circumstance may be associated with a lower total power provided to the relatively smaller electrode as compared to a relatively larger electrode, but, nonetheless, the power density present in the relatively smaller electrode may be expected to be somewhat higher as compared to the relatively larger electrode. The phrase "power density" in this context means output power divided by electrode area. Note that power density approximately drives the realized control or target temperature, but in various cases, this is a simplification, and as indicated above, the relationship between power density and realized control or target temperature may be modified by such factors as electrode size, shape, separation, and so forth. It is further noted that when a comparison is made between a relatively larger electrode operated at a lower control temperature versus a relatively smaller electrode operated at a higher temperature, further complications may arise when limits on compensation for electrode size with temperature are also dictated, at least in part, by a desire to reduce occurrences of thermal coagulation of blood or steam formation in the ablated tissue. It is noted that power levels in irrigated electrode systems are typically higher (e.g., in the tens of watts) than those described above. It is noted that the degree of electrode-to-tissue contact may impact other factors than lesion quality. For example, lesser degrees of electrode-to-tissue contact may lead to undesired increased levels of thermal coagulum formation in which at least a portion of the ablation energy is conveyed to blood rather than to tissue. In some cases, lesser degrees of electrode-to-tissue contact may cause undesired filtering of electric potential information (e.g., intracardiac voltage information). Such filtering may lead to the formation of intracardiac electrograms with reduced sharpness.

In some embodiments, each electrode 415 is configured to sense or sample an electric potential in the tissue proximate the electrode 415 at a same or different time than delivering energy sufficient for tissue ablation. In some embodiments, each electrode 415 is configured to sense or sample intracardiac voltage data in the tissue proximate the electrode 415. In some embodiments, each electrode 415 is configured to sense or sample data in the tissue proximate the electrode 415 from which an electrogram (e.g., an intracardiac electrogram) may be derived. In some embodiments, each resistive member 409 is positioned adjacent a respective one of the electrodes 415. In some embodiments, each of the resistive members 409 is positioned in a stacked or layered array with a respective one of the electrodes 415 to form a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive member 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow). The resistance data can thus be correlated to the degree of presence of the flow between the electrode 415 and tissue, thereby allowing the degree of contact between the electrode 415 and the tissue to be determined. Other methods of detecting transducer-to-tissue contact or degrees of transducer-to-tissue contact may be employed according to various example embodiments.

Referring to FIGS. 5 and 6, transducer-based device 300 can communicate with, receive power from or be controlled by a transducer-activation device system 322. In some embodiments, the transducer-activation device system 322 represents one or more particular implementations of the system 100 illustrated in FIG. 1. In some embodiments, elongate members 304 include transducers 306 that are communicatively connected to a data processing device system 310 via electrical connections running within elongate shaft member 314 that are communicatively connected to one or more of electrical leads 317 (e.g., control leads, data leads, power leads or any combination thereof) within elongated cable 316 (only a portion of which is shown in FIGS. 5 and 6 to reveal other structures) terminating at a connector 321 or other interface. The leads 317 may correspond to the electrical conductors 216 in FIG. 4 in some embodiments and, although only two leads 317 are shown for clarity, more may be present. The transducer-activation device system 322 may include a controller 324 that includes the data processing device system 310 (e.g., which may be a particular implementation of data processing device system 110 from FIG. 1) and a memory device system 330 (e.g., which may be a particular implementation of the memory device system 130 from FIG. 1) that stores data and instructions that are executable by the data processing device system 310 to process information received from transducer-based device 300 or to control operation of transducer-based device 300, for example, activating various selected transducers 306 to ablate tissue and control a user interface (e.g., of input-output device system 320) according to various embodiments including at least those described below with respect to various ones of FIGS. 8-13. Controller 324 may include one or more controllers.

Transducer-activation device system 322 includes an input-output device system 320 (e.g., which may be a particular implementation of the input-output device system 120 from FIG. 1) communicatively connected to the data processing device system 310 (e.g., via controller 324 in some embodiments). Input-output device system 320 may include a user-activatable control that is responsive to a user action. Input-output device system 320 may include one or more user interfaces or input/output (I/O) devices, for example one or more display device systems 332, speaker device systems 334, one or more keyboards, one or more mice (e.g., mouse 335), one or more joysticks, one or more track pads, one or more touch screens or other transducers to transfer information to, from, or both to and from a user, for example a care provider such as a physician or technician. For example, output from a mapping process (e.g., such as those illustrated in FIGS. 8-13) may be displayed by a display device system 332. Input-output device system 320 may include one or more user interfaces or input/output (I/O) devices, for example, one or more display device systems 332, speaker device systems 334, keyboards, mice, joysticks, track pads, touch screens or other transducers employed by a user to indicate a particular selection or series of selections of various graphical information. Input-output device system 320 may include a sensing device system 325 configured to detect various characteristics including, but not limited to, at least one of tissue characteristics (e.g., electrical characteristics such as tissue impedance, electric potential of a tissue surface, tissue conductivity, tissue type, tissue thickness) and thermal characteristics such as temperature. In this regard, the sensing device system 325 may include one, some, or all of the transducers 306 (or 220 in FIG. 4 or 406 of FIG. 7) of the transducer-based device 300, including the internal components of such transducers shown in FIG. 7, such as the electrodes 415 and temperature sensors 408.

Transducer-activation device system 322 may also include an energy source device system 340 including one or more energy source devices connected to transducers 306. In this regard, although FIGS. 5 and 6 show a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body or elongate shaft member 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

The energy source device system 340 may, for example, be connected to various selected transducers 306 to selectively provide energy in the form of electrical current or power (e.g., RF energy), light or low temperature fluid to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include various electrical current sources or electrical power sources as energy source devices. In some embodiments, an indifferent electrode 326 is provided to receive at least a portion of the energy transmitted by at least some of the transducers 306. Consequently, although not shown in FIGS. 5 and 6, the indifferent electrode 326 may be communicatively connected to the energy source device system 340 via one or more communication lines in some embodiments. In addition, although shown separately in each of FIGS. 5 and 6, indifferent electrode 326 may be considered part of the energy source device system 340 in some embodiments. In various embodiments, indifferent electrode 326 is positioned on an external surface (e.g., a skin-based surface) of a body that comprises the bodily cavity into which at least transducers 306 are to be delivered.

It is understood that input-output device system 320 may include other systems. In some embodiments, input-output device system 320 may optionally include energy source device system 340, transducer-based device 300 or both energy source device system 340 and transducer-based device 300 by way of non-limiting example. Input-output device system 320 may include the memory device system 330 in some embodiments.

Structure 308 may be delivered and retrieved via a catheter member, for example, a catheter sheath 312. In some embodiments, a structure provides expansion and contraction capabilities for a portion of the medical device (e.g., an arrangement, distribution or array of transducers 306). The transducers 306 may form part of, be positioned or located on, mounted or otherwise carried on the structure and the structure may be configurable to be appropriately sized to slide within catheter sheath 312 in order to be deployed percutaneously or intravascularly. FIGS. 5 and 6 show one embodiment of such a structure. In some embodiments, each of the elongate members 304 includes a respective distal end 305 (only one called out in each of FIGS. 5 and 6), a respective proximal end 307 (only one called out in each of FIGS. 5 and 6) and an intermediate portion 309 (only one called out in each of FIGS. 5 and 6) positioned between the proximal end 307 and the distal end 305. The respective intermediate portion 309 of each elongate member 304 includes a first or front surface 318a that is positionable to face an interior tissue surface within a bodily cavity and a second or back surface 318b opposite across a thickness of the intermediate portion 309 from the front surface 318a. In some embodiments, each of the elongate members 304 is arranged front surface 318a-toward-back surface 318b in a stacked array during an unexpanded or delivery configuration similar to that described in co-assigned International Application No.: PCT/US2012/022061 and co-assigned International Application No.: PCT/US2012/022062. In many cases a stacked array allows the structure 308 to have a suitable size for percutaneous or intravascular delivery. In some embodiments, the elongate members 304 are arranged to be introduced into a bodily cavity distal end 305 first. An elongate shaft member 314 is configured to deliver structure 308 through catheter sheath 312, according to some embodiments. According to various embodiments, the elongate shaft member 314 includes a proximal end portion 314a and a distal end portion 314b, the distal end portion 314b physically coupled to structure 308. According to various embodiments, the elongate shaft member 314 may include a length to position distal end portion 314b (and structure 308 in some embodiments) at a desired location within a patient's body while maintaining the proximal end portion 314a at a location outside the patient's body. In some embodiments, the proximal end portion 314a may be coupled to a housing 319. Housing 319 may include or enclose various actuators (not shown) that may be configured to manipulate various portions of the catheter, including, but not limited to, (a) portions of the elongate shaft member 314, portions of structure 308, or both (a) and (b). According to various embodiments, housing 319 may take the form of a handle that is directly manipulable by a user. U.S. Pat. No. 9,452,016, issued Sep. 27, 2016, which is hereby incorporated herein by reference, provides possible examples of a housing and accompanying actuators that may be utilized as housing 319.

In this regard, various actuators provided by housing 319 may be coupled by various control elements (e.g., control lines, push-pull members, etc.) configured to convey manipulation force to at least structure 308 and sheath 312. Manipulation of portions of structure 308 may include particular manipulation causing movement, at least in part, of the structure 308 between a delivery configuration (e.g., FIG. 5) and a deployed configuration (e.g., FIGS. 4 and 6), according to some embodiments. Manipulation of portions of structure 308 may include particular manipulation causing movement (e.g., advancement (which may include a movement distally or may include a movement toward the deployed configuration), retraction (which may include a movement proximally or may include a movement toward the delivery configuration), and rotation) of one or more of the elongate members 304, according to some embodiments. Rotational movement of the structure 308 may control an orientation of a deployment or retraction plane of the structure 308 as it proceeds from the delivery configuration to the deployed configuration, or vice versa, according to some embodiments. U.S. Pat. No. 9,452,016, issued Sep. 27, 2016, which is hereby incorporated herein by reference, provides possible examples of how elongate members, such as elongate members 304 in FIG. 4, may depart a delivery configuration by proceeding into a planar coil shape before expanding into a fully deployed configuration, and how such elongate members may return from the fully deployed configuration into a planar coil shape during retraction into a catheter sheath to the delivery configuration, according to some embodiments.

According to some embodiments, manipulation of one or more portions of the sheath 312 may occur by way of one or more actuators that may extend from housing 319 through at least a portion of the sheath 312. U.S. Pat. No. 8,123,721, issued Feb. 28, 2012 to Troy T. Tegg, which is hereby incorporated herein by reference, provides examples of how such actuators may be included in a wall of a catheter shaft member, which may be implemented as elongate sheath 312 (or elongate shaft member 314), according to some embodiments. International Publication No. WO 2017/100902, published Jun. 22, 2017 provides other examples, according to some embodiments. Manipulation of the portions of the sheath 312 may include particular manipulation causing bending of various portions of elongate sheath 312, according to some embodiments. Bending of the sheath 312 may cause bending of the shaft 314 (e.g., when at least part of the shaft 314 is located with a lumen of the sheath 312) and, therefore, bending of the shaft 314 may be controlled by bending of the sheath 312, according to some embodiments. In other embodiments, bending of the shaft 314 may occur directly via one or more actuators coupled to the shaft 314. Bending of various portions of sheath 312 or the shaft 314 may be motivated for different reasons. For example, bending may be employed to facilitate steering the sheath 312 or the elongate shaft member 314 through a tortuous path within the body as often arises in intravascular or percutaneous procedures. Bending of various portions of the sheath 312 or the elongate shaft member 314 may also be employed to facilitate orienting structure 308 in a desired orientation. Bending of various portions of the sheath 312 or the elongate shaft member 314 may occur in a single plane, according to some embodiments. Bending of various portions of the sheath 312 or the elongate shaft member 314 may occur in each of multiple non-parallel planes in other embodiments.

In a manner similar to that described in co-assigned International Application No.: PCT/US2012/022061 and co-assigned International Application No.: PCT/US2012/022062, each of the elongate members 304 is arranged in a fanned arrangement 370 in at least FIG. 6, according to some embodiments. In some embodiments, the fanned arrangement 370 is formed during the expanded or deployed configuration in which structure 308 is manipulated to have a size too large for percutaneous or intravascular delivery.

In some embodiments, the transducers of the plurality of transducers (e.g., at least a group of the transducers 306) may be circumferentially arranged about an axis (e.g., 323, FIG. 6) of the structure 308 at least in the state in which the structure 308 is in the deployed configuration, the axis intersecting both the first portion of the structure (e.g., portion 308c in FIG. 6) and the second portion of the structure (e.g., portion 308d in FIG. 6) in the state in which the structure 308 is in the deployed configuration. According to various embodiments, portions 308c and 308d may each include a respective polar region of the structure 308 in the deployed configuration.

In some embodiments, the first portion of the structure 308 includes a first domed shape at least in the state in which the structure 308 is in the deployed configuration, and the second portion of the structure 308 includes a second domed shape at least in the state in which the structure 308 is in the deployed configuration, the second domed shape opposing the first domed shape at least in the state in which structure 308 is in the deployed configuration. For example, in FIG. 6, structure 308 includes multiple sets of opposing first and second portions, the first and the second portions including respective domed shapes that oppose one another (e.g., opposing hemisphere-like shapes) at least in the state in which the structure 308 is in the deployed configuration. In some embodiments, distal portion 308b includes a first domed shape 309a and proximal portion 308a includes a second domed shape 309b. In some embodiments, the first domed shape 309a opposes the second domed shape 309b.

In some embodiments, the proximal and the distal portions 308a, 308b each include respective portions of elongate members 304. In some embodiments, the structure 308 is arranged to be delivered distal portion 308b first into a bodily cavity at least in a state in which the structure is in the unexpanded or delivery configuration as shown in at least FIG. 5. In various embodiments, the proximal and distal portions 308a, 308b do not include a domed shape in the delivery configuration (for example, as shown in FIG. 5). In some embodiments, the first domed shape 309a of the distal portion 308b and the second domed shape 309b of the proximal portion 308a are arranged in a clam shell configuration in the expanded or deployed configuration shown in at least FIG. 6.

The transducers 306 can be arranged in various distributions or arrangements in various embodiments. In some embodiments, various ones of the transducers 306 are spaced apart from one another in a spaced apart distribution in the delivery configuration shown in FIG. 5. In some embodiments, various ones of the transducers 306 are arranged in a spaced apart distribution in the deployed configuration shown in at least FIG. 6. In some embodiments, various pairs of transducers 306 are spaced apart with respect to one another. In some embodiments, various regions of space are located between various pairs of the transducers 306. For example, in FIG. 6 the transducer-based device 300 includes at least a first transducer 306a, a second transducer 306b, and a third transducer 306c (all collectively referred to as transducers 306). In some embodiments, each of the first, the second, and the third transducers 306a, 306b, and 306c are adjacent transducers in the spaced apart distribution. In some embodiments, the first and the second transducers 306a, 306b are located on different elongate members 304, while the second and the third transducers 306b, 306c are located on a same elongate member 304. In some embodiments, a first region of space 350 is between the first and the second transducers 306a, 306b. In various embodiments, a first region of space 350 is between the respective electrodes 315a, 315b of the first and the second transducers 306a, 306b. In some embodiments, the first region of space 350 is not associated with any physical portion of structure 308. In some embodiments, a second region of space 360 associated with a physical portion of device 300 (e.g., a portion of an elongate member 304) is between the second and the third transducers 306b, 306c (and their respective electrodes 315b, 315c). In various embodiments, the second region of space 360 is between the respective electrodes 315b, 315c of the second and the third transducers 306b, 306c. In some embodiments, each of the first and the second regions of space 350, 360 does not include a transducer of transducer-based device 300. In some embodiments, each of the first and the second regions of space 350, 360 does not include any transducer. It is noted that other embodiments need not employ a group of elongate members 304 as employed in the illustrated embodiment. For example, other embodiments may employ a structure having one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device such as a transducer-based catheter. For example, an elongated catheter member may be used to distribute the transducers in a linear or curvilinear array.

Basket catheters or balloon catheters may be used to distribute the transducers in a two-dimensional or three-dimensional array.

According to some embodiments, a system is provided that may include an input-output device system (e.g., 120, 320) that may, in some embodiments, include a catheter that includes a plurality of transducers (e.g., transducers 220, 306, 406). The catheter may include the catheter body to which the plurality of transducers (or the structure on which the transducers reside) is physically coupled (e.g., catheter 206, and elongate shaft member 314). In some embodiments, the catheter may also include other components such as catheter sheath 312. According to various embodiments, different portions of the catheter are manipulable to in turn manipulate various ones of the plurality of transducers (e.g., transducers 220, 306, 406) into various degrees of contact with a tissue wall within a patient's body (e.g., patient 361). According to various embodiments, at least some transducers (e.g., at least some of the transducers 220, 306, 406), such as a first set of transducers, of the plurality of transducers of the catheter device system are arranged in a first spatial distribution (e.g., the spaced apart distribution associated with the deployed configuration of FIG. 6), the distribution positionable in a bodily cavity of a patient. The bodily cavity is defined by at least a tissue wall, and, according to various embodiments, each transducer of the at least some transducers, such as at least the first set of transducers, of the plurality of transducers is configured at least to sense a degree of contact between the transducer and the tissue wall. In some embodiments, each particular transducer of the at least some transducers (e.g., at least the first set of transducers) of the plurality of transducers of the catheter may be configured to sense or detect a degree of transducer-to-tissue contact between at least a portion of the particular transducer and the tissue wall. Various methods may be executed to determine the degree of transducer-to-tissue contact including, by way of non-limiting example, techniques including sensing impedance, sensing permittivity, sensing the presence or absence of flow of a fluid (e.g., a bodily fluid), or by sensing contact force or pressure. U.S. Pat. No. 8,906,011, issued Dec. 9, 2014, which is hereby incorporated herein by reference, describes example transducer sensing techniques. In some embodiments, the tissue-contacting portion of the transducer itself directly senses the degree of tissue contact. In some embodiments, a portion of the transducer other than the tissue-contacting portion of the transducer is configured to sense the degree of contact between the tissue wall and the tissue-contacting portion of the transducer. In some embodiments, the tissue-contacting portion of the transducer is provided by an electrode.

According to some embodiments, the at least some transducers (e.g., at least the first set of transducers) of the plurality of transducers of the catheter (e.g., transducer-based device 200 or transducer-based device 300) may be configured to provide a plurality of contact signal sets to the controller 324 or its data processing device system 310. Each contact signal set may indicate a degree of transducer-to-tissue contact between each transducer (e.g., a transducer 220, 306, 406) and a tissue surface in the bodily cavity.

In some embodiments, at least some transducers (e.g., at least some of the transducers 220, 306, 406), such as a second set of transducers, of the plurality of transducers of the catheter are configured to sense one or more electrical properties or characteristics of or generated at least in part by a body (e.g., the body of the patient 361) including the bodily cavity. In some embodiments, such transducers (e.g., at least the second set of transducers) may be configured to provide a plurality of tissue-electrical-information signal sets to the controller 324 or its data processing device system 310. In some embodiments, such transducers (e.g., at least the second set of transducers) may be configured to provide a plurality of tissue-electrical-information signal sets to the controller 324 or its data processing device system 310 throughout movement of at least a portion of the catheter (e.g., transducer-based device 200 or transducer-based device 300) among a sequence of locations of the at least the portion of the catheter in the bodily cavity. In some embodiments, the plurality of tissue-electrical-information signal sets indicate an electrical property set of or associated at least in part with a body including the bodily cavity and detected by at least the second set of transducers. The electrical property set may be tissue electrical characteristics as discussed above, possibly including different electrical property types, such as electric potential or electrical impedance, e.g., as detected by the respective transducers (e.g., transducers 220, 306, 406). In some embodiments, the plurality of tissue-electrical-information signal sets are generated by and provided to (and consequently, are received by) the controller 324 or its data processing device system 310 at least in a state representative of the second set of transducers being located in the bodily cavity. The state representative of the second set of transducers being located in the bodily cavity may be a state in which the second set of transducers are actually located in the bodily cavity, or may be, e.g., a simulation state in which it is simulated, e.g., for quality-control, training, or testing, that the second set of transducers are located (but not actually located) in the bodily cavity. In some embodiments, the second set of transducers (which may be configured to sense one or more electrical properties or characteristics of or generated at least in part by a body) and the first set of transducers (which may be configured to sense or detect a degree of transducer-to-tissue contact between at least a portion of the respective transducer and the tissue wall) may be the same one or more transducers (e.g., transducers 220, 306, 406). In other embodiments, the first set of transducers, the second set of transducers, or the first and second sets of transducers include at least one transducer not included in the other set.

In some embodiments, one or more devices of the catheter-device-location tracking system shown in FIGS. 2 and 3 is or are configured to provide a plurality of location signal sets to (and consequently, received by) the controller 324 or its data processing device system 310. Each location signal set is indicative of a respective location in a sequence of locations at which at least a portion of a catheter has been sequentially located in a bodily cavity, according to some embodiments. For example, with respect to FIGS. 2 and 3, at least a portion of the catheter (e.g., transducer-based device 200, 300, or 400) may be moved or progressed through a sequence of locations in a chamber of the heart or other bodily cavity of the patient 361 (or through a quality-control, training, or testing environment) in the presence of an electric field set (e.g., one or more electric fields generated by the external electrodes 256a, 256b, 256c, 256d, 256e, 256f) or a magnetic field set (e.g., one or more magnetic fields generated by magnetic field generation sources 257w, 257x, 257y). As the portion of the catheter is moved through the sequence of locations, at least some of the catheter's transducers (e.g., transducers 220, 306, 406 (or, e.g., 261 in the case of magnetic-field-based systems)) may be configured to generate each location signal set as detected strengths of the respective field(s), which the controller 324 or its data processing device system 310 may then be configured to utilize to generate a three-dimensional location of the at least the portion of the catheter (e.g., transducer-based device 200, 300, or 400) or its transducers (e.g., transducers 220, 306, 406 (and, e.g., 261 in the case of magnetic-field-based systems)) for the respective location in the sequence of locations, according to some embodiments. In this regard, in some embodiments, the catheter-device-location tracking system may be deemed to include the respective transducer(s) (e.g., transducers 220, 306, 406 (or, e.g., 261 in the case of magnetic-field-based systems)) that detected the field strength(s), the field-generating devices (e.g., the external electrodes 256a, 256b, 256c, 256d, 256e, 256f in the case of electric field(s); and, e.g., magnetic field generation sources 257w, 257x, 257y in the case of magnetic field(s)), or both the respective transducers and the field-generating devices. In some embodiments, the controller 324 or its data processing device system 310 may be considered at least part of the catheter-device-location tracking system.

At least in light of the above discussion, in some embodiments, the catheter-device-location tracking system is or are configured to generate the plurality of location signal sets at least in response to one or more electric or magnetic fields producible by one or more devices of the catheter-device-location tracking system. In some embodiments, the one or more devices that generate the one or more electric or magnetic fields may be configured to operate outside a body including the bodily cavity, such as the external electrodes 256a, 256b, 256c, 256d, 256e, 256f in the case of electric field(s), and magnetic field generation sources 257w, 257x, 257y in the case of magnetic field(s). According to some embodiments, the electric or magnetic field sensing devices of the catheter (e.g., transducers 220, 306, 406 or one or more magnetic field transducers 261) are configured to generate the plurality of location signal sets at least in response to the one or more electric or magnetic fields producible by one or more devices of the catheter-device-location tracking system. In this regard, the catheter-device-location tracking system, in some embodiments, may include the transducers 220, 306, 406 (or, e.g., 261 in the case of magnetic-field-based systems) of the catheter that sense the one or more electric or magnetic fields and consequently generate the plurality of location signal sets. According to some embodiments, each transducer of at least some of the transducers of the catheter (e.g., transducer-based device 200, 300, or 400) is configured to not only sense an electric field for location determination purposes, but also to perform one or more other functions (e.g., ablation, pacing, tissue electric potential detecting or measuring, transducer-to-tissue contact detecting or measuring, etc.).

FIG. 14 shows a respective data generation and flow diagram, which may implement various embodiments of method 1400 by way of associated computer-executable instructions, according to some example embodiments. In various example embodiments, a memory device system (e.g., memory device system 130 or 330) is communicatively connected to a data processing device system (e.g., data processing device systems 110 or 310, otherwise stated herein as "e.g., 110, 310") and stores a program executable by the data processing device system to cause the data processing device system to execute various embodiments of method 1400 via interaction with at least one or more devices of a catheter-device-location tracking system, for example, one or more transducers of a transducer-based device (e.g., transducer-based devices 200, 300, or 400) operating within an electric or magnetic field generated by one or more external devices (e.g., electrodes 256a, 256b, 256c, 256d, 256e, 256f or magnetic field generation sources 257w, 257x, 257y). In this regard, various embodiments of the method 1400 are executed by a programmed data processing device system (e.g., 110, 310) of a catheter navigation system. In various embodiments, the program may include instructions configured to perform, or cause to be performed, various ones of the instructions associated with execution of various embodiments of method 1400. In some embodiments, method 1400 may include a subset of the associated blocks or additional blocks than those shown in FIG. 14. In some embodiments, method 1400 may include a different sequence indicated between various ones of the associated blocks shown in FIG. 14.

In some embodiments, block 1402 is associated with computer-executable instructions configured to cause the data processing device system (e.g., 110, 310) to receive, via the input-output device system (e.g., 120, 320), a plurality of location signal sets, which may originate from at least some transducers (e.g., transducers 220, 306, 406) of a catheter-device-location tracking system. As discussed above with respect to FIG. 2, each location signal set of the plurality of location signal sets may be indicative of a respective location in a sequence of locations at which at least a portion of the catheter has been sequentially located in a bodily cavity.

In some embodiments, block 1404 is associated with computer-executable instructions configured to cause the data processing device system (e.g., 110, 310) to receive, via the input-output device system (e.g., 120, 320), a plurality of contact signal sets from a first set of transducers (e.g., transducers 220, 306, 406) of the plurality of transducers of a catheter (e.g., transducer-based device 200, 300, or 400). Each contact signal set of the plurality of contact signal sets may indicate a degree of transducer-to-tissue contact between each transducer of the first set of transducers and a tissue surface within the bodily cavity, and each contact signal set may correspond to a respective location in the sequence of locations of the at least the portion of the catheter in the bodily cavity. In some embodiments, the degree of contact detected between at least one of the respective transducers of the plurality of transducers (e.g., transducers 220, 306, 406) and the tissue wall may indicate at least different levels of contact between the at least one of the respective transducers and the tissue wall. For example, in some embodiments, the respective contact signal(s) from at least one of the respective transducers may indicate different levels of tissue contact existing between a portion of the at least one of the respective transducers and the tissue wall. For example, transducers configured to sense impedance or sense the presence or absence of flow of a fluid (e.g., a bodily fluid) adjacent the transducer may produce various signals indicating different levels of contact between the transducer and the tissue wall. In some embodiments, the respective contact signal(s) from the at least one of the respective transducers may indicate different amounts of a tissue-contactable portion (e.g., an electrode) of the at least one of the respective transducers that is in contact with the tissue wall, each of the different amounts indicating contact between the tissue-contactable portion and the tissue wall.

At least some embodiments of the present invention improve upon percutaneous or intravascular medical procedures by providing improved catheter navigation systems and methods. According to some embodiments of the present invention, a catheter-device-location tracking system (e.g., such as that illustrated in FIG. 2), provides a plurality of location signal sets (e.g., according to block 1402 in FIG. 14) to a data processing device system (e.g., data processing device system 110, 310), and a plurality of transducers (e.g., transducers 220, 306, 406) of a transducer-based device (e.g., transducer-based device 200, 300, or 400), which may be part of the catheter-device-location tracking system, provide a plurality of contact signal sets (e.g., according to block 1404 in FIG. 14) to the data processing device system, which also may be part of the catheter-device-location tracking system. The plurality of location signal sets may be generated as a result of an interaction between transducers of the transducer-based device, a reference device (e.g., reference device 252 or reference device 257*z*), and an electric or magnetic field generated by a plurality of external devices (e.g., electrodes 256*a*, 256*b*, 256*c*, 256*d*, 256*e*, 256*f* or magnetic field generation sources 257*w*, 257*x*, 257*y*) on or near a patient's body or otherwise outside of the bodily cavity being investigated or treated. The plurality of location signal sets may be provided by the catheter-device-location tracking system while the transducer-based device is moving throughout the bodily cavity (e.g., as illustrated by window 250 in FIGS. 2 and 3) or in a quality-control, training, or testing environment in real time, informing the data processing device system of a sequence of three-dimensional locations of the transducer-based device and its transducers in real time. The plurality of contact signal sets may be generated based on an interaction of the transducers with a tissue surface of the bodily cavity (or some other surface, such as a silicone model of a bodily cavity, in a quality-control, training, or testing environment) to detect a degree of contact between each respective transducer and the surface. Such contact signal sets may also be provided to the data processing device system in real time, informing it of respective degrees of tissue contact detected by the respective transducers in real time. With the stream of location signal sets (e.g., according to block 1402) and the contact signal sets (e.g., according to block 1404), the data processing device system may be configured to generate a graphical representation of a sequence of progressive enlargements (e.g., by addition of newly modeled surface regions, some examples of which are illustrated in at least FIGS. 8-11, discussed below) of at least a portion of an envelope (e.g., a visual representation of at least an interior tissue surface) representing an interior volume of the bodily cavity (or a simulated bodily cavity, e.g., in a quality-control, training, or testing environment) as the transducer-based device moves throughout the cavity. As the transducer-based device continues to explore new locations in the cavity, the envelope is enlarged or refined in the graphical representation to represent new or revised surface regions of the bodily cavity revealed by the location signal sets and the contact signal sets from the transducer-based device's progression into the new locations, according to some embodiments. In this regard, an interior volume of the bodily cavity can be displayed to an operator in real time as it is being mapped, thereby allowing treatment to occur during the mapping process without having to wait until the entire bodily cavity is mapped prior to performing treatment, according to some embodiments.

In some embodiments, the graphical representation of the envelope representing an interior volume of the cavity may visually represent on its surface regions the various degrees of tissue contact that were detected by particular transducers when they contacted the corresponding tissue surfaces of the bodily cavity. At least FIGS. 8-11, discussed in more detail below, illustrate some examples of the various degrees of tissue contact visually represented on surface regions of the graphical representation of such an envelope, according to some embodiments. Such visual representation of the various degrees of tissue contact may inform the operator of surface regions that may, in the case of a visually represented low degree of tissue contact, need to be revisited by the transducer-based device with greater tissue contact to improve the mapped location of such surface regions. At least FIGS. 8-11, discussed in more detail below, illustrate relatively lower tissue contact with lighter-gray regions of the graphical representation of the envelope, according to some embodiments. Or, according to some embodiments, a visual representation of a region of no tissue contact surrounded, enclosed, or encircled by a region of sufficient tissue contact may indicate to the operator the location of a port or opening in the bodily cavity. At least FIGS. 8-11, discussed in more detail below, illustrate some examples of such ports visually represented as port representation 802 and port representation 804. Or, in some embodiments, a visual representation of a region of excessive tissue contact may indicate to the operator that the corresponding tissue surface was excessively stretched by the transducer-based device when it was mapped and, therefore, the operator may know to move the transducer-based device less aggressively in that region when treating it, for example, by tissue ablation, which may help reduce the risk of damaging tissue. At least FIGS. 8-11, discussed in more detail below, illustrate relatively higher tissue contact with darker-gray regions of the graphical representation of the envelope, according to some embodiments. In this regard, the visual representations according to various embodiments of the present invention facilitate navigation of the transducer-based device in a manner that produces a substantially uniform and moderate degree of tissue contact throughout the mapping process, in order to reflect an accurate representation of the tissue surface. On the other hand, a region of the visual representation of the tissue surface that reveals excessive or insufficient tissue contact may indicate that such region is distorted or relatively inaccurate of the actual location of the tissue surface, according to some embodiments.

In some embodiments, the data processing device system (e.g., data processing device system 110, 310), utilizing at least the location signal sets (e.g., received according to block 1402), concurrently displays a graphical representation of at least a portion of the transducer-based device (e.g., at least a portion of a catheter, such as, by way of non-limiting example, a portion of the catheter that includes at least one transducer) and the envelope representing the interior volume of the cavity. In some embodiments, the graphical representation of the at least the portion of the transducer-based device (illustrates a physical surface of the at least the portion of the transducer-based device (e.g., illustrated surfaces including surfaces of elongate members 304, or a surface of a balloon catheter in embodiments where the transducer-based device is a balloon structure). In some embodiments, the graphical representation of the at least the portion of the transducer-based device includes an illustrated surface that corresponds to both a physical surface of the transducer-based device and a region of space between physical surfaces of the transducer-based device. For example, at least FIG. 8, discussed in more detail below, illustrates a graphical representation of at least a portion of a transducer-based device as a solid structure, even though the actual transducer-based device 300 includes gaps between its elongate members 304, according to some embodiments. In some embodiments, the graphical representation of the at least the portion of the transducer-based device illustrates at least a physical surface of the at least the portion of the transducer-based device in an expanded or deployed configuration of the transducer-based device, such as that shown in at least FIGS. 8-13. In some embodiments, the graphical representation of the at least the portion of the transducer-based device is an idealized representation of the portion of the transducer-based device. In some embodiments, the graphical representation of the transducer-based device includes transducer graphical elements representing the transducers of the transducer-based device. At least FIGS. 8-13, discussed in more detail below, illustrate some examples of a concurrent display (e.g., via display device system 332) of graphical representations of the transducer-based device and the envelope, and in at least FIGS. 8-12A, the examples of the graphical representation of the transducer-based device includes graphical elements representing the transducers (e.g., transducers 220, 306, 406) of the transducer-based device (e.g., transducer-based device 200, 300, or 400).

In this regard, the operator is able to view the present location of the transducer-based device and, in some embodiments, its transducers, within the interior volume of the cavity, according to some embodiments. In some embodiments, the graphical representation of the transducer-based device is represented as moving and causing the above-discussed progressive enlargements of the envelope as the transducer-based device moves throughout the bodily cavity (e.g., examples of which are illustrated by the sequence of at least FIGS. 8-11), thereby providing the operator with an effective understanding of not only the present location of the transducer-based device in the bodily cavity by way of the graphical representation of the transducer-based device, but also the historical locations of the transducer-based device by way of the graphical representation of the at least the portion of the envelope.

In some embodiments, at least some of the progressive enlargements of the graphical representation of the envelope representing an interior volume of the cavity are produced with respect to a graphical representation of a pre-existing image or model, such as a CT scan, of the cavity, further assisting the operator to understand the state of development of the envelope, as well as potential future desired movements of the transducer-based device to more thoroughly and efficiently develop the envelope. At least FIG. 13, discussed in more detail below, illustrates an example of a display of the envelope and a CT scan of the cavity. In some embodiments, it may be preferable to not display the pre-existing image or model of the cavity until the envelope has been sufficiently developed to a point where it is clear which portion of the bodily cavity is being illustrated by the visual representation of the envelope to assist in registration of the pre-existing image or model and the envelope.

In some embodiments, the graphical representation of the transducer-based device and, in some embodiments, its transducers, may have visual characteristics that indicate the various degrees of cavity-surface contact detected by the transducers of the transducer-based device. At least FIGS. 8-11, discussed in more detail below, illustrate some examples where the graphical elements representing the transducers have visual characteristics, such as different colorings, to illustrate detected degrees of surface contact. In some embodiments, the visually indicated various degrees of tissue contact represent degrees of cavity-surface contact presently or currently detected by the transducers. Concurrently, in some embodiments, the graphical representation of the at least the portion of the envelope includes visual characteristics that indicate the various degrees of cavity-surface contact that were detected by the respective transducers when they mapped the respective regions of the cavity. At least FIGS. 8-11, discussed in more detail below, illustrate some examples of prior cavity-surface contact illustrated by, e.g., various colorings on a surface of the graphical representation of the envelope, and present cavity-surface contact illustrated by, e.g., various colorings on a surface of the graphical representation of the catheter, including the graphical elements representing the transducers of the catheter. Accordingly, in some embodiments, the operator is able to concurrently understand the present tissue-contact state exhibited by the transducers by viewing the graphical representation of the transducer-based device and the historical tissue-contact states exhibited by transducers in the past by viewing the graphical representation of the at least the portion of the envelope. In some embodiments, in addition to showing historical degrees of detected transducer-to-tissue contact via a surface of the graphical representation of the portion of the envelope (e.g., visual representation 806 in the example of FIG. 8), at least in regions where the at least the portion of the catheter is presently located, present or current degrees of detected transducer-to-tissue contact may be graphically represented on a surface of the visual representation of the portion of the catheter (e.g., catheter representation 808 in the example of FIG. 8) and with the transducer graphical elements. Further, in embodiments where present degrees of cavity-surface contact (or other property as elaborated upon otherwise herein) are illustrated by a surface of the graphical representation of the catheter, the surface of the graphical representation of the catheter may visually present to the user, variations over time of detected degrees of the cavity-surface contact (or other property as elaborated upon otherwise herein) across such surface, as illustrated by the sequence of different coloring patterns on the transducer-based device shown at least in FIGS. 8-11. For instance, in cases where the visually-represented surface of the catheter displays a detected electrical property, the visually-represented surface of the catheter may visually represent a propagation or variation over time of the various degrees of the detected electrical property across such surface.

In some embodiments, where overlapping graphical representations are displayed, such as a combination of the graphical representation of the transducer-based device, the graphical representation of the envelope representing an interior volume of the bodily cavity, or the graphical representation of the pre-existing image or model of the cavity, blending of colors utilized to represent each of the graphical representations is implemented in a translucent or semi-transparent manner to provide the operator with an efficient understanding of the relative positioning and locational depth of the objects represented by the graphical representations. At least FIG. 13, discussed in more detail below, illustrates some examples of such blending of colors utilized to represent relative positioning and locational depth of the pre-existing image or model of the cavity, the envelope representing the interior volume of the cavity, and the graphical representation of the catheter. In some embodiments in which a port or opening in the bodily cavity is represented in the envelope as completely transparent (i.e., with no color), and in which at least a portion of the graphical representation of the transducer-based device is viewable through the port or opening, such portion of the graphical representation may be displayed without color blending (i.e., in the true, unmodified colors of the graphical representation of the transducer-based device) so as to provide the operator with a realistic view that appears as if the operator is peering through the port or opening and directly seeing the portion of the transducer-based device. At least FIGS. 8-11, discussed in more detail below, illustrate some examples of an unobstructed view of the graphical representation of the catheter and its transducers through a port (e.g., port representation 802 or port representation 804) illustrated in the graphical representation of the envelope.

Figure 11:
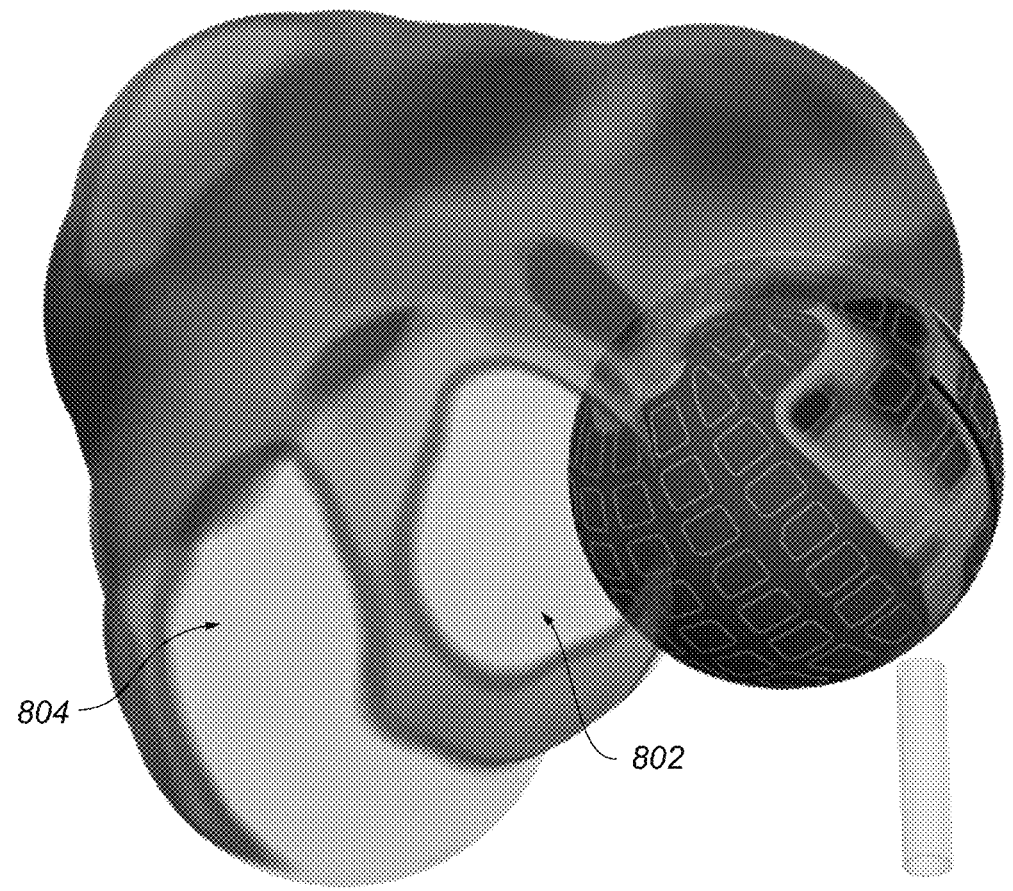
Figure 12A:
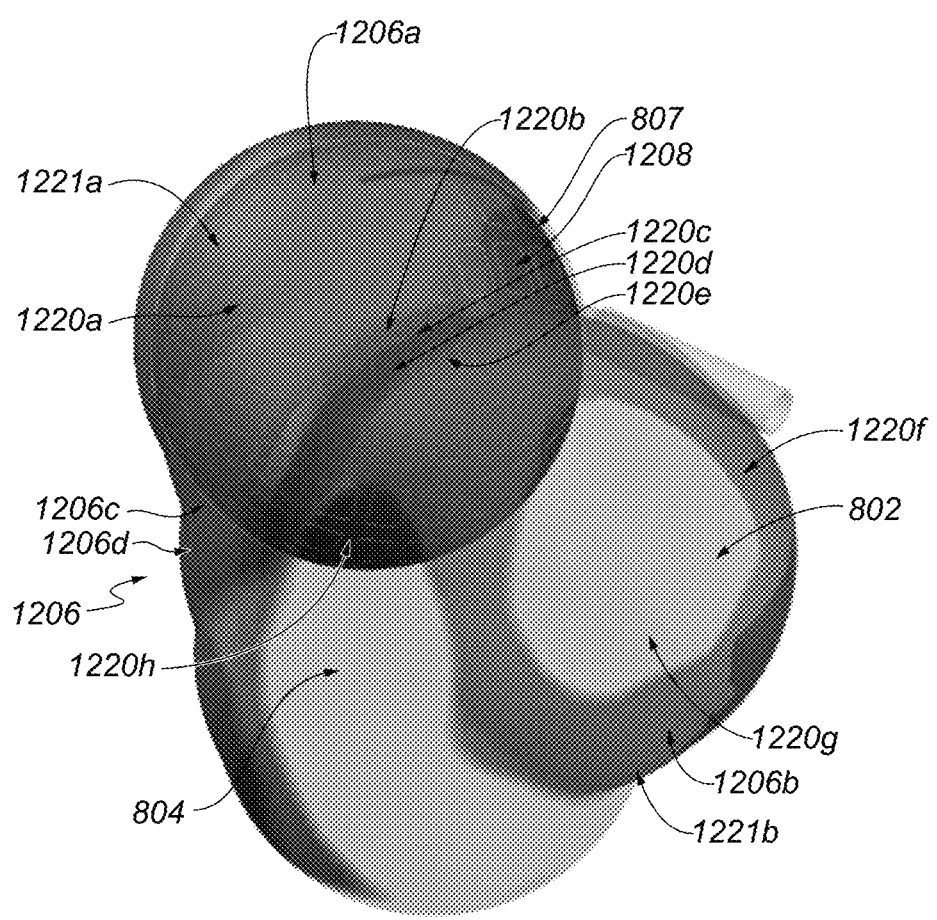
FIG. 12A illustrates a state of the graphical representation corresponding to FIG. 10, but with the graphical representations of the visually represented portion of the envelope and the visually represented portion of the transducer-based device including transducer graphical elements including visual characteristics indicating degrees of a detected electrical property, instead of degrees of detected tissue contact, according to various example embodiments.
Figure 12B:
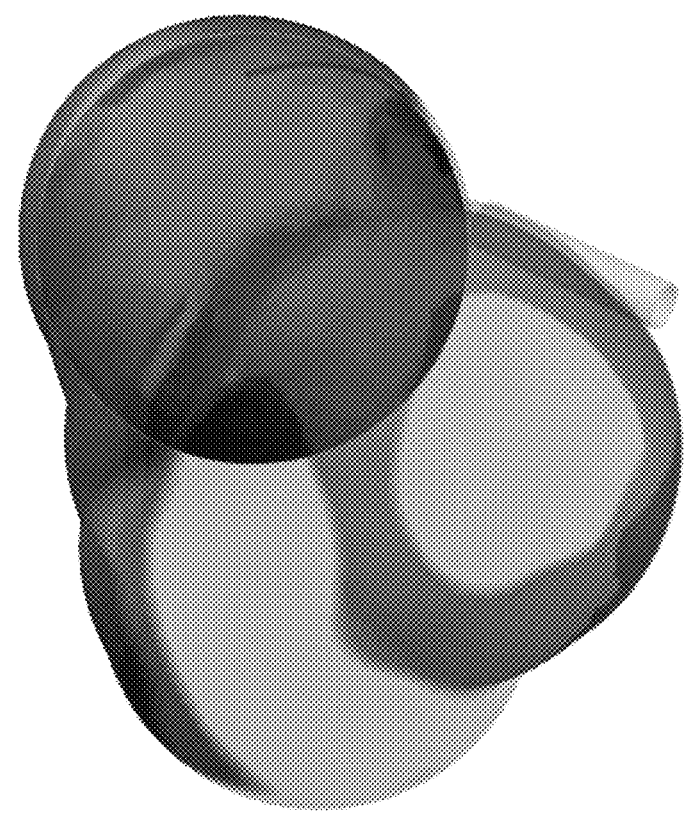
FIG. 12B illustrates the graphical representation of FIG. 12A, but without transducer graphical elements, according to various example embodiments.

In some embodiments, the graphical representation of the at least the portion of the envelope, the graphical representation of the transducer-based device, or both, have visual characteristics that indicate a tissue-electrical property detected by the transducers. At least FIGS. 12A and 12B, discussed in more detail below, illustrates some examples of tissue-electrical property information illustrated with various colorings on the graphical representations of both the envelope and the transducer-based device. As with the tissue-contact signals, the tissue-electrical property indicated via the graphical representation of the transducer-based device may represent presently detected degrees of the tissue-electrical property, and the tissue-electrical property indicated via the graphical representation of the at least the portion of the envelope may represent historically detected degrees of the tissue-electrical property when the transducers were at the respective locations in the bodily cavity as shown, for example, by FIGS. 12A and 12B, according to some embodiments. (FIG. 12A illustrates a visual representation of at least a portion of a transducer-based device (e.g., at least a portion of a catheter) as including transducer graphical elements, and FIG. 12B illustrates the visual representation of the transducer-based device of FIG. 12A, but without the transducer graphical elements, as discussed in more detail below.) Further, in embodiments where presently detected degrees of the tissue-electrical property (or other electrical or other property) are illustrated by a surface of the graphical representation of the transducer-based device, the surface of the graphical representation of the transducer-based device may visually present to the user, over time, a propagation or variation over time of detected degrees of the tissue-electrical property (or other electrical or other property) across such surface, akin to the sequence of different coloring patterns on the transducer-based device shown at least in FIGS. 8-11.

In light of the above-discussed and other features and advantages of various embodiments of the present invention, improved catheter navigation systems and methods are provided. In this regard, it should be noted that the invention is not limited to the above-discussed or any other examples provided herein, which are referred to for purposes of illustration only.

Returning to FIG. 14, block 1406 is associated with computer-executable instructions configured to cause the data processing device system (e.g., 110, 310) to progressively visually represent in a progressively enlarging manner via a display device system (e.g., display device system 332) communicatively connected to the programmed data processing device system, and based on and throughout reception of at least the plurality of location signal sets (e.g., according to block 1402) and, in some embodiments, based on and throughout reception of at least the plurality of contact signal sets, at least a portion of an envelope, the envelope representing an interior volume of the bodily cavity. At least the sequence of FIGS. 8-11 provides examples of a graphical user interface visually presented by the display device system 332 according to block 1406 to progressively visually represent in a progressively enlarging manner at least a portion of the envelope, according to some embodiments of the present invention.

Figure 8:
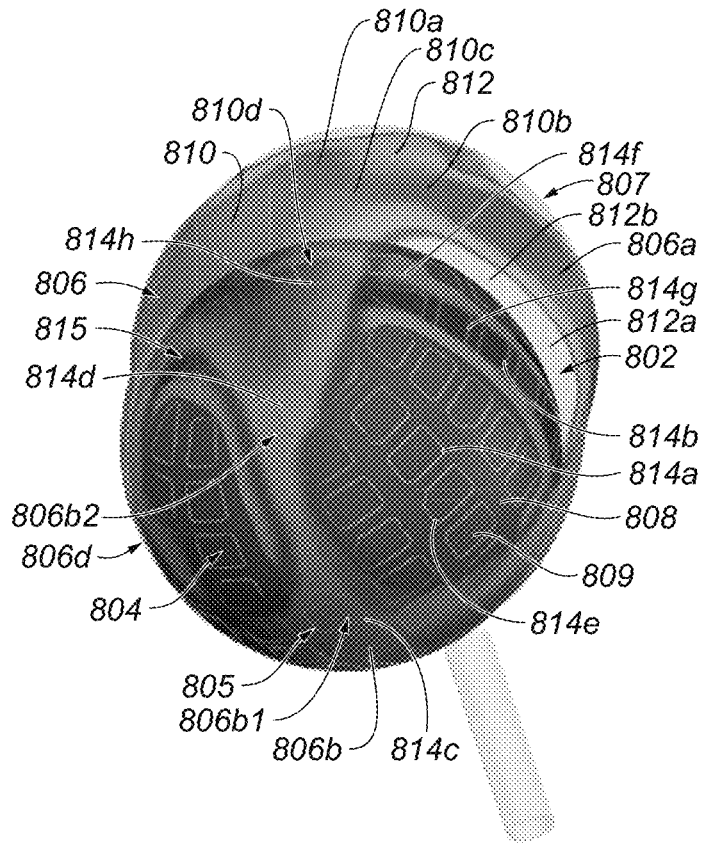
FIG. 8 illustrates, according to various example embodiments, a graphical representation, presented via a display device system, of a portion of an envelope representing an interior volume of a bodily cavity, in this instance, a left atrium of a heart, and of a portion of a transducer-based device, like the ones illustrated at least in FIGS. 4 and 6, the graphical representation of the portion of the transducer-based device including graphical representations of transducer graphical elements representing transducers of the transducer-based device, and the graphical representations of the portion of the envelope and the portion of the transducer-based device including the transducer graphical elements including visual characteristics indicating degrees of detected tissue contact.

With respect to FIG. 8, and as discussed above, the location signal sets received according to block 1402 provide a sequence of three-dimensional (R, S, and T axis)

locations of the transducer-based device (e.g., transducer-based device 200, 300, or 400) as it moves through the bodily cavity (or a simulated cavity in a quality-control, training, or testing environment), according to some embodiments. The contact signal sets received according to block 1404 provide a sequence of degree-of-contact information detected by at least a first set of transducers of the transducers of the catheter or transducer-based device, according to some embodiments. With the location signal sets and the contact signal sets, the data processing device system 110, 310 is configured to determine the degrees-of-contact detected by the at least the first set of transducers at each three-dimensional location of the transducer-based device in the sequence of movements of the transducer-based device. With the degrees-of-contact at each location in the sequence, the data processing device system 110, 310 is configured to formulate and plot at least a portion of the envelope representing the interior volume of the cavity, with the degrees-of-contact visually represented on a surface of the envelope.

For example, FIG. 8 represents a visual representation 806 of a portion of the envelope, according to some embodiments. In the state of FIG. 8, the visual representation 806 of the portion of the envelope includes a representation 806a of a first progressive enlargement of the envelope and a representation 806b of a second progressive enlargement of the envelope. The representation 806a of the first progressive enlargement of the envelope corresponds to an initial location of at least a portion of the catheter (e.g., transducer-based device 200, 300, or 400) in the sequence of locations at which at least the portion of the catheter, graphically represented by catheter representation 808, has been sequentially located in the bodily cavity. The representation 806b of the second progressive enlargement of the envelope corresponds to a second location of the at least the portion of the catheter in the sequence of locations.

In a state in which the at least the portion of the catheter (e.g., transducer-based device 200, 300, or 400) was at the initial location in the sequence of locations, the data processing device system 110, 310 receives, according to block 1402 and block 1404 in FIG. 14, three-dimensional location information of the catheter and degree-of-contact information detected by transducers of the catheter associated with the initial location, e.g., as per the above discussions with respect to FIGS. 2 and 3. With such information, the data processing device system 110, 310 is configured, according to program instructions associated with block 1406, to at least plot a three-dimensional shell (e.g., which may represent at least a portion of the envelope) that has the shape of the at least the portion of the catheter with degree-of-contact information plotted (e.g., using coloration) on the surface of the shell, resulting in visual representation of at least a portion of the envelope. In this regard, if a transducer-based device like that shown in FIGS. 4 and 6 is used, the initial generation of the envelope or shell may likely have a spherical-like shape to match the shape of the transducer-based device itself shown in FIGS. 4 and 6.

As the at least the portion of the catheter moves to the second location in the sequence of locations, the data processing device system 110, 310 receives, according to block 1402 and block 1404 in FIG. 14, three-dimensional location information of the catheter and degree-of-contact information detected by transducers of the catheter associated with the second location. With such information, the data processing device system 110, 310 is configured, according to program instructions associated with block 1406, to plot a three-dimensional enlargement of the shell generated in association with the degree-of-contact information associated with the initial location, the plotted enlargement forming an expansion region of the shell, resulting in a progressively enlarged visual representation of the at least a portion of the envelope. FIG. 8 shows an example of such an enlargement from a first location of a portion of a catheter to a second location, according to some embodiments. In this regard, representation 806*b* may represent an initial expansion of the initially generated envelope or shell. The remnant of the initially generated envelope or shell is illustrated by representation 806*a* in FIG. 8, according to some embodiments. The resulting shape of the expanded envelope or shell, e.g., as shown in the example of FIG. 8, may be determined or generated by the controller 324 including in the expanded envelope or shell only the outermost three-dimensional transducer locations from both the first location in the sequence of locations and the second location in the sequence of locations, according to some embodiments. Examples of how to generate a three-dimensional representation of a chamber based on recorded locations can be found in U.S. Patent Application Publication No. 2017/0330487 (Harley et al.), published Nov. 16, 2017, which is hereby incorporated herein by reference.

The resulting shape of the expanded envelope or shell may be completed or smoothed by the controller 324 generating additional positions by interpolating between actual detected transducer positions, according to some embodiments. Degree of tissue contact information detected by the transducers may be represented on the surface of the envelope or shell, e.g., by using coloration as shown in FIG. 8 or other visual characteristics. In some embodiments, interpolation may be utilized to improve stitching a newly expanded region of the envelope to a previously existing portion of the envelope. For instance, a first location signal set from the transducers (e.g., transducers 220, 306, 406) may have been analyzed by the data processing device system 110, 310 to generate the initial portion (e.g., representation 806*a*) of the envelope in FIG. 8, and a second location signal set from the transducers (e.g., transducers 220, 306, 406) may have been analyzed by the data processing device system 110, 310 to generate the newly expanded portion (e.g., representation 806*b*) of the envelope in FIG. 8. A seam-region 815 between the portions (e.g., representations 806*a*, 806*b*) may, in part, be generated by interpolating position values or vectors between the first and second location signal sets. In this regard, in some embodiments, the data processing device system 110, 310 is configured at least by a program at least to generate an interpolated portion (e.g., at least part of seam-region 815) of the at least the portion of the envelope at least by determining interpolating position values or vectors based at least on an analysis of position values or vectors indicated by (i) a first location signal set associated with a first portion (e.g., representation 806*a*) of the at least the portion of the envelope, and (ii) a second location signal set associated with a second portion (e.g., representation 806*b*) of the at least the portion of the envelope. In some embodiments, the data processing device system 110, 310 is configured at least by a program at least to cause the display device system (e.g., display device system 332) to display, as at least part of the progressive enlargement of the envelope, the interpolated portion (e.g., at least part of seam-region 815) of the at least the portion of the envelope between the first portion (e.g., representation 806*a*) of the at least the portion of the envelope and the second portion (e.g., representation 806*b*) of the at least the portion of the envelope.

In some embodiments, the visual representation 806 of at least the portion of the envelope visually represented via the display device system 332 visually indicates, based at least on the plurality of contact signal sets received according to block 1404, greater-contact regions of the at least the portion of the envelope associated with relatively greater transducer-to-tissue contact in accordance with a first visual characteristic set, and visually indicates lesser-contact regions of the at least the portion of the envelope associated with relatively lesser transducer-to-tissue contact in accordance with a second visual characteristic set, the second visual characteristic set different than the first visual characteristic set. In some embodiments, as illustrated in FIG. 8, greater-contact regions, such as greater-contact region 810, of the at least the portion of the envelope associated with relatively greater transducer-to-tissue contact are visually indicated with relatively darker colors, and lesser-contact regions, such as lesser-contact region 812, of the at least the portion of the envelope associated with relatively lesser transducer-to-tissue contact are visually indicated with relatively lighter colors. In some embodiments, all tissue-contact regions, such as greater-contact regions, which are associated with a same degree of contact, exhibit a same visual characteristic of the first visual characteristic set. For example, greater contact regions 810*a* and 810*b*, which are associated with a same degree of transducer-to-tissue contact, are represented by a same color. In some embodiments, all regions of the lesser-contact regions, which are associated with a same degree of transducer-to-tissue contact based at least on some of the plurality of contact signal sets, are visually represented with a same visual characteristic of the second visual characteristic set. For example, lesser contact regions 812*a* and 812*b*, which are both associated with no transducer-to-tissue contact in this example, are represented by no color or as transparent. It is noted that no transducer-to-tissue contact may be associated not only with no transducer-to-tissue contact, but also with a minimal degree of transducer-to-tissue contact at or within a threshold degree. In some embodiments, the visual characteristics utilized to display various degrees of detected transducer-to-tissue contact may be user-configurable.

In some embodiments, the first visual characteristic set is configured to visually indicate the greater-contact regions of the at least the portion of the envelope at least in part according to a first color set, and the second visual characteristic set is configured to visually indicate the lesser-contact regions of the at least the portion of the envelope at least in part according to a second color set, the first color set mutually exclusive with the second color set. Such a feature may assist the operator in quickly determining degrees of tissue contact without ambiguity. For example, in FIG. 8, the darker colors associated with the greater-contact regions 810, 810*a*, 810*b* are mutually exclusive with the lighter colors associated with the lesser-contact regions 812, 812*a*, 812*b*, according to some embodiments. In some embodiments, each color in the first color set, the second color set, or both the first color set and the second color set has a different hue, different lightness, or different saturation (e.g., according to the HSL (hue, saturation, lightness) representation of the RGB (red, green, blue) model, known in the art) than each color in its own color set, in the other color set, or in each of its own color set and the other color set.

In some embodiments, the first visual characteristic set associated with the greater-contact regions is configured to visually distinguish at least two regions of the greater-contact regions of the at least the portion of the envelope, the at least two regions of the greater-contact regions of the at least the portion of the envelope indicating different degrees of transducer-to-tissue contact. For example, in FIG. 8, greater-contact region 810*a* and greater-contact region 810*c* represent different degrees of relatively greater transducer-to-tissue contact, with greater-contact region 810*c* representing lesser transducer-to-tissue contact than greater-contact region 810*a*. Consequently, in FIG. 8, greater-contact region 810*c* is represented with a slightly lighter color than greater-contact region 810*a*, in order to represent the relatively lesser transducer-to-tissue contact associated with the greater-contact region 810*c* as compared to the greater-contact region 810*a*, according to various embodiments. In some embodiments, the color palette utilized for the first visual characteristic set, the second visual characteristic set, or both, may consist of unique (non-repeated) colors. In the case of lesser-contact regions, in FIG. 8 for example, lesser-contact region 812 and lesser-contact region 812*a* represent different degrees of relatively greater transducer-to-tissue contact, with lesser-contact region 812*a* representing lesser transducer-to-tissue contact than lesser-contact region 812. Consequently, in FIG. 8, lesser-contact region 812*a* (associated with no-tissue contact in this example) is represented with no color or as fully transparent, and the lesser-contact region 812 (associated with some tissue contact) is represented with color or as non-fully transparent, in order to represent the relatively lesser transducer-to-tissue contact associated with the lesser-contact region 812*a* as compared to the lesser-contact region 812, according to various embodiments.

In some embodiments, the data processing device system 110, 310 is configured (e.g., according to program instructions associated with block 1406 in FIG. 14) at least to cause the visually represented at least the portion of the envelope to visually indicate, via the display device system 332, one or more tissue-contact regions (e.g., at least tissue-contact regions 810, 810*a*, 810*b*, 810*c*, 812) according to a first color set, and to visually indicate, via the display device system 332, one or more no-tissue-contact regions (e.g., at least no-tissue contact regions 804, 808, 812*a*, 812*b*) according to a second color set mutually exclusive with the first color set. Each region of the one or more no-tissue-contact regions may be surrounded, enclosed, or encircled by at least some of the one or more tissue-contact regions. At least one region of the one or more no-tissue-contact regions may correspond to at least part of a port (e.g., port representation 802 and port representation 804 in FIG. 8) that interrupts the tissue surface within the bodily cavity, according to some embodiments (e.g., in instances where the no-tissue-contact region is located on the surface of the visual representation of the at least the portion of the envelope and is surrounded, enclosed, or encircled by other surface regions associated with tissue contact). Similarly, in some embodiments, the data processing device system 110, 310 is configured (e.g., according to program instructions associated with block 1406 in FIG. 14) at least to cause, during the progressively visually representing in the progressively enlarging manner of at least the portion of the envelope (as shown, e.g., by the sequence of FIGS. 8-11), (a) a first particular envelope enlargement (e.g., associated with representation 806*a* of the first progressive enlargement of the envelope in FIG. 8) to visually represent, via the display device system 332, a particular tissue-contact region (e.g., any of regions 810, 810*a*, 810*b*, 810*c*, or 812) according to a first color set, and (b) a second particular envelope enlargement (e.g., associated with representation 806*b* of the second progressive enlargement of the envelope in FIG. 8) to visually represent, via the display device system 332, a particular no-tissue-contact region (e.g., region 804) according to a second color set mutually exclusive with the first color set. In the example of FIG. 8, the tissue-contact regions 810, 810*a*, 810*b*, 810*c*, 812 are visually indicated via translucent colors that may comprise such a first color set, and the no-tissue contact regions 802, 804, 807, 812*a*, 812*b* are visually indicated with no color or as fully transparent, which may comprise such a second color set, according to some embodiments. In some embodiments, the second particular envelope enlargement may be the first particular envelope enlargement. In some embodiments, the data processing device system 110, 310 is configured (e.g., according to program instructions associated with block 1406 in FIG. 14) at least to cause the visually represented at least the portion of the envelope to visually represent, via the display device system 332, each of one or more tissue-contact regions (e.g., regions 810, 810*a*, 810*b*, 810*c*, or 812 in FIG. 8) as less transparent than each of one or more no-tissue-contact regions (e.g., regions 804, 808, 812*a*, 812*b*).

Although the example of FIG. 8 represents some embodiments where no-transducer-to-tissue contact is visually indicated with no color or as fully transparent, other embodiments represent no-transducer-to-tissue contact with a color, either translucent or opaque. For example, as discussed in more detail below, no-transducer-to-tissue contact regions are represented on catheter representation 808 as a dark color 809 in the example of FIG. 8. In this regard, in some embodiments, each color in the first color set, the second color set, or both the first color set and the second color set has a different hue, different lightness, or different saturation than each color in its own color set, in the other color set, or in each of its own color set and the other color set.

Although the above-discussed examples refer to different colors as visual characteristic sets, other embodiments utilize different visual characteristic sets, such as the use of different icons or illustrated surface features or textures to illustrate different degrees of transducer-to-tissue contact. However, in some embodiments, use of coloration may be preferable, since it allows, among other things, color blending to illustrate depth of relative objects. For example, as shown in FIG. 8, the visual representation 806 of the portion of the envelope graphically overlaps (e.g., because it is illustrated as containing) the catheter representation 808, such that colors representing degrees-of-tissue contact represented on the graphical surface of the catheter representation 808 are blended with colors representing degrees-of-tissue contact represented on the graphical surface of the visual representation 806 of the portion of the envelope, which aids in illustrating to an operator that the at least the portion of the catheter is within the interior volume of the bodily cavity, while allowing the operator to still have an understanding of the present or current degrees-of-tissue contact detected by transducers (e.g., transducers 220, 306, 406) of the catheter (e.g., transducer based device 200, 300, or 400), as represented by the graphical surface of the catheter representation 808, and the past degrees-of-tissue contact detected by transducers of the catheter, as represented by the graphical surface of the visual representation 806 of the portion of the envelope.

In some embodiments, the first visual characteristic set associated with the greater-contact regions and the second visual characteristic set associated with the lesser-contact regions are configured to cause the greater-contact regions of the at least the portion of the envelope to visually appear less transparent than at least one particular lesser-contact region of the lesser-contact regions of the at least the portion of the envelope. In some embodiments, the at least one particular lesser-contact region of the lesser-contact regions of the at least the portion of the envelope is associated with no transducer-to-tissue contact. In some embodiments, the second visual characteristic set is configured to cause the at least one particular lesser-contact region of the at least the portion of the envelope to visually appear as fully transparent. For example, in some embodiments such as those illustrated in FIG. 8, lesser-contact regions, such as lesser-contact regions 812*a* and 812*b*, that are associated with no detected transducer-to-tissue contact are illustrated by the visual representation 806 of the portion of the envelope with no color or as fully transparent. The greater-contact regions, which do not appear as transparent in the example embodiments of FIG. 8, may visually appear as less transparent than at least a transparent lesser-contact region, according to some embodiments. In some embodiments, a level of transparency may be proportional to a degree of detected transducer-to-tissue contact.

In some embodiments, the data processing device system 110, 310 is configured (e.g., according to program instructions associated with block 1406 in FIG. 14) at least to cause the display device system 332 to visually locate a particular greater-contact region (e.g., greater-contact region 810) of the greater-contact regions in a first region (e.g., representation 806*a* of the first portion) of at least a portion of the envelope, the first region of the at least the portion of the envelope corresponding to a first particular location in the sequence of locations at which at least the portion of a catheter (e.g., graphically represented by catheter representation 808) has been sequentially located in the bodily cavity, e.g., as discussed above with respect to the formation of representation 806*a* and representation 806*b*, which represents an enlargement of the envelope. In some embodiments, the data processing device system 110, 310 is configured (e.g., according to program instructions associated with block 1406 in FIG. 14) at least to cause the display device system to visually indicate the particular greater-contact region (e.g., greater-contact region 810) according to the first visual characteristic set associated with the greater-contact regions in the first region of the at least the portion of the envelope in a state representative of the at least the portion of the catheter being located at a second particular location in the sequence of locations in the bodily cavity, the second particular location subsequent to the first particular location in the sequence of locations. For example, in FIG. 8, the particular coloring (an example of the first visual characteristic) of the greater-contact region 810 remains the same when the portion of the catheter moves from the first particular location (associated with representation 806*a*) to the second particular location (associated with representation 806*b*), illustrating a 'stamping' effect that the catheter representation 808 leaves on the envelope or shell 806, according to some embodiments. In other words, the current location of the catheter representation 808 provides expanded or updated tissue contact representations to its current region (e.g., region 806*b*) of the envelope 806, but when the catheter representation 808 moves away from such region, the envelope 806 in that region retains the prior tissue contact representations, as if the catheter representation 808 'stamped' its contact information onto the envelope 806 when it was at that region.

In some embodiments, a particular lesser-contact region representative of no-tissue-contact, which is surrounded, enclosed, or encircled by contact regions (e.g., at least some of the greater-contact regions, the lesser-contact regions, or both), corresponds to at least part of a port interrupting the tissue surface within the bodily cavity, according to some embodiments. In FIG. 8, port representation 802 (which contains lesser-contact regions 812*a* and 812*b*) or port representation 804 represents such a port. In some embodiments, the data processing device system 110, 310 is configured at least by program instructions associated with block 1406 at least to cause, during the progressively visually representing in the progressively enlarging manner of the at least the portion of the envelope, a particular envelope enlargement (e.g., represented in FIG. 8, for example, by representation 806*b*) to visually represent, via the display device system 332, one or more particular no-tissue-contact regions (e.g., port representation 804 in FIG. 8) surrounded, enclosed, or encircled by one or more particular tissue-contact regions (e.g., represented by contact region 805 in FIG. 8).

In some embodiments, during the progressively visually representing in the progressively enlarging manner, e.g., according to program instructions associated with block 1406, the data processing device system may be configured by such program instructions at least to cause the display device system 332 to visually indicate each envelope enlargement leading to the visually represented at least the portion of the envelope to visually include (a) at least one tissue-contact region (e.g., represented in FIG. 8 by at least region 805 associated with the expansion region 806*b*), (b) at least one no-tissue-contact region (e.g., represented in FIG. 8 by at least port representation 802 associated with the expansion region 806*b*), or both (a) and (b), such that the visual representation 806 of at least the portion of the envelope visually distinguishes one or more tissue-contact regions from one or more no-tissue-contact regions (e.g., region 805 is represented with color, and region 802 is represented by an absence of color (transparent or partially transparent), according to some embodiments).

In this regard, it may be beneficial in some contexts to have the visual representation 806 of the at least the portion of the envelope concurrently represent, based at least on a contact signal set produced from a single location of the catheter, an interior surface of the bodily cavity (or other cavity in a quality-control, training, or testing environment), represented by a tissue-contact region, and a port of entry into the cavity, represented by a no-tissue-contact region. The identification of at least part of a port region with data acquired from a single catheter position can reduce procedure time. In contrast, in conventional systems, multiple manipulations or movements of a mapping catheter have been required to determine both a region of a tissue surface of a bodily cavity and a port of entry into the bodily cavity, thereby requiring greater time and complexity of operation. On the other hand, e.g., FIG. 8 illustrates that the visual representation 806*b* associated with a second location of the catheter in the sequence of locations of the catheter identifies or substantially identifies the location of a port associated with port region 804 in a single position of the catheter, as the port region 804 may be determined by the controller 324 to be surrounded, enclosed, or encircled by tissue-contact regions and, therefore, be a location of a port.

In some embodiments, in addition to visually representing the at least the portion of the envelope (e.g., visual representation 806 of a portion of the envelope in FIG. 8), the data processing device system 110, 310 is configured (e.g., according to program instructions associated with block 1406 in FIG. 14) at least to cause the display device system 332 to display a plurality of graphical elements (e.g., only graphical elements 814*a*, 814*b*, 814*c*, 814*d*, 814*e*, 814*f*, 814*g*, and 814*h* are called out in FIG. 8 for purposes of clarity), where each graphical element corresponds to a respective transducer of the plurality of transducers (e.g., transducers 220, 306, 406) of at least a portion of the catheter (e.g., transducer-based device 200, 300, or 400). (Note that edges of some of the transducer graphical elements (e.g., 814c, 814d, 814f, 814h) that appear to the viewer to be underneath the visual representation 806 of the portion of the envelope have been enhanced in FIG. 8 to improve clarity.) In some embodiments, the transducers of the plurality of transducers (e.g., transducers 220, 306, 406) of the at least the portion of the catheter (e.g., transducer-based device 200, 300, or 400) are arrangeable in a first spatial distribution (e.g., as shown in at least FIG. 6), and the data processing device system 110, 310 is configured (e.g., according to program instructions associated with block 1406 in FIG. 14) at least to cause the displayed graphical elements (e.g., including graphical elements 814a, 814b, 814c) to be visually arranged by the display device system 332 in a second distribution that is consistent with, corresponds to, or represents the first spatial distribution. For example, in FIG. 8, the transducer graphical elements (e.g., including graphical elements 814a, 814b, 814c) are graphically represented as having a spatial distribution that is consistent with, corresponds to, and represents the actual spatial distribution of the actual corresponding transducers (e.g., transducers 220, 306, 406) in real three-dimensional space. Similarly, the shapes of the transducer graphical elements (e.g., including graphical elements 814a, 814b, 814c) may be consistent with, correspond to, or represent the actual shapes of the corresponding transducers (e.g., transducers 220, 306, 406), according to some embodiments.

In some embodiments, the data processing device system 110, 310 is configured (e.g., according to program instructions associated with block 1406 in FIG. 14) at least to cause, during the progressively visually representing in the progressively enlarging manner, the display device system (e.g., display device system 332) to display a first particular envelope enlargement (e.g., representation 806b in FIG. 8) accompanied by a display of a plurality of graphical elements (e.g., at least some of the graphical elements 814 in FIG. 8). In some embodiments, each graphical element is displayed in accordance with a visual characteristic set indicating the degree of transducer-to-tissue contact detected by the respective transducer at least in a state representative of at least a portion of the catheter being in a particular location (e.g., the represented location of the catheter representation 808 in FIG. 8) in the bodily cavity associated with the first particular envelope enlargement (e.g., representation 806b in FIG. 8). In some embodiments, the data processing device system 110, 310 is configured (e.g., according to program instructions associated with block 1406 in FIG. 14) at least to cause the display device system (e.g., display device system 332) to display the plurality of graphical elements (e.g., at least some of the graphical elements 814 in FIG. 8) as superimposed with the first particular envelope enlargement (e.g., representation 806b in FIG. 8). In some embodiments, historical degrees of detected transducer-to-tissue contact is visually represented via a surface of the graphical representation of the portion of the envelope (e.g., visual representation 806 in the example of FIG. 8), and present or current degrees of detected transducer-to-tissue contact may be graphically represented via the transducer graphical elements (e.g., at least some of the graphical elements 814 in FIG. 8). In some embodiments, the data processing device system 110, 310 is configured (e.g., according to program instructions associated with block 1406 in FIG. 14) at least to cause the display of each graphical element, at least in the state representative of the at least the portion of the catheter being in the particular location (e.g., the represented location of the catheter representation 808 in FIG. 8) associated with the first particular envelope enlargement, to visually represent present or current degrees of transducer-to-tissue contact detected by the respective transducers (e.g., transducers 220, 306, 406) according to a corresponding most recent contact signal set associated with the particular location and provided by the respective transducers. In some embodiments, the data processing device system 110, 310 is configured (e.g., according to program instructions associated with block 1406 in FIG. 14) at least to cause the display device system (e.g., display device system 332) to display at least one tissue-contact region (e.g., at least contact region 810a) of the at least the portion of the envelope to visually represent previous degrees of transducer-to-tissue contact detected by at least some transducers (e.g., transducers 220, 306, 406) according to one or more corresponding not-most-recent contact signal sets associated with a previous location of the at least the portion of the catheter (e.g., associated with representation 806a) and provided by the at least some transducers.

Turning now to FIG. 15, a respective data generation and flow diagram is illustrated, which may implement various embodiments of method 1500 by way of associated computer-executable instructions, according to some example embodiments. In various example embodiments, a memory device system (e.g., memory device system 130 or 330) is communicatively connected to a data processing device system (e.g., data processing device 110, 310) and stores a program executable by the data processing device system to cause the data processing device system to execute various embodiments of method 1500 via interaction with at least one or more devices of a catheter-device-location tracking system, for example, one or more transducers of a transducer-based device (e.g., transducer-based devices 200, 300, or 400) operating within an electric or magnetic field generated by one or more external devices (e.g., the external electrodes 256a, 256b, 256c, 256d, 256e, 256f in the case of electric field(s); and, e.g., magnetic field generation sources 257w, 257x, 257y in the case of magnetic field(s)). In this regard, various embodiments of the method 1500 are executed by a programmed data processing device system (e.g., 110, 310) of a catheter navigation system. In various embodiments, the program may include instructions configured to perform, or cause to be performed, various ones of the instructions associated with execution of various embodiments of method 1500. In some embodiments, method 1500 may include a subset of the associated blocks or additional blocks than those shown in FIG. 15. In some embodiments, method 1500 may include a different sequence indicated between various ones of the associated blocks shown in FIG. 15. In some embodiments, block 1506 may be added to method 1400 in FIG. 14, e.g., as part of block 1406.

In some embodiments, block 1502 is associated with computer-executable instructions configured to cause the data processing device system (e.g., 110, 310) to receive, via the input-output device system (e.g., 120, 320), a plurality of location signal sets, which may originate from at least some transducers (e.g., transducers 220, 306, 406) of a catheter-device-location tracking system. As discussed above with respect to FIG. 2, each location signal set of the plurality of location signal sets may be indicative of a respective location in a sequence of locations at which at least a portion of the catheter has been sequentially located in a bodily cavity.

In some embodiments, block 1502 may correspond to block 1402 in FIG. 14. Further, a block corresponding to block 1404 may be present in method 1500 leading to block 1506, according to some embodiments.

In some embodiments, block 1506 is associated with computer-executable instructions configured to cause the data processing device system (e.g., 110, 310) to generate and cause, at least in a state representative of the at least the portion of the catheter (e.g., represented by catheter representation 808 in FIG. 8) being in a particular location in the sequence of locations, the display device system 332 to display a graphical representation (e.g., as shown in at least FIG. 8). In some embodiments, the graphical representation includes a visual representation, in a graphically-overlapping manner or at least in a concurrent manner in some embodiments, of at least (a) at least a portion of an envelope (e.g., represented by visual representation 806 in the example of FIG. 8) representing an interior volume of the bodily cavity, and (b) a plurality of graphical elements (e.g., including graphical element 814c called out in FIG. 8). For example, in FIG. 8, the visual representation 806 of at least a portion of the envelope is displayed in a graphically-overlapping manner with at least the transducer graphical element 814c. In some embodiments, the at least the portion of the envelope is visually represented (e.g., by visual representation 806 in the example of FIG. 8) based at least on some location signals received according to the program instructions associated with block 1502. The at least some location signals may represent at least two locations in the sequence of locations at which at least a portion of the catheter has been sequentially located in a bodily cavity. For example, in FIG. 8, the representation 806a of a first progressive enlargement of the envelope and the representation 806b of the second progressive enlargement of the envelope may be associated with at least two locations in the sequence of locations at which at least the portion of the catheter has been sequentially located in a bodily cavity. In some embodiments, each graphical element of the plurality of graphical elements (e.g., including graphical element 814c called out in FIG. 8) corresponds to a respective transducer of the plurality of transducers, and the graphical elements of the plurality of graphical elements may be arranged in a distribution that is consistent with, corresponds to, or represents the spatial distribution of the actual transducers that they represent.

In some embodiments, each transducer graphical element may represent the present or current degree-of-transducer-to-tissue contact detected by its corresponding transducer. In some embodiments, each of at least first and second transducer graphical elements represent the degree-of-transducer-to-tissue contact detected by its corresponding transducer. For instance, in some embodiments, the graphical representation (e.g., shown in at least FIG. 8) includes a display of at least a first graphical element (e.g., at least graphical element 814c in the example of FIG. 8) in accordance with a first visual characteristic set indicating a first degree of transducer-to-tissue contact, the first graphical element located in a first region (e.g., at least a portion 806b1 of representation 806b) of the at least the portion of the envelope. The phrase "located in a first region" and similar phrases used herein are intended to mean that the graphical element is graphically represented as overlapped by or overlapping at least part of the first region of the graphically represented envelope, which may take into account the camera or viewing angle utilized by the data processing device system 110, 310 to generate the graphical representations of the graphical element and the at least the portion of the envelope. According to some embodiments, the first graphical element corresponds to a first transducer detecting the first degree of transducer-to-tissue contact at least in a state representative of the at least the portion of the catheter being in a particular location in the sequence of locations (e.g., the location associated with the second progressive enlargement of the envelope represented by representation 806b in the example of FIG. 8). Further, in some embodiments, the graphical representation (e.g., shown in at least FIG. 8) includes a display of at least a second graphical element (e.g., at least graphical element 814d in the example of FIG. 8) in accordance with a second visual characteristic set indicating a second degree of transducer-to-tissue contact, the second graphical element located in a second region (e.g., at least a portion 806b2 of representation 806b) of the at least the portion of the envelope. The second graphical element corresponds to a second transducer detecting the second degree of transducer-to-tissue contact at least in the state representative of the at least the portion of the catheter being in the particular location in the sequence of locations (e.g., the location associated with the second progressive enlargement of the envelope represented by representation 806b in the example of FIG. 8). In some embodiments, at least one difference between the first visual characteristic set and the second visual characteristic set indicates at least one difference between the first degree of transducer-to-tissue contact and the second degree of transducer-to-tissue contact. In the example of FIG. 8, graphical element 814c is represented by darker coloring than graphical element 814d in order to indicate to an operator that the transducer associated with graphical element 814c is detecting greater transducer-to-tissue contact than the transducer associated with graphical element 814d.

In some embodiments, the first visual characteristic set associated with the first degree of transducer-to-tissue contact is configured to visually indicate relatively greater degree of transducer-to-tissue contact and the second visual characteristic set associated with the second degree of transducer-to-tissue contact is configured to visually indicate a relatively lesser degree of transducer-to-tissue contact. As stated above, for example, in FIG. 8, graphical element 814c is represented by darker coloring than graphical element 814d in order to indicate to an operator that the transducer associated with graphical element 814c is detecting greater transducer-to-tissue contact than the transducer associated with graphical element 814d according to some embodiments. In some embodiments, the first visual characteristic set (e.g., associated with graphical element 814c and, e.g., other graphical elements associated with transducers exhibiting relatively greater transducer-to-tissue contact) is configured to visually indicate the relatively greater degree of transducer-to-tissue contact at least in part according to a first color set, and the second visual characteristic set (e.g., associated with graphical element 814d and, e.g., other graphical elements associated with transducers exhibiting relatively lesser transducer-to-tissue contact) is configured to visually indicate the relatively lesser degree of transducer-to-tissue contact at least in part according to a second color set mutually exclusive with the first color set. For example, as discussed above, similar to at least greater contact regions 810 and at lesser-contact regions 812 of the portion of the envelope represented by visual representation 806, relatively greater degrees of detected tissue contact and relatively lesser degrees of detected tissue contact may be represented by mutually exclusive color sets. For example, in some embodiments, no tissue contact (which may be an example of the above-discussed second degree of transducer-to-tissue contact) is visually represented by coloring the corresponding transducer graphical elements (e.g., graphical element 814e) a blue color, which appears to be a dark gray color in FIG. 8, light tissue contact is visually represented by coloring the corresponding transducer graphical elements (e.g., graphical element 814d) a light green color, which appears to be a light gray color in FIG. 8, and greater tissue contact is visually represented by coloring the corresponding transducer graphical elements (e.g., graphical element 814b) a dark green color, which appears to be a dark gray color in FIG. 8. The transducer graphical elements associated with no-detected-transducer-to-tissue contact (e.g., graphical element 814e), which are represented according to the second visual characteristic set, may indicate detection of a port in the bodily cavity (e.g., represented by port representation 802 in the example of FIG. 8). (Note that no-detected-transducer-to-tissue-contact may be associated with a range of minimal-to-no-detected-transducer-to-tissue-contact.) In the preceding coloring example, the dark green color set associated with relatively greater transducer-to-tissue contact is mutually exclusive with the color set comprising the blue and light green color sets associated with relatively lesser transducer-to-tissue contact, in some embodiments. However, different color variations or visual characteristic variations may be utilized in different embodiments. For instance, in some embodiments, each color in the first color set for transducer graphical elements associated with transducers detecting relatively greater transducer-to-tissue contact, the second color set for transducer graphical elements associated with transducers detecting relatively lesser transducer-to-tissue contact, or both the first color set and the second color set have a different hue, different lightness, or different saturation than each color in its own color set, in the other color set, or in each of its own color set and the other color set. In this regard, graphical elements associated with transducers detecting different degrees of transducer-to-tissue contact may be visually indicated with different visual characteristics according to a visual characteristic set to indicate such different degrees of detected transducer-to-tissue contact. For example, each level of detected degree of transducer-to-tissue contact may be associated with a unique color or graphical symbol, according to some embodiments.

In some embodiments, a same visual characteristic of the transducer graphical elements may be utilized to visually indicate a same detected degree of transducer-to-tissue contact. For instance, in some embodiments, the data processing device system 110, 310 is configured, according to program instructions associated with block 1506, at least to cause all graphical elements of the plurality of graphical elements corresponding to respective ones of the plurality of transducers associated with a same degree of detected transducer-to-tissue contact (e.g., at least graphical elements 814b, 814g) to exhibit a same visual characteristic of a particular visual characteristic set. In the example of FIG. 8, the graphical elements 814b and 814g are both represented by a same dark green color (appearing in FIG. 8 as a dark gray color) to indicate that the transducers (e.g., respective ones of transducers 220, 306, 406) that correspond to such graphical elements have detected a same degree of transducer-to-tissue contact according to some embodiments. According to some embodiments, the data processing device system 110, 310 is configured, according to program instructions associated with block 1506, at least to cause, in the displayed graphical representation (e.g., at least as shown by the example of FIG. 8), all graphical elements (e.g., at least transducer graphical elements 814b and 814g shown in the example of FIG. 8) that are associated with the first (e.g., relatively greater) degree of detected transducer-to-tissue contact to be displayed in accordance with the first visual characteristic set (e.g., including the above-discussed dark green color set), and all graphical elements (e.g., at least transducer graphical elements 814a, 814e) that are associated with the second (e.g., relatively lesser) degree of detected transducer-to-tissue contact to be displayed in accordance with the second visual characteristic set (e.g., including the above-discussed blue color set).

In some embodiments, the visual representation of the portion of the envelope (e.g., at least visual representation 806 in the example of FIG. 8) is visually presented in a translucent manner, such that the catheter representation 808 can be seen within the visual representation of the portion of the envelope, as shown, e.g., in at least FIG. 8, which shows catheter representation 808 including transducer graphical elements 814, according to some embodiments. The data processing device system 110, 310 may be configured, according to program instructions associated with block 1506, to produce such a translucent representation by blending colors of the visual representation of the portion of the envelope (e.g., at least visual representation 806 in the example of FIG. 8) and the catheter representation 808 (or its graphical elements 814), according to some embodiments. In some embodiments, the graphical overlapping of the visual representation of the portion of the envelope (e.g., at least visual representation 806 in the example of FIG. 8) and the catheter representation 808 (or its graphical elements 814) includes a blending of (i) a first color of at least a part of a first graphical element with (ii) a second color of an overlapping region in the at least the portion of the envelope that overlaps the at least the part of the first graphical element. In the example of FIG. 8, transducer graphical element 814h may represent such a first graphical element, which intrinsically is associated with a dark green color that is the same as the dark green color (which appears in FIG. 8 as a dark gray color) displayed by transducer graphical element 814g, according to some embodiments. However, the overlapping region 810d of the visually represented at least the portion of the envelope intrinsically is associated with a light green color that is the same as the light green color (which appears in FIG. 8 as a light gray color) displayed by region 812. Accordingly, the blending of the intrinsic dark green color for transducer graphical element 814h and the intrinsic light green color for overlapping region 810d results in the display of a medium green color (which appears in FIG. 8 as a medium gray color) in the graphical space occupied by transducer graphical element 814h in the example of FIG. 8, according to some embodiments. In particular, in the example of FIG. 8, the graphical space occupied by transducer graphical element 814h appears lighter than transducer graphical element 814g, even though the transducers associated with transducer graphical elements 814h and 814g have detected the same relatively greater degree of transducer-to-tissue contact, such that it appears to the operator that the transducer graphical element is underneath region 810d of the visual representation 806 of the portion of the envelope, according to some embodiments. (Transducer graphical element 814g is overlapped by transparent port region of port representation 802 of the envelope 806 in the example of FIG. 8 and, hence, its intrinsic color is not affected by any coloring of the envelope 806. It is noted that the phrase, "intrinsic color" is intended to refer to a color associated with a graphical element (e.g., 814) or region of the envelope (e.g., 806) in a state unaffected by lighting effects (e.g., from a graphical light source) or blending with the intrinsic color of an overlapping or overlapped graphical element or region of the envelope. For example, in the example of FIG. 8, the viewable color of graphical element 814*g* essentially is its intrinsic color, since graphical element 814*g* is viewable through the transparent port region of port representation 802 of the envelope 806 and, therefore, is unaffected by any blending of colors with any overlapping or overlapped graphical element or region of the envelope, although minor lighting effects may be present.)

In some embodiments, the second color (e.g., associated with overlapping region 810*d*) indicates, on the overlapping region in the at least the portion of the envelope, a different degree of transducer-to-tissue contact than the first degree of transducer-to-tissue contact (e.g., which may be associated with the transducer that corresponds to transducer graphical element 814*h* in some embodiments). In the example of FIG. 8, the overlapping region 810*d* has an intrinsic light green color (an example of the second color) representing a relatively lesser degree of previously detected transducer-to-tissue contact, and the graphical element 814*h* has an intrinsic dark green color (an example of the first color) representing a relatively greater degree of presently detected transducer-to-tissue contact, in some embodiments.

In the preceding examples with respect to FIG. 8, the same intrinsic colors or other visual characteristics are utilized for the graphical elements 814 and the visual representation (e.g., visual representation 806) of the portion of the envelope to represent the same detected degrees-of-tissue contact, according to some embodiments. For example, dark green is utilized as an intrinsic color to represent a same degree of relatively greater detected transducer-to-tissue contact for both (a) the graphical elements 814, and (b) the visual representation (e.g., visual representation 806) of the portion of the envelope, according to some embodiments. While such an approach may be preferable in some contexts, other approaches may be preferable in other contexts, such that different intrinsic colors or other visual characteristics are utilized to represent a same degree of detected transducer-to-tissue contact among the graphical elements and the visual representation of the portion of the envelope. For instance, utilizing a first intrinsic color to represent a first detected degree of transducer-to-tissue contact for the transducer graphical elements and a second, different intrinsic color to represent the same first detected degree of transducer-to-tissue contact for the visual representation of the portion of the envelope may help the operator more readily compare the present detected tissue contact represented by the transducer graphical elements and the historical detected tissue contact represented by the visual representation of the portion of the envelope (at least in regions where the at least the portion of the catheter is no longer present), according to some embodiments. In this regard, the detected degree of transducer-to-tissue contact could be no detected tissue contact. In this case, for example, FIG. 8 shows that a no detected tissue contact in the port region 802 of the envelope 806 is represented as transparent, but a blue (shown as gray) color is used to represent no detected tissue contact at, e.g., transducer graphical element 814*a*. Further, although degrees of tissue contact (or other information, such as tissue electrical information) are often discussed herein in the context of being visually represented by transducer graphical elements, such as transducer graphical elements 814, such information may be displayed at least by other portions of catheter representation 808. For example, the graphical space between transducer graphical elements (e.g., transducer graphical elements 814) may also represent degrees of tissue contact or other information, such as tissue electrical information, and the data for such information may be generated by the controller 324 or its data processing device system 310 by interpolating data detected by transducers associated with the adjacent transducer graphical elements.

In some embodiments, it may be beneficial and helpful to an operator to have port regions of the bodily cavity (or other cavity in a quality-control, training, or testing environment) visually represented as transparent or as an opening in the at least a portion of the envelope, as is the case in the example of FIG. 8, so that the operator may clearly view the catheter representation 808 when a portion of the catheter (e.g., transducer-based device 200, 300, or 400) is located in or near such port region. For example, in some embodiments, block 1506 in FIG. 15 includes program instructions configured to cause the data processing device system 110, 310 to display a first set of graphical elements (e.g., at least graphical element 814*h* in the example of FIG. 8) and a region (e.g., at least region 810*d*) of the at least the portion of the envelope in a first graphically-overlapping manner (e.g., in the color-blending manner discussed above in some embodiments), and with a second set of graphical elements (e.g., at least graphical elements 814*b*, 814*e* in the example of FIG. 8) displayed in a second graphical manner (e.g., in a fully or more transparent manner) indicating a view of the second set of graphical elements through a port region (e.g., port representation 802 in the example of FIG. 8) in the at least the portion of the envelope corresponding to a port into the bodily cavity. In the example of FIG. 8, port representation 802 is displayed transparently, such that the view of transducer graphical elements 814*b* and 814*e* are displayed in a graphically unobstructed manner. On the other hand, in the example of FIG. 8, region 810*d* of the portion of the envelope does not correspond to a port into the bodily cavity and, therefore, such region 810*d* is displayed with a color in a translucent manner, partially obscuring (e.g., by color blending) view of the visually underlying graphical element 814*h*, according to some embodiments.

In some embodiments, the first graphically-overlapping manner includes a blending of (i) a first color (e.g., the above-discussed intrinsic dark green color of transducer graphical element 814*h*) of at least a part of a first graphical element with (ii) a second color (e.g., the above-discussed light green color of region 810*d* of the portion of the envelope) of an overlapping region in the region of the at least the portion of the envelope that overlaps the at least the part of the first graphical element. In some embodiments, the second graphical manner includes a transparent graphical representation of the port region (e.g., port representation 802 in the example of FIG. 8) in the at least the portion of the envelope, which allows the second set of graphical elements (e.g., at least graphical elements 814*b*, 814*e*) to be viewable in a graphically unobstructed manner. In some embodiments, the second graphical manner includes a graphical representation of the second set of graphical elements (e.g., at least graphical elements 814*b*, 814*e*) through the port region (e.g., port representation 802 in the example of FIG. 8) in the at least the portion of the envelope without a blending of any colors associated with the port region in the at least the portion of the envelope.

While visually representing a port as fully transparent may be beneficial in some contexts, it is not required and other approaches may be beneficial in some contexts, such as varying translucency levels between port and non-port regions or assigning a specific color set for port regions (such as, e.g., the blue utilized to represent no-tissue contact on the surface of the catheter representation 808, where a similar approach may be used for the visual representation 806 of the portion of the envelope). In some embodiments, the second graphical manner includes a semi-transparent graphical representation of the port region in the at least the portion of the envelope, causing one or more colors of the second set of graphical elements to be blended with one or more colors of the port region in the at least the portion of the envelope. For instance, the port region 802 in the example of FIG. 8 may be represented with a color set but with greater transparency than colors utilized to represent non-port regions in the portion of the envelope, according to some embodiments. In some embodiments, the first graphically-overlapping manner (e.g., utilized to represent overlapping of a transducer graphical element, like transducer graphical element 814h and a region in a visual representation of the portion of the envelope, like region 810d in the example of FIG. 8) includes a graphical representation of the region of the at least the portion of the envelope in a first semi-transparent manner, causing one or more colors of the first set of graphical elements (e.g., including graphical element 814h) to be blended with one or more colors of the region (e.g., region 810d) in the at least the portion of the envelope. On the other hand, the second graphical manner (e.g., utilized to represent a graphical element, like graphical element 814b, in a port region, like port region 802 in the example of FIG. 8) includes a graphical representation of the port region in the at least the portion of the envelope in a second semi-transparent manner, causing one or more colors of the second set of graphical elements to be blended with one or more colors of the port region in the at least the portion of the envelope, where the first semi-transparent manner represents the region (e.g., region 810d) of the at least the portion of the envelope as less transparent than the second semi-transparent manner represents the port region (e.g., like port region 802) in the at least the portion of the envelope. For example, with respect to the example of FIG. 8, the port representation 802 may have a color, but may exhibit more transparency than a region, like region 810d, that is not representing a port in the bodily cavity.

Figure 9:
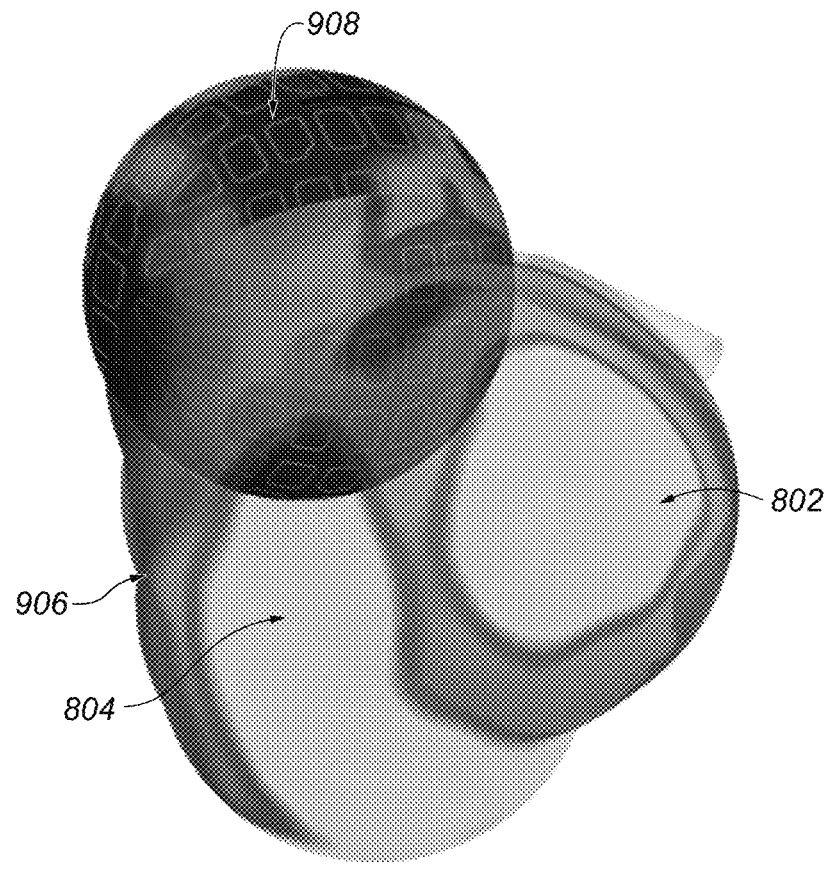
FIGS. 9-11 illustrate various progressive enlargements of the visually represented portion of the envelope representing an interior volume of the bodily cavity illustrated in FIG. 8, according to various example embodiments.

As discussed above, at least the sequence of FIGS. 8-11 provide examples of a graphical user interface visually presented by the display device system 332 according to block 1406 to progressively visually represent in a progressively enlarging manner at least a portion of the envelope representing an interior volume of the bodily cavity, according to some embodiments of the present invention. In the state of FIG. 8, the visual representation 806 of the portion of the envelope includes a representation 806a of a first progressive enlargement of the envelope and a representation 806b of a second progressive enlargement of the envelope. The representation 806a of the first progressive enlargement of the envelope corresponds to an initial location of at least a portion of the catheter (e.g., transducer-based device 200, 300, or 400) in the sequence of locations at which at least the portion of the catheter, graphically represented by catheter representation 808, has been sequentially located in the bodily cavity (or other cavity in a quality-control, training, or testing environment). The representation 806b of the second progressive enlargement of the envelope corresponds to a second location of the at least the portion of the catheter in the sequence of locations. FIG. 9 shows a state in which the at least the portion of the catheter is in a third location in the sequence of locations, but the data processing device system 110, 310 has not yet constructed a progressive enlargement of the envelope (illustrated by visual representation 906 in FIG. 9) to reflect the location signal sets and the contact signal sets received from the corresponding transducers (e.g., transducers 220, 306, 406) according to program instructions associated with, e.g., blocks 1402 and 1404 in FIG. 14. It should be noted that the phrase, "third location" is merely used to indicate that such location is subsequent to the above-discussed "second location" in the sequence of locations, although the at least the portion of the catheter may have been at additional locations in the bodily cavity between the "second location" and the "third location". The same may be said with respect to the "second location" and the "first location" in the sequence of locations.

Figure 10:
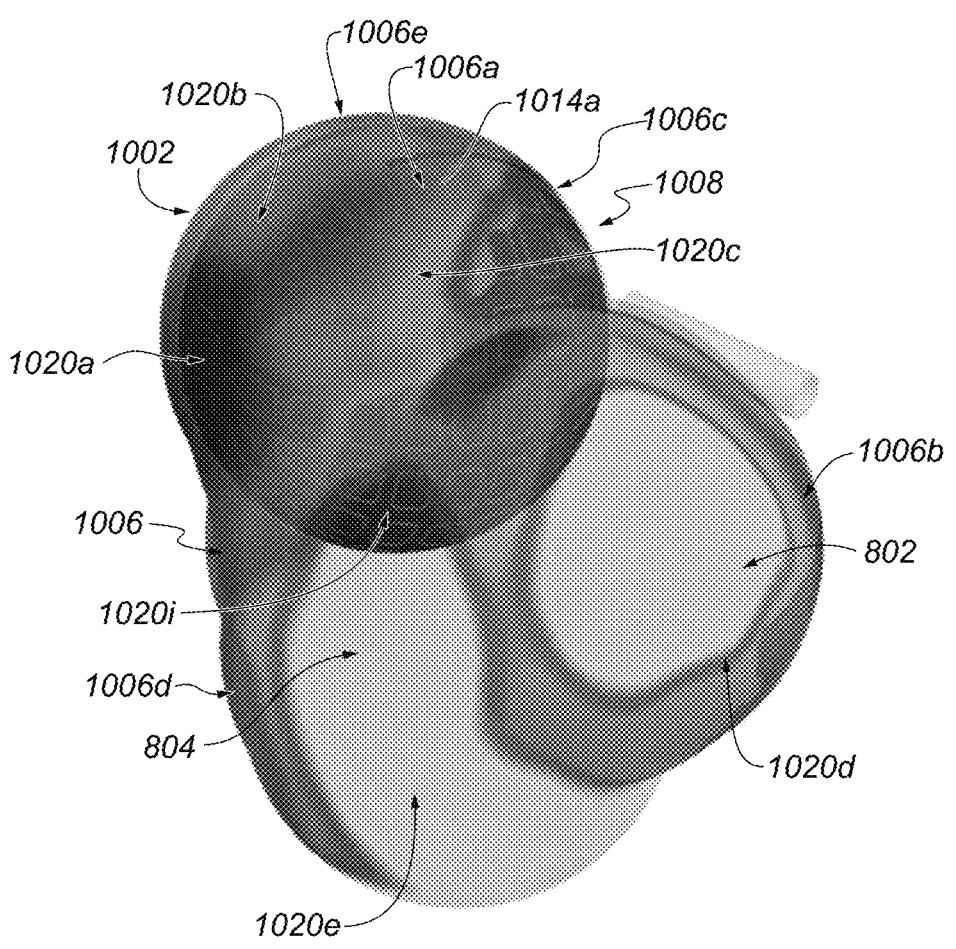

In the state of FIG. 9, representative of the at least the portion of the catheter being at the third location in the sequence of locations (e.g., as determined by the corresponding location signal set received according to program instructions associated with block 1402 in FIG. 14), the data processing device system 110, 310 may be configured (e.g., according to program instructions associated with block 1406 in FIG. 14) at least to determine the present transducer-to-tissue contact state of the transducers (e.g., transducers 220, 306, 406) based on the contact signal set received from such transducers (e.g., according to program instructions associated with block 1404) in the state in which the at least the portion of the catheter is located at the third location represented in FIG. 9. With the present transducer-to-tissue contact state of the transducers, the data processing device system 110, 310 is configured at least to cause the display device system 332 to color (or provide other visual characteristics) the catheter representation 908 (which corresponds to another view of the catheter representation 808 from FIG. 8 but in the third location) to visually indicate such tissue-contact state, as shown in FIG. 9, according to some embodiments. In some embodiments, with the present tissue-contact state determined, the data processing device system 110, 310 is configured (e.g., according to program instructions associated with block 1406 in FIG. 14) at least to utilize the regions of tissue-contact in the present tissue-contact state to enlarge the at least the portion of the envelope, akin to using the catheter representation to stamp the tissue contact regions onto the enlarged at least the portion of the envelope, as illustrated by the sequence of FIG. 9 to FIG. 10, according to some embodiments. In FIG. 10, the progressive enlargement of the portion of the envelope, as compared to FIG. 9, is illustrated by expanded region 1002 of the portion of the envelope.

As illustrated at least by the progression of FIG. 9 to FIG. 10, the data processing device system 110, 310 may be configured (e.g., according to program instructions associated with block 1406 in FIG. 14) at least to cause, during progressively enlarging the envelope, the display device system 332 to visually indicate an envelope enlargement as visually adding a new region 1002, which may include a new tissue-contact region (e.g., illustrated in FIG. 10 at least by envelope coloring 1020b) and a new no-tissue-contact region (e.g., illustrated in FIG. 10 at least by the region 1006c of the visual representation 1006 of the portion of the envelope). FIG. 11 illustrates a state in which the at least the portion of the catheter is in a location in the sequence of locations, subsequent to the third location represented in FIG. 9, where the at least the portion of the catheter has progressed through several locations in the sequence of locations through the bodily cavity and, consequently, the data processing device system has generated several corresponding enlargements to the portion of the envelope according to program instructions associated with block 1406 in FIG. 14.

Returning to FIG. 10, a state is represented in which at least a portion of the catheter (e.g., transducer-based device 200, 300, or 400) is in a particular location (e.g., in the above-discussed "third location") in the sequence of locations (e.g., as determined by the corresponding location signal set received according to the program instructions associated with block 1402 in FIG. 14). In such a state, in some embodiments, the data processing device system 110, 310 is configured (e.g., according to program instructions associated with, e.g., block 1506 in FIG. 15) at least to cause the display device system 332 to display a first set of graphical elements (e.g., including transducer graphical element 1014a in FIG. 10) and a first portion (e.g., at least portion 1006a) of the at least the portion of the envelope in a graphically-overlapping manner, concurrently with a second portion (e.g., at least portion 1006b) of the at least the portion of the envelope displayed without overlapping or being overlapped by any of the transducer graphical elements and in accordance with a particular visual characteristic set indicative of a degree-of-tissue-contact detected, in a prior state representative of the at least the portion of the catheter being in an earlier location (e.g., the initial location associated with representation 806a in FIG. 8) in the sequence of locations, by a particular set of transducers of the plurality of transducers, the earlier location being earlier in the sequence of locations than the particular location in the sequence of locations. For example, in some embodiments, such as at least some of those in which the visual representation 1006 of the portion of the envelope shown in FIG. 10 represents historical transducer-to-tissue contact information (at least in regions where the at least the portion of the catheter is no longer located), and the transducer graphical elements represent present transducer-to-tissue contact information, the regions of the portion of the envelope, such as region 1006b, where the catheter representation 1008 is no longer located, may utilize a particular visual characteristic set indicative of a degree-of-tissue contact detected by transducers in an earlier state in which the at least the portion of the catheter was located in such regions. In some embodiments, such as shown in FIG. 10, the portion (e.g., including first portion 1006a) of the envelope that overlaps the catheter representation 1008 is mutually exclusive with the portion (e.g., including second portion 1006b) of the envelope where no transducer graphical elements are located (since, e.g., the catheter representation 1008 is in a different location within the envelope).

Also, with reference to FIG. 10, in the state in which the catheter representation 1008 is represented at the above-discussed third location in the sequence of locations, the transducer graphical elements (e.g., including graphical element 1014a) of the catheter representation 1008 illustrate degrees of transducer-to-tissue contact detected by the corresponding transducers. For example, in some embodiments, the data processing device system 110, 310 is configured (e.g., according to program instructions associated with, e.g., block 1404 in FIG. 14) at least to receive a first contact signal set from at least a first set of transducers of the plurality of transducers (e.g., transducers 220, 306, 406), the first set of transducers respectively corresponding to a first set of graphical elements (e.g., including at least graphical element 1014a in the example of FIG. 10), according to some embodiments. In some embodiments, the first contact signal set indicates a degree of transducer-to-tissue contact between each transducer of the first set of transducers and a tissue surface within the bodily cavity, and the first contact signal set may correspond to a particular location (e.g., the above-discussed third location illustrated by the location of the catheter representation 1008 in FIG. 10) in the sequence of locations of the at least the portion of the catheter (e.g., transducer-based device 200, 300, or 400) in the bodily cavity. In some embodiments, the data processing device system 110, 310 is configured (e.g., according to program instructions associated with, e.g., block 1404 in FIG. 14) at least to cause the display device system 332 to display, in the state representative of the at least the portion of the catheter being in the particular location (e.g., as represented in at least FIG. 10) in the sequence of locations and based at least on the received first contact signal set (e.g., according to program instructions associated with block 1404), each graphical element in the first set of graphical elements in accordance with a first visual characteristic set (e.g., the coloration of graphical element 1014a shown in FIG. 10) indicating a degree of transducer-to-tissue contact detected by the respective transducer of the at least the first set of transducers of the plurality of transducers.

Also with reference to FIG. 10, in the state in which the catheter representation 1008 is represented at the above-discussed third location in the sequence of locations, the surface or shell of the visual representation 1006 of the portion of the envelope, including regions thereof where the catheter representation 1008 is no longer located (e.g., like region 1006b), may represent historical degrees of transducer-to-tissue contact that were detected in prior states or locations of the at least the portion of the catheter. For example, in some embodiments, the data processing device system 110, 310 is configured (e.g., according to program instructions associated with, e.g., block 1404 in FIG. 14) at least to receive a second contact signal set from a second set of transducers of the plurality of transducers (e.g., transducers 220, 306, 406), the second contact signal set indicating a degree of transducer-to-tissue contact between each transducer of the second set of transducers and a tissue surface within the bodily cavity in the prior state (e.g., the initial location associated with representation 806a in FIG. 8) representative of the at least the portion of the catheter being in the earlier location (e.g., earlier than the above-discussed third location illustrated by the location of the catheter representation 1008 in FIG. 10) in the sequence of locations. In some embodiments, the data processing device system 110, 310 is configured (e.g., according to program instructions associated with, e.g., block 1404 in FIG. 14) at least to cause the display device system 332 to display, in the state representative of the at least the portion of the catheter being in the particular location (e.g., the above-discussed third location illustrated by the location of the catheter representation 1008 in FIG. 10) in the sequence of locations and based at least on the received second contact signal set, the second portion (e.g., at least portion 1006b) of the at least the portion of the envelope displayed without overlapping or being overlapped by any of the graphical elements and with the particular visual characteristic set indicative of the degree-of-tissue-contact detected by the particular set of transducers (e.g., that provided the second contact signal set) in the prior state (e.g., the initial location associated with representation 806a in FIG. 8) representative of the at least the portion of the catheter being in the earlier location in the sequence of locations.

Although various examples discussed above are provided in the context of receiving and displaying tissue contact information indicating various detected degrees of transducer-to-tissue contact, some embodiments of the present invention configure the data processing device system 110, 310 to receive and cause visual presentation of other types of information from the transducers (e.g., transducers 220, 306, 406). For instance, in some embodiments, the data processing device system 110, 310 is configured to receive and cause visual presentation of tissue-electrical-information signal sets that indicate an electrical property set (e.g., a set of one or more electrical properties) of tissue in the bodily cavity (or other cavity in a quality-control, training, or testing environment) detected by one or more of the transducers. The electrical property set may be tissue electrical characteristics as discussed above, including, e.g., one or more electric potentials of a tissue surface of the bodily cavity, e.g., as detected by the respective transducers (e.g., transducers 220, 306, 406).

For instance, FIG. 12A provides an example of a graphical user interface visually presented by the display device system 332, in a catheter-location-sequence state that corresponds to FIG. 10, but instead of visually representing detected tissue-contact information via the visual representation 1006 of the portion of the envelope and the catheter representation 1008 shown in FIG. 10, detected tissue-electrical information is visually represented by the visual representation 1206 of the portion of the envelope and the catheter representation 1208 shown in FIG. 12A, according to some embodiments. In the example of FIG. 12A, different voltage values detected by corresponding transducers are represented, with the values represented by the visual representation 1206 of the portion of the envelope representing historical detected values (at least in regions where the at least the portion of the catheter is no longer located, as with the case for detected tissue-contact information discussed above), and with the values represented by the catheter representation 1208 representing present detected values. Different visual characteristics may be utilized to represent such detected tissue-electrical information (e.g., as shown in FIG. 12A) as compared to the detected tissue-contact information (e.g., as shown in FIG. 10).

In the example of FIG. 12A, a different color palette and mapping thereof to detected degrees of tissue-electrical information is utilized compared to that shown in FIG. 10 for detected tissue-contact information. Although FIG. 12A appears in variations of gray, the actual color palette utilized to represent the detected degrees of tissue-electrical information via the visual representation 1206 of the portion of the envelope includes (in order of highest determined value or range to lowest determined value or range) a range of magenta colors 1220a, a range of blue colors 1220b, a range of cyan colors 1220c, a range of green colors 1220d, a range of yellow colors 1220e, a range of orange colors 1220f, and transparency 1220g (signifying detected tissue-electrical information at a location associated with no-detected transducer-to-tissue contact or minimal transducer-to-tissue contact and, therefore, such tissue-electrical information is not displayed), the color palette collectively visually indicating different degrees of detected tissue-electrical information, according to some embodiments. In some embodiments, the same color palette utilized to represent the detected degrees of tissue-electrical information via the visual representation 1206 of the portion of the envelope is utilized to represent the detected degrees of tissue-electrical information via the catheter representation 1208 and its transducer graphical elements. Although, in the example of FIG. 12A, detected tissue-electrical information at a location associated with no-detected transducer-to-tissue contact is represented via the visual representation 1206 of the portion of the envelope with transparency 1220g, detected tissue-electrical information at a location associated with no-detected transducer-totissue contact is represented via the catheter representation 1208 via a medium gray color 1220h, according to some embodiments.

In contrast, in the example of FIG. 10, although FIG. 10 appears in variations of gray, the actual color palette utilized to represent the detected degrees of tissue-contact information via the visual representation 1006 of the portion of the envelope includes (in order of highest detected value to lowest detected value) a range of dark green colors 1020a, a range of medium green colors 1020b, a range of light green colors 1020c, a range of blue colors 1020d, and transparency 1020e (signifying no detected tissue-contact or minimal detected tissue-contact within a threshold), the color palette collectively visually indicating different degrees of detected tissue-contact information, according to some embodiments. In some embodiments, the same color palette utilized to represent the detected degrees of tissue-contact information via the visual representation 1006 of the portion of the envelope is utilized to represent the detected degrees of tissue-contact information via the catheter representation 1008 and its transducer graphical elements. Although, in the example of FIG. 10, no detected tissue-contact information is represented via the visual representation 1006 of the portion of the envelope with transparency 1020e, no detected tissue-contact information is represented via the catheter representation 1008 via a shade of blue color 1020i, according to some embodiments.

In some embodiments, the data processing device system 110, 310 is configured according to program instructions at least to cause the display device system 332 to visually represent, based at least on some tissue-electrical-information signals of the plurality of tissue-electrical-information signal sets provided by at least some transducers, at least a portion of the envelope (e.g., as represented by visual representation 1206 in FIG. 12A) in a manner that visually indicates at least a portion of an electrical property set in at least some of the greater-tissue-contact regions, but with no visual indication of the electrical property set in at least a particular lesser-tissue-contact region associated with no transducer-to-tissue contact. In some embodiments, the data processing device system 110, 310 is configured according to program instructions at least to cause the display device system 332 to visually represent, based at least on some tissue-electrical-information signals of the plurality of tissue-electrical-information signal sets and at least some contact signals of the plurality of contact signal sets, at least a portion of the envelope (e.g., as represented by visual representation 1206 in FIG. 12A) in a manner that visually indicates at least a portion of the electrical property set in at least some of the greater-tissue-contact regions, but with no visual indication of the electrical property set in at least a particular lesser-tissue-contact region associated with no transducer-to-tissue contact. For example, as shown in FIG. 12A, the visual representation 1206 of the at least the portion of the envelope visually indicates detected degrees of electric potential of the tissue surface in the regions (e.g., regions 1206a, 1206b, 1206c) of such visual representation 1206 where tissue-contact was detected (compare, e.g., FIG. 10), but the visual representation 1206 does not include a visual indication of electric potential in the regions (e.g., regions of port representations 802, 804 in FIG. 12A) where no tissue-contact was detected (e.g., compare FIG. 10). As with the contact signal sets associated with block 1404 in FIG. 14, at least a portion of the electrical property set detected by at least some transducers may be visually indicated in the tissue-contact regions but not in the no-tissue-contact regions of the at least the portion of the envelope throughout each enlargement of the envelope (e.g., akin to FIGS. 8-11). In some embodiments, at least one of the tissue-contact regions or greater tissue-contact regions (e.g., at least region 1221*a* in FIG. 12A) where the electrical property set is visually indicated via the visual representation 1206, and at least one no-tissue-contact region (e.g., at least the region 807 in FIG. 12A) where there is no visual indication of the electrical property set, are located in a first portion (e.g., region 1206*a*) of the at least the portion of the envelope where the catheter representation 1208 is located. In some embodiments, at least one of the tissue-contact regions or greater tissue-contact regions (e.g., at least region 1221*b* in FIG. 12A) where the electrical property set is visually indicated via the visual representation 1206, and at least one no-tissue-contact region (e.g., at least the region of port representation 802 in FIG. 12A) where there is no visual indication of the electrical property set, are located in a second portion (e.g., region 1206*b*) of the at least the portion of the envelope where the catheter representation 1208 is not located. In some embodiments, at least one of the tissue-contact regions or greater tissue-contact regions (e.g., at least region 1221*a*) where the electrical property set is visually indicated via the visual representation 1206 are located in the first portion (e.g., region 1206*a*) of the at least the portion of the envelope where the catheter representation 1208 is located, and at least one no-tissue-contact region (e.g., at least the region of port representation 802) where there is no visual indication of the electrical property set, is located in the second portion (e.g., region 1206*b*) of the at least the portion of the envelope where the catheter representation 1208 is not located.

As with the tissue-contact information discussed above with respect to at least FIGS. 8-11, the tissue-electrical information (e.g., represented by at least FIG. 12A) may be visually represented via the visual representation 1206 of the portion of the envelope, the catheter representation 1208, or both, according to some embodiments. In some embodiments, the graphical user interface (e.g., displayed via display device 332) concurrently displays tissue-contact information and tissue-electrical information. For instance, graphical representations like FIGS. 10 and 12A (or FIG. 12B, which is identical to FIG. 12A, but without transducer graphical elements) may be concurrently displayed side-by-side to provide the operator with concurrent views of both tissue-contact information and tissue-electrical information. In some embodiments, tissue-electrical information may be visually presented via the visual representation of the portion of the envelope (like visual representation 1206), while tissue-contact information may be visually presented via the catheter representation (like catheter representation 1008) and its transducer graphical elements, if present. Or, vice versa, tissue-contact information may be visually presented via the visual representation of the portion of the envelope (like visual representation 1006), while tissue-electrical information may be visually presented via the catheter representation (like catheter representation 1208) and its transducer graphical elements, if present, according to some embodiments. In some embodiments, the visual representation of the at least the portion of the envelope visually represents the tissue electrical property set, and the transducer graphical elements visually represent detected degrees of transducer-to-tissue contact. For instance, in some embodiments, the data processing device system 110, 310 is configured by program instructions at least to cause a graphical representation (e.g., akin to at least FIG. 10, 12A, or 12B) to include a visual representation, on at least a part of the envelope, of at least a portion of the electrical property set while the graphical representation includes the visual representation, in the graphically-overlapping manner, of at least (a) at least the portion of the envelope and (b) the plurality of graphical elements, with the graphical representation including the display of the at least a first graphical element in accordance with a first visual characteristic set indicating the first degree of transducer-to-tissue contact, and with the graphical representation including the display of the at least the second graphical element in accordance with the second visual characteristic set indicating the second degree of transducer-to-tissue contact. In this regard, transducer graphical elements may visually represent transducer-to-tissue contact with one visual characteristic set (e.g., the colorations used in the examples of FIGS. 8-11), and the visual representation of the at least the portion of the envelope may visually represent the detected electrical property set with another visual characteristic set (e.g., the colorations used in the example of FIG. 12A or 12B), according to some embodiments.

In embodiments where tissue-electrical information is visually presented, the above-discussed methods 1400 and 1500 and, particularly block 1404, may be altered to replace contact signal sets with tissue-electrical-information signal sets. Or, a block similar to block 1404 may be added in parallel to blocks 1402 and 1404 feeding into block 1406 (or block 1506) where tissue-electrical-information signal sets are received by the data processing device system 110, 310 from the respective transducers. As with the contact signal sets associated with block 1404, the tissue-electrical-information signal sets may be received by the data processing device system 110, 310 throughout movement of the at least the portion of the catheter among the sequence of locations in which it moves through the bodily or other cavity. Also, as with the contact signal sets associated with block 1404, each tissue-electrical-information signal set may correspond to a respective location in the sequence of locations in which the at least the portion of the catheter (e.g., transducer-based device 200, 300, 400) progresses through the bodily or other cavity. In some embodiments, the same or different transducers (e.g., transducers 220, 306, 406) may provide the contact signal sets and the tissue-electrical-information signal sets. For instance, a first set of transducers may provide the contact signal sets, and a second set of transducers may provide the tissue-electrical-information signal sets. In some embodiments, the first set of transducers may be the same as the second set of transducers in instances where the same transducers provide both types of signal sets.

As discussed above, according to various embodiments, the same or different detected properties may be visually represented via, e.g., the visual representation 1206 of the portion of the envelope, the catheter representation 1208, or both the visual representation 1206 of the portion of the envelope and the catheter representation 1208. Such a detected property (e.g., detected by one or more transducers 220, 306, 406) may be, but is not limited to, a property responsive to transducer-to-tissue contact, a property responsive to fluid flow in the bodily cavity, a property responsive to temperature, or an electrical property (including, but not limited to an electrical property generated at least in part by a body that include the bodily cavity), such that, e.g., the visual representation 1206 of the portion of the envelope and the catheter representation 1208 visually represent the same or different ones of these detected properties, according to various embodiments.

In this regard, in some embodiments, the data processing device system 110, 310 is configured by program instructions at least to receive a plurality of location signal sets, e.g., from a catheter-device-location tracking system (e.g., as discussed above), according to some embodiments. As discussed above, each location signal set of the plurality of location signal sets may be indicative of a respective location in a sequence of locations at which the at least the portion of the catheter (e.g., transducer-based device 200, 300, 400) has been sequentially located in the bodily cavity. In some embodiments, the catheter may include a first transducer set and a second transducer set, such that each transducer in the first transducer set is configured to detect at least a first property at least in a state in which the at least the portion of the catheter is located within the bodily cavity, and each transducer in the second transducer set configured to detect at least a second property at least in the state in which the at least the portion of the catheter is located within the bodily cavity, the first property different in type than the second property. For example, the first transducer set may be configured to detect a property responsive to transducer-to-tissue contact, and the second transducer set may be configured to detect a tissue electrical property. The first transducer set may be the same as the second transducer set, such that, e.g., the same set of one or more transducers detects the first and second properties, according to some embodiments. However, in some embodiments, the first transducer set is different than the second transducer set.

In some embodiments, the data processing device system 110, 310 is configured by program instructions at least to cause, at least in a state representative of the at least the portion of the catheter being in a particular location in the sequence of locations, the display device system 332 to display a graphical representation (e.g., akin to at least FIG. 10, 12A, or 12B), the graphical representation including a visual representation, in a graphically-overlapping manner, of at least (a) at least a portion of an envelope (like visual representation 1006 or 1206) representing an interior volume of the bodily cavity, and (b) the at least the portion of the catheter (like catheter representation 1008 or 1208). In this regard, the at least the portion of the catheter may be visually represented (i) in accordance with a first property visual characteristic set (e.g., the colorations used in the examples of FIGS. 8-11 at least in the case of detected degrees of tissue surface contact or other visual characteristic set for the same or another property) indicating the first property detected by at least one transducer of the first transducer set, and (ii) based at least on some location signals of a particular location signal set of the plurality of location signal sets representing the particular location in the sequence of locations of the at least the portion of the catheter in the bodily cavity. For example, when the at least the portion of the catheter is at the particular location in the bodily cavity, a catheter-device-location tracking system (e.g., per FIGS. 2-4) may generate a particular location signal set identifying positions of a plurality of transducers 220, 306, 406 of the catheter, one or more of such transducers may be considered a first transducer set, at least one transducer of which detects a degree of the first property (e.g., tissue contact or other property as discussed above). With the position of at least the one or more transducers that detected the respective degree(s) of the first property, based on the location signal(s) of the particular location signal set, and with the detected respective degree(s) of the first property, the data processing device system 110, 310 is configured by program instructions at least to cause, at least in the state representative of the at least the portion of the catheter being in the particular location in the sequence of locations, the display device system 332 to display at least the visual representation of the at least the portion of the catheter in accordance with the first property visual characteristic set, according to some embodiments. In this manner, the visual representation of the at least the portion of the catheter may visually represent various detected degrees or levels of the first property at least in the state representative of the at least the portion of the catheter being in the particular location in the sequence of locations.

On the other hand, a region of the at least the portion of the envelope may be visually represented (iii) in accordance with a second property visual characteristic set (e.g., the colorations used in the example of FIG. 12A or 12B at least in the case of detected degrees of an electrical property or other visual characteristic set for the same or another property) indicating the second property detected by at least one transducer of the second transducer set, and (iv) based at least on some location signals of the plurality of location signal sets representing the sequence of locations of the at least the portion of the catheter in the bodily cavity, the second property visual characteristic set different than the first property visual characteristic set. For example, based on some location signals from historical location signal sets or a present location signal set, or both, indicating prior, present, or both prior and present locations of the at least the portion of the catheter in the bodily cavity, at least when the at least the portion of the catheter is at the particular location in the bodily cavity, and based on past, present, or both past and present degrees of the second property detected by one or more transducers 220, 306, 406 of a second transducer set, at least a region of the at least the portion of the envelope may be visually represented to indicate information pertaining to the detected degrees of the second property, according to some embodiments. In this manner, the visual representation of the region of the at least the portion of the envelope may visually represent various detected degrees or levels of the second property, according to some embodiments.

With the visual representation of the at least the portion of the catheter visually representing, e.g., various present detected degrees or levels of the first property, and with the visual representation of the region of the at least the portion of the envelope visually representing, e.g., various historical detected degrees or levels of the second property, a graphical representation may be provided as including a composition of something like the catheter representation 1008 from FIG. 10 (in the case where the first property is tissue contact) and the visual representation 1206 of the portion of the envelope from FIG. 12A or 12B (in the case where the second property is an electrical property), according to some embodiments.

In this regard, according to some embodiments, the visual representation of the at least the portion of the catheter may include the above-discussed graphical elements respectively corresponding to transducers (e.g., transducers 220, 306, 406) of the catheter, such that at least a first graphical element (e.g., like transducer graphical element 1014a in FIG. 10) is displayed as located in a first region of the visually represented the at least the portion of the envelope and in accordance with a first visual characteristic set, such as the above-discussed first property visual characteristic set, indicating the first property. The first graphical element may correspond to a first transducer in the first transducer set, the first transducer detecting the first property at least in the state representative of the at least the portion of the catheter being in the particular location in the sequence of locations. In this manner, the visual representation of the at least the portion of the catheter, along with its transducer graphical elements, may visually represent the respective degrees or levels of the first property detected by the corresponding transducers, according to some embodiments.

As discussed above, according to various embodiments, the same or different detected properties may be visually represented via, e.g., the visual representation 1206 of the portion of the envelope, the catheter representation 1208, or both the visual representation 1206 of the portion of the envelope and the catheter representation 1208. In some embodiments, user input may control what detected property or properties is or are displayed via, e.g., the visual representation 1206 of the portion of the envelope, the catheter representation 1208, or both the visual representation 1206 of the portion of the envelope and the catheter representation 1208. For example, the data processing device system 110, 310 may be configured by program instructions at least to receive user input via the input-output device system (e.g., 120, 320), and to cause the display device system 332 to update the graphical representation, at least in response to the user input, to change the property or properties that is or are displayed via, e.g., the visual representation 1206 of the portion of the envelope, the catheter representation 1208, or both the visual representation 1206 of the portion of the envelope and the catheter representation 1208, according to some embodiments. In instances where, for example, a first graphical element of the catheter representation 1208 corresponding to a particular transducer is displayed in accordance with a first visual characteristic set indicating a first property, and the user input requests, e.g., that the first graphical element (or, more broadly, the catheter representation 1208) now represent a particular property different in type than the first property, the data processing device system 110, 310 may be configured to cause the display device system 332 to update the graphical representation so that at least the first graphical element (or more broadly the catheter representation 1208) is now displayed in accordance with a second visual characteristic set indicating the particular property detected by at least the first transducer at least in the state in which the at least the portion of the catheter is located within the bodily cavity, according to some embodiments. The second visual characteristic set may be different than the first visual characteristic set to visually inform the user that the particular property is now being displayed.

In instances where the first property is, e.g., tissue contact, and the newly-user-selected particular property is an electrical property (e.g., a second property) that was being displayed by, e.g., the visual representation 1206 of the portion of the envelope, the result of the change may be that both the catheter representation 1206 and the visual representation 1206 of the portion of the envelope visually represent the electrical property, such as the state of the graphical representation shown in FIG. 12A or 12B, according to some embodiments. While the preceding example considered a case where the newly-user-selected particular property was the same as the second property, which was being displayed by the visual representation of the portion of the envelope, various embodiments allow for the newly-user-selected particular property, as well as the property represented by the portion of the envelope to be any detectable property. Also, while the above examples discussed a user changing the property displayed by the catheter representation (e.g., 1008 or 1208), a similar approach may be applied to changing the displayed property of, e.g., the visual representation (e.g., 1006 or 1206) of the portion of the envelope.

Due at least to user input requesting changing of displayed parameters by the catheter representation (e.g., 1008 or 1208), the visual representation (e.g., 1006 or 1206) of the portion of the envelope, or both the catheter representation (e.g., 1008 or 1208) and the visual representation (e.g., 1006 or 1206) of the portion of the envelope, different properties may be displayed at different times. For example, FIG. 8 may represent a state in which the at least the portion of the catheter is at a first particular location in the bodily cavity, and both the catheter representation 808 and the visual representation 806 of the portion of the envelope illustrate various presently-detected and historically-detected degrees or levels of tissue contact, respectively. However, if the user subsequently requests that the catheter representation and the visual representation of the portion of the envelope represent an electrical property other than the tissue contact, FIG. 12A or 12B may then represent a state in which the at least the portion of the catheter is at a second particular location in the bodily cavity, and both the catheter representation 1208 and the visual representation 1206 of the portion of the envelope illustrate various presently-detected and historically-detected degrees or levels of the electrical property, respectively. Consequently, in the state in which the at least the portion of the catheter was at the first particular location in the bodily cavity (represented by FIG. 8 in this example), the catheter representation 808 and the visual representation 806 of the portion of the envelope represented a first property according to respective visual characteristic sets, according to some embodiments. But, in the state in which the at least the portion of the catheter is at the second particular location in the bodily cavity (represented by, e.g., FIG. 12A (with transducer graphical elements) or FIG. 12B (without transducer graphical elements)), the catheter representation 808 and the visual representation 806 of the portion of the envelope represent a second property according to different respective visual characteristic sets, according to some embodiments.

Described in a different way, in some embodiments, the data processing device system 110, 310 is configured by program instructions at least to cause, during the progressively visually representing in the progressively enlarging manner of the at least the portion of the envelope, and based at least on some location signals of a first particular location signal set representing a first particular location (e.g., the location of the catheter represented by FIG. 8) in the sequence of locations of the at least the portion of the catheter in the bodily cavity, the display device system 332 to display, in a graphically-overlapping manner, at least (a) a visual representation of a first particular envelope enlargement (e.g., the envelope enlargement represented in FIG. 8) leading to the at least the portion of the envelope, and (b) a first visual representation of the at least the portion of the catheter (e.g., catheter representation 808, although transducer graphical elements, such as graphical elements 814a, 814b, 814c, 814d, 814e, 814f, 814g, and 814h, may or may not be included according to various embodiments), the first visual representation of the at least the portion of the catheter displayed in accordance with a first property visual characteristic set (e.g., the coloration of the catheter representation 808) indicating a first property (e.g., tissue contact in the example of FIG. 8) detected by one or more transducers of the plurality of transducers at least in a first state representative of the at least the portion of the catheter being in the first particular location in the sequence of locations. In this regard, according to some embodiments, the data processing device system 110, 310 is configured by program instructions at least to cause, during the progressively visually representing in the progressively enlarging manner and based at least on some location signals of a second particular location signal set representing a second particular location (e.g., the location of the catheter represented by FIG. 12A) in the sequence of locations of the at least the portion of the catheter in the bodily cavity, the display device system 332 to display, in a graphically-overlapping manner, at least (c) a visual representation of a second particular envelope enlargement (e.g., the envelope enlargement represented in FIG. 12A) leading to the at least the portion of the envelope, and (d) at least a second visual representation of the at least the portion of the catheter (e.g., catheter representation 1208), the second visual representation of the at least the portion of the catheter displayed in accordance with a second property visual characteristic set (e.g., the coloration of the catheter representation 1208) indicating a second property (e.g., an electrical property in the example of FIG. 12A) detected by one or more transducers of the plurality of transducers at least in a second state representative of the at least the portion of the catheter being in the second particular location in the sequence of locations, the second property visual characteristic set different than the first property visual characteristic set, and the second property different in type than the first property, according to some embodiments.

Continuing with this example, FIGS. 8 and 12A include, according to some embodiments, transducer graphical elements on the catheter representations 808 and 1208, respectively, so at least a first graphical element of these graphical elements indicates the detected degree of the first property by its corresponding transducer in the first state associated with FIG. 8, but indicates the detected degree of the second property by its corresponding transducer in the second state associated with FIG. 12A. The transducer graphical elements, including the first graphical element, may utilize the same visual characteristic set utilized by the catheter representation 808 and 1208, respectively, according to some embodiments.

Also continuing with the above example, at least in the first state (e.g., represented by FIG. 8 in this example) representative of the at least the portion of the catheter being in the first particular location in the sequence of locations, the visual representation of the first particular envelope enlargement (e.g., the envelope enlargement represented by FIG. 8 in this example) leading to the at least the portion of the envelope may be displayed in accordance with a third property visual characteristic set (e.g., a visual characteristic set that may be different than the color palette used for catheter representation 808 and the catheter representation 1208 in FIG. 12A) indicating a particular property detected by a first transducer set of the plurality of transducers at least in the first state representative of the at least the portion of the catheter being in the first particular location in the sequence of locations. The particular property (e.g., which may be tissue contact represented by the visual representation 806 of the at least the portion of the envelope in FIG. 8) being the same as the first property (which may be tissue contact represented by the catheter representation 808 in FIG. 8), according to some embodiments. However, the particular property need not be the same as the first property and may be any detectable property, according to some embodiments.

Similarly, for example, at least in the second state (e.g., represented by FIG. 12A in this example) representative of the at least the portion of the catheter being in the second particular location in the sequence of locations, the visual representation of the second particular envelope enlargement (e.g., the envelope enlargement represented by FIG. 12A in this example) leading to the at least the portion of the envelope is displayed in accordance with a third property visual characteristic set (e.g., a visual characteristic set that may be different than the color palette used for catheter representation 808 and the catheter representation 1208 in FIG. 12A) indicating a particular property detected by a first transducer set of the plurality of transducers at least in the second state representative of the at least the portion of the catheter being in the second particular location in the sequence of locations, according to some embodiments. The particular property (e.g., which may be the electrical property represented by the visual representation 1206 of the at least the portion of the envelope in FIG. 12A) may be the same as the second property (which may be the electrical property represented by the catheter representation 1208 in FIG. 12A), according to some embodiments. However, the particular property need not be the same as the second property and may be any detectable property including the first property (which may be tissue contact represented by the catheter representation 808 in FIG. 8), according to some embodiments.

For a different example, in some embodiments, at least in a first state (e.g., represented by FIG. 8 in this particular example) representative of the at least the portion of the catheter being in the first particular location in the sequence of locations, the visual representation of the first particular envelope enlargement (e.g., the envelope enlargement represented by expanded portion 806d in FIG. 8 in this particular example) leading to the at least the portion of the envelope is displayed in accordance with a first particular visual characteristic set (e.g., the coloration of the expanded portion 806d of the envelope in FIG. 8 in this particular example), according to some embodiments. In some embodiments, at least in a second state (e.g., represented by at least FIG. 10 in this particular example) representative of the at least the portion of the catheter being in the second particular location in the sequence of locations, the visual representation of the first particular envelope enlargement (e.g., portion 1006d of the visual representation of the envelope in FIG. 10 corresponding to the first particular envelope enlargement 806d from FIG. 8 in this particular example) leading to the at least the portion of the envelope is displayed in accordance with a second particular visual characteristic set (e.g., the coloration of the portion 1006d of the visual representation of the envelope in FIG. 10 in this particular example). The second particular visual characteristic set (e.g., the coloration of the portion 1006d of the visual representation of the envelope in FIG. 10 in this particular example) may be the same as the first particular visual characteristic set (e.g., the coloration of the expanded portion 806d of the envelope in FIG. 8 in this particular example), according to some embodiments. In some embodiments, at least in the second state (e.g., represented by at least FIG. 10 in this particular example) representative of the at least the portion of the catheter being in the second particular location in the sequence of locations, the visual representation of the second particular envelope enlargement (e.g., the envelope enlargement 1006e represented by FIG. 10 in this particular example) leading to the at least the portion of the envelope is displayed in accordance with a third particular visual characteristic set (e.g., the coloration of the expanded portion 1006e of the envelope in FIG. 10 in this particular example), according to some embodiments. The third particular visual characteristic set may be the same as the first particular visual characteristic set and the second particular visual characteristic set, according to some embodiments.

Figure 13:
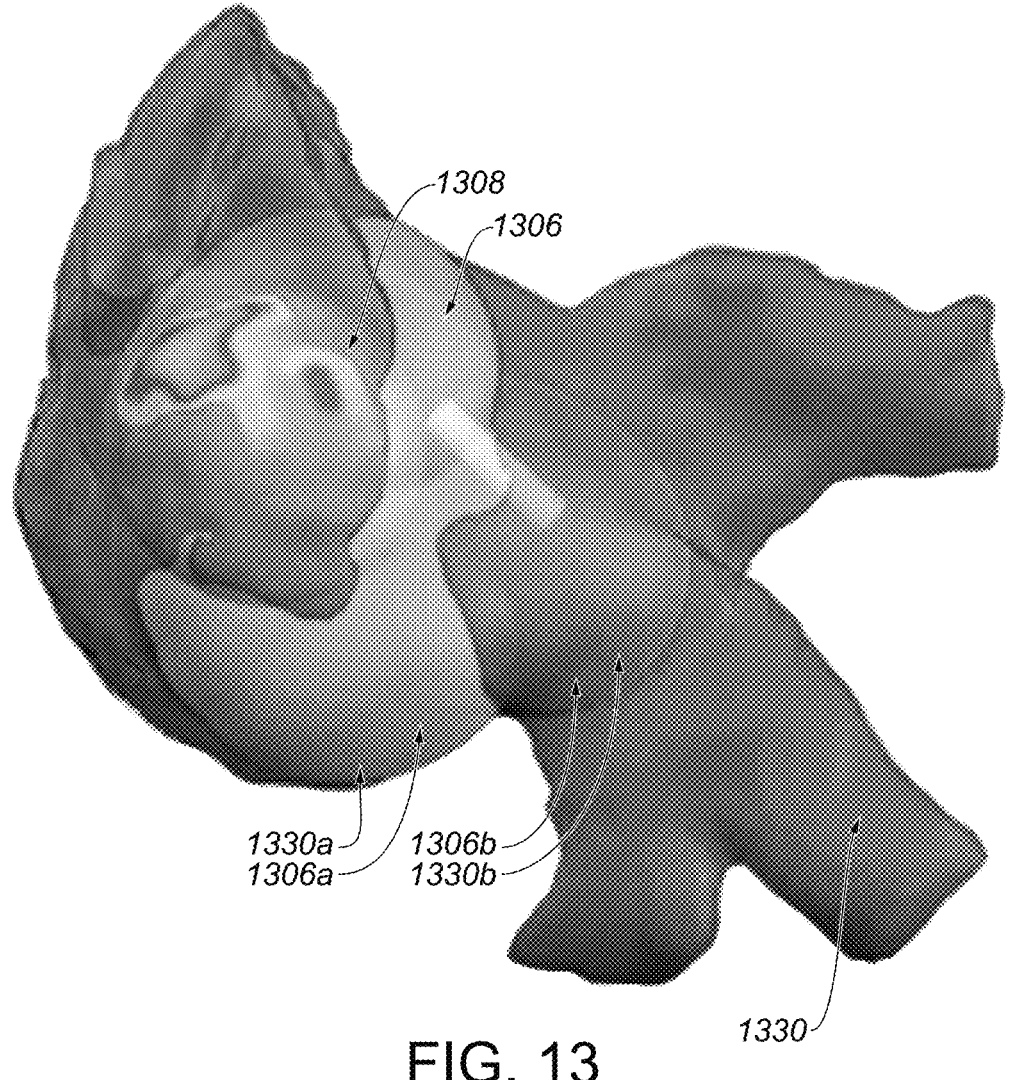
FIG. 13 illustrates, according to various example embodiments, a graphical representation, presented via a display device system, of: a portion of an envelope representing an interior volume of a bodily cavity, in this instance, a left atrium of a heart; a portion of a transducer-based device, like the ones illustrated at least in FIGS. 4 and 6; and of a pre-existing image of the bodily cavity, in this instance, a pre-existing computed tomography (CT) image, the graphical representation of the portion of the transducer-based device, in this instance, not including graphical representations of transducer graphical elements representing transducers of the transducer-based device, and, in this instance, the graphical representations of the portion of the transducer-based device, but not the portion of the envelope, indicating degrees of detected tissue contact.

With reference to the example of FIG. 13, in some embodiments, to further assist navigation of the catheter, the data processing device system 110, 310, may be configured (e.g., according to program instructions associated with block 1406 in FIG. 14) at least to cause the display device system 332 to concurrently display a pre-existing image of the bodily cavity, such as a computed tomography (CT or CAT) scan image 1330 with (a) the at least the portion of the envelope (e.g., shown in FIG. 13 with visual representation 1306 of the at least the portion of the envelope), (b) the plurality of graphical elements (not shown in the catheter representation 1308 in FIG. 13, but may be akin to at least catheter representation 808), (c) a pre-existing image of the bodily cavity, such as a computed tomography (CT or CAT) scan image 1330, (a) and (b), (b) and (c), (a) and (c), or (a), (b), and (c). In some embodiments, as illustrated in FIG. 13, the at least the portion of the envelope (e.g., shown in FIG. 13 with visual representation 1306 of the at least the portion of the envelope) and the catheter representation 1308 (and its transducer graphical elements, if present) graphically overlap with at least a portion of the pre-existing image 1330 of the bodily cavity. In some embodiments, the data processing device system 110, 310 is configured at least by the program at least to cause the display device system 332 to concurrently display at least a first part (e.g., first part 1306a) of the at least the portion of the envelope graphically overlapping a first portion (e.g., first portion 1330a) of the pre-existing image 1330 of the bodily cavity, while concurrently displaying a second portion (e.g., second portion 1330b) of the pre-existing image 1330 of the bodily cavity graphically overlapping at least a second part (e.g., second part 1306b) of the at least the portion of the envelope. In this regard, as shown in FIG. 13, at the location of the first part 1306a of the at least the portion of the envelope and the location of the first portion 1330a of the pre-existing image 1330 of the bodily cavity, the first part 1306a of the at least the portion of the envelope is located outside of the first portion 1330a of the pre-existing image 1330 of the bodily cavity (e.g., as indicated by the lightly shaded grey portions in FIG. 13). Such a circumstance may indicate, among other things, that the at least the portion of the envelope represents a state in which the corresponding wall of the bodily cavity has been stretched by force applied by the at least the portion of the catheter when that portion of the envelope was generated. On the other hand, as shown in FIG. 13, at the location of the second part 1306b of the at least the portion of the envelope and the location of the second portion 1330b of the pre-existing image 1330 of the bodily cavity, the second part 1306b of the at least the portion of the envelope is located inside the second portion 1330b of the pre-existing image 1330 of the bodily cavity. Such a circumstance may indicate, among other things, that the at least the portion of the envelope represents a state in which the visual representation of the portion of the envelope and the pre-existing image of the bodily cavity are not properly aligned or registered. On the other hand, such a circumstance may also indicate, among other things, that the portion of the catheter was not sufficiently pressed against the corresponding wall of the bodily cavity when the portion of the catheter was at that location in the sequence of locations. Significant misalignment between the pre-existing image 1330 of the bodily cavity and the visual representation 1306 of the at least the portion of the envelope may indicate, at least in part, that the pre-existing image 1330 needs to be moved with respect to the visual representation 1306 of the at least the portion of the envelope, or vice versa, to improve registration between the two.

While some of the embodiments disclosed above are described with examples of cardiac mapping, the same or similar embodiments may be used for mapping other bodily organs, for example gastric mapping, bladder mapping, arterial mapping and mapping of any lumen or cavity into which the devices of the present invention may be introduced.

While some of the embodiments disclosed above are described with examples of cardiac ablation, the same or similar embodiments may be used for ablating other bodily organs or any lumen or cavity into which the devices of the present invention may be introduced.

Subsets or combinations of various embodiments described above can provide further embodiments.

These and other changes can be made to the invention in light of the above-detailed description. In general, in the following claims, the terms used should not be construed to limit the invention to the specific embodiments disclosed in the specification and the claims, but should be construed to include other catheter or transducer-based device systems including all medical treatment device systems and all medical diagnostic device systems in accordance with the claims. Accordingly, the invention is not limited by the disclosure, but instead its scope is to be determined entirely by the following claims.

What is claimed is:

1. A catheter navigation system comprising:
an input-output device system communicatively connected to a display device system;
a memory device system storing a program; and
a data processing device system communicatively connected to the input-output device system and the memory device system, the data processing device system configured at least by the program at least to:
receive a plurality of location signal sets, each location signal set of the plurality of location signal sets indicative of a respective location in a sequence of locations at which at least a portion of a catheter has sequentially moved to in a bodily cavity, the catheter comprising a plurality of transducers arrangeable in a first spatial distribution, each transducer of the plurality of transducers configured to detect a degree of transducer-to-tissue contact; and
generate and cause the display device system to concurrently display, in a state representative of the at least the portion of the catheter being in a particular location in the sequence of locations, at least (a) at least a portion of an envelope representing an interior volume of the bodily cavity based at least on the received plurality of location signal sets, and (b) a plurality of graphical elements, each graphical element corresponding to a transducer of the plurality of transducers,
wherein the generating and causing the display device system to concurrently display at least (a) and (b) includes, in the state representative of the at least the portion of the catheter being in the particular location in the sequence of locations, a display of a first set of graphical elements of the plurality of graphical elements and a first portion of the at least the portion of the envelope in a graphically-overlapping manner, concurrently with a second portion of the at least the portion of the envelope displayed without overlapping or being overlapped by any of the graphical elements and in accordance with a particular visual characteristic set indicative of a degree-of-tissue-contact detected, in a prior state representative of the at least the portion of the catheter being in an earlier location in the sequence of locations, by a particular set of transducers of the plurality of transducers, the earlier location being earlier in the sequence of locations than the particular location in the sequence of locations, wherein the data processing device system is configured at least by the program at least to cause the plurality of graphical elements to be graphically displayed, in the state representative of the at least the portion of the catheter being in the particular location in the sequence of locations, in a second distribution consistent with the first spatial distribution, and wherein the first portion of the at least the portion of the envelope is mutually exclusive with the second portion of the at least the portion of the envelope.

2. The catheter navigation system of claim 1, wherein the data processing device system is configured at least by the program at least to:

receive a plurality of contact signal sets from a first set of transducers of the plurality of transducers, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity; and generate an interpolated portion of the at least the portion of the envelope at least by determining interpolating tissue contact values based at least on an analysis of tissue contact values indicated by (i) a first contact signal set of the plurality of contact signal sets associated with the first portion of the at least the portion of the envelope, and (ii) a second contact signal set of the plurality of contact signal sets associated with the second portion of the at least the portion of the envelope, wherein the generating and causing the display device system to concurrently display at least (a) and (b) includes, in the state representative of the at least the portion of the catheter being in the particular location in the sequence of locations, a display of the interpolated portion of the at least the portion of the envelope between the first portion of the at least the portion of the envelope and the second portion of the at least the portion of the envelope.

3. The catheter navigation system of claim 1, wherein the data processing device system is configured at least by the program at least to cause all graphical elements of the first set of graphical elements corresponding to respective ones of the plurality of transducers associated with a same degree of detected transducer-to-tissue contact to exhibit a same visual characteristic indicating the same degree of transducer-to-tissue contact.

4. The catheter navigation system of claim 3, wherein the data processing device system is configured at least by the program at least to cause graphical elements of the first set of graphical elements corresponding to respective ones of the plurality of transducers associated with different degrees of detected transducer-to-tissue contact to exhibit different visual characteristics indicating the different degrees of detected transducer-to-tissue contact.

5. The catheter navigation of claim 4, wherein the particular visual characteristic set, which is associated with visually representing transducer-to-tissue contact via the second portion of the at least the portion of the envelope, is a first particular visual characteristic set, wherein the different visual characteristics, which indicate the different degrees of detected transducer-to-tissue contact via the graphical elements of the first set of graphical elements corresponding to the respective ones of the plurality of transducers associated with the different degrees of detected transducer-to-tissue contact, belong to a second particular visual characteristic set, and wherein the first particular visual characteristic set and the second particular visual characteristic set represent a same degree of transducer-to-tissue contact with a same color.

6. The catheter navigation of claim 4, wherein the particular visual characteristic set, which is associated with visually representing transducer-to-tissue contact via the second portion of the at least the portion of the envelope, is a first particular visual characteristic set, wherein the different visual characteristics, which indicate the different degrees of detected transducer-to-tissue contact via the graphical elements of the first set of graphical elements corresponding to the respective ones of the plurality of transducers associated with the different degrees of detected transducer-to-tissue contact, belong to a second particular visual characteristic set, wherein the first particular visual characteristic set and the second particular visual characteristic set represent a same degree of transducer-to-tissue contact with different colors.

7. The catheter navigation system of claim 1, wherein the first set of graphical elements comprises a first graphical element, and wherein the display of the first set of graphical elements of the plurality of graphical elements and the first portion of the at least the portion of the envelope in the graphically-overlapping manner includes a blending of (i) a first color of at least a part of the first graphical element with (ii) a second color of an overlapping region in the at least the first portion of the at least the portion of the envelope that overlaps the at least the part of the first graphical element.

8. The catheter navigation system of claim 1, wherein the data processing device system is configured at least by the program at least to:

receive a plurality of contact signal sets from a first set of transducers of the plurality of transducers, each contact signal set of the plurality of contact signal sets indicating a degree of transducer-to-tissue contact between each transducer of the first set of transducers and a tissue surface within the bodily cavity, and each contact signal set corresponding to a respective location in the sequence of locations of the at least the portion of the catheter in the bodily cavity;

receive a plurality of tissue-electrical-information signal sets from a second set of transducers of the plurality of transducers, the plurality of tissue-electrical-information signal sets indicating an electrical property set associated at least in part with a body including the bodily cavity and detected by the second set of transducers; and cause the display device system, based at least on some tissue-electrical-information signals of the plurality of tissue-electrical-information signal sets, to visually represent the at least the portion of the envelope in a manner that visually indicates at least a portion of the electrical property set in at least some greater-contact regions of the at least the portion of the envelope, but with no visual indication of the electrical property set in at least a no-tissue-contact region of the at least the portion of the envelope, the greater-contact regions associated with transducer-to-tissue contact and the no-tissue-contact region associated with no transducer-to-tissue contact via the at least some contact signals of the plurality of contact signal sets.

9. The catheter navigation system of claim 8, wherein the at least some greater-contact regions and the no-tissue-contact region are in the first portion of the at least the portion of the envelope.

10. The catheter navigation system of claim 8, wherein the at least some greater-contact regions and the no-tissue-contact region are in the second portion of the at least the portion of the envelope.

11. The catheter navigation system of claim 8, wherein at least one greater-contact region of the at least some greater-contact regions is in the first portion of the at least the portion of the envelope, and wherein a no-tissue-contact region is in the second portion of the at least the portion of the envelope.

12. The catheter navigation system of claim 8, wherein the second set of transducers is the first set of transducers.

13. The catheter navigation system of claim 12, wherein the no-tissue-contact region corresponds to at least part of a port that interrupts the tissue surface within the bodily cavity.

14. The catheter navigation system of claim 12, wherein the no-tissue-contact region is surrounded by at least some of the greater-contact regions.

15. The catheter navigation system of claim 1, wherein the data processing device system is configured at least by the program at least to:

receive a first contact signal set from a first set of transducers of the plurality of transducers, the first set of transducers respectively corresponding to the first set of graphical elements, the first contact signal set indicating a degree of transducer-to-tissue contact between each transducer of the first set of transducers and a tissue surface within the bodily cavity, and the first contact signal set corresponding to the particular location in the sequence of locations of the at least the portion of the catheter in the bodily cavity; and cause the display device system to display, in the state representative of the at least the portion of the catheter being in the particular location in the sequence of locations and based at least on the received first contact signal set, each graphical element in the first set of graphical elements in accordance with a first visual characteristic set indicating a degree of transducer-to-tissue contact detected by the respective transducer of the at least the first set of transducers of the plurality of transducers.

16. The catheter navigation system of claim 15, wherein the data processing device system is configured at least by the program at least to:

receive a second contact signal set from a second set of transducers of the plurality of transducers, the second contact signal set indicating a degree of transducer-to-tissue contact between each transducer of the second set of transducers and the tissue surface within the bodily cavity in the prior state representative of the at least the portion of the catheter being in the earlier location in the sequence of locations; and cause the display device system to display, in the state representative of the at least the portion of the catheter being in the particular location in the sequence of locations and based at least on the received second contact signal set, the second portion of the at least the portion of the envelope displayed without overlapping or being overlapped by any of the graphical elements and with the particular visual characteristic set indicative of the degree-of-tissue-contact detected, in the prior state representative of the at least the portion of the catheter being in the earlier location in the sequence of locations, by the particular set of transducers of the plurality of transducers.

17. The catheter navigation system of claim 1, wherein the input-output device system comprises a catheter-device-location tracking system, and wherein the data processing device system is configured at least by the program at least to receive the plurality of location signal sets from the catheter-device-location tracking system.

18. The catheter navigation system of claim 17, wherein the catheter-device-location tracking system is configured to generate the plurality of location signal sets at least in response to one or more electric fields producible by one or more devices of the catheter-device-location tracking system.

19. The catheter navigation system of claim 18, wherein the one or more devices of the catheter-device-location tracking system are configured to operate outside a body comprising the bodily cavity.

20. The catheter navigation system of claim 17, wherein the catheter-device-location tracking system is configured to generate the plurality of location signal sets at least in response to one or more magnetic fields producible by one or more devices of the catheter-device-location tracking system.

21. The catheter navigation system of claim 20, wherein the one or more devices of the catheter-device-location tracking system are configured to operate outside a body comprising the bodily cavity.

22. A method executed by a programmed data processing device system of a catheter navigation system, the method comprising:

receiving a plurality of location signal sets, each location signal set of the plurality of location signal sets indicative of a respective location in a sequence of locations at which at least a portion of a catheter has sequentially moved to in a bodily cavity, the catheter comprising a plurality of transducers arrangeable in a first spatial distribution, each transducer of the plurality of transducers configured to detect a degree of transducer-to-tissue contact; and generating and causing a display device system communicatively connected to the programmed data processing device system to concurrently display, in a state representative of the at least the portion of the catheter being in a particular location in the sequence of locations, at least (a) at least a portion of an envelope representing an interior volume of the bodily cavity based at least on the received plurality of location signal sets, and (b) a plurality of graphical elements, each graphical element corresponding to a transducer of the plurality of transducers, wherein the generating and causing the display device system to concurrently display at least (a) and (b) includes, in the state representative of the at least the portion of the catheter being in the particular location in the sequence of locations, a display of a first set of graphical elements of the plurality of graphical elements and a first portion of the at least the portion of the envelope in a graphically-overlapping manner, concurrently with a second portion of the at least the portion of the envelope displayed without overlapping or being overlapped by any of the graphical elements and in accordance with a particular visual characteristic set indicative of a degree-of-tissue-contact detected, in a prior state representative of the at least the portion of the catheter being in an earlier location in the sequence of locations, by a particular set of transducers of the plurality of transducers, the earlier location being earlier in the sequence of locations than the particular location in the sequence of locations, wherein the plurality of graphical elements is graphically displayed, in the state representative of the at least the portion of the catheter being in the particular location in the sequence of locations, in a second distribution corresponding to the first spatial distribution, and wherein the first portion of the at least the portion of the envelope is mutually exclusive with the second portion of the at least the portion of the envelope.

23. One or more non-transitory computer-readable storage mediums storing a computer-executable program, the program comprising:

location signal set receiving instructions configured to cause reception of a plurality of location signal sets, each location signal set of the plurality of location signal sets indicative of a respective location in a sequence of locations at which at least a portion of a catheter has sequentially moved to in a bodily cavity, the catheter comprising a plurality of transducers arrangeable in a first spatial distribution, each transducer of the plurality of transducers configured to detect a degree of transducer-to-tissue contact; and concurrent display instructions configured to generate and cause a display device system to concurrently display, in a state representative of the at least the portion of the catheter being in a particular location in the sequence of locations, at least (a) at least a portion of an envelope representing an interior volume of the bodily cavity based at least on the received plurality of location signal sets, and (b) a plurality of graphical elements, each graphical element corresponding to a transducer of the plurality of transducers, wherein the concurrent display instructions are configured to cause the display device system to concurrently display at least (a) and (b) as including, in the state representative of the at least the portion of the catheter being in the particular location in the sequence of locations, a display of a first set of graphical elements of the plurality of graphical elements and a first portion of the at least the portion of the envelope in a graphically-overlapping manner, concurrently with a second portion of the at least the portion of the envelope displayed without overlapping or being overlapped by any of the graphical elements and in accordance with a particular visual characteristic set indicative of a degree-of-tissue-contact detected, in a prior state representative of the at least the portion of the catheter being in an earlier location in the sequence of locations, by a particular set of transducers of the plurality of transducers, the earlier location being earlier in the sequence of locations than the particular location in the sequence of locations, wherein the program comprises graphical element display instructions configured to cause the display device system to graphically display the plurality of graphical elements, in the state representative of the at least the portion of the catheter being in the particular location in the sequence of locations, in a second distribution consistent with the first spatial distribution, and wherein the first portion of the at least the portion of the envelope is mutually exclusive with the second portion of the at least the portion of the envelope.

* * * * *